(12) United States Patent
Malik

(10) Patent No.: US 11,970,707 B2
(45) Date of Patent: Apr. 30, 2024

(54) STRONG INSULATOR AND USES THEREOF IN GENE DELIVERY

(71) Applicant: CHILDREN'S HOSPITAL MEDICAL CENTER, Cincinnati, OH (US)

(72) Inventor: Punam Malik, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 691 days.

(21) Appl. No.: 16/648,118

(22) PCT Filed: Sep. 18, 2018

(86) PCT No.: PCT/US2018/051590
§ 371 (c)(1),
(2) Date: Mar. 17, 2020

(87) PCT Pub. No.: WO2019/056015
PCT Pub. Date: Mar. 21, 2019

(65) Prior Publication Data
US 2020/0255860 A1  Aug. 13, 2020

Related U.S. Application Data

(60) Provisional application No. 62/559,751, filed on Sep. 18, 2017.

(51) Int. Cl.
*C12N 15/86* (2006.01)
*C12N 7/00* (2006.01)
(Continued)

(52) U.S. Cl.
CPC ............... *C12N 15/86* (2013.01); *C12N 7/00* (2013.01); *C12N 9/22* (2013.01); *C12N 15/113* (2013.01);
(Continued)

(58) Field of Classification Search
None
See application file for complete search history.

(56) References Cited

U.S. PATENT DOCUMENTS 4,777,128 A   10/1988 Lippa
5,219,740 A   6/1993 Miller et al.
(Continued)

FOREIGN PATENT DOCUMENTS

CN   105039407 A   11/2015
DE   4318387 A1 * 12/1994 ........... C07K 14/005
(Continued)

OTHER PUBLICATIONS

De Celis et al., "Structure and function of the long terminal repeat of the chimpanzee foamy virus isolates (SFV-6)," Arch Virol 138: 345-355 (Year: 1994).*
(Continued)

Primary Examiner — M Franco G Salvoza
(74) Attorney, Agent, or Firm — Frost Brown Todd LLP

(57) ABSTRACT

A strong insulator fragment from foamy virus, which can be used to insulate expression of a transgene and reduce genotoxicity of integrating vectors comprising such. The insulator fragment can also be used in gene targeting constructs in gene editing.

24 Claims, 17 Drawing Sheets

Specification includes a Sequence Listing.

(51) Int. Cl.
    *C12N 9/22*           (2006.01)
    *C12N 15/113*       (2010.01)

(52) U.S. Cl.
    CPC ............... *C12N 2310/20* (2017.05); *C12N 2740/10043* (2013.01); *C12N 2740/13043* (2013.01); *C12N 2740/15043* (2013.01); *C12N 2800/80* (2013.01); *C12N 2830/40* (2013.01); *C12N 2830/60* (2013.01)

(56) References Cited

U.S. PATENT DOCUMENTS

| | | | |
|---|---|---|---|
| 5,399,346 | A | 3/1995 | Anderson et al. |
| 5,650,309 | A | 7/1997 | Wong-Staal et al. |
| 5,698,443 | A | 12/1997 | Henderson et al. |
| 5,827,703 | A | 10/1998 | Debs et al. |
| 7,696,334 | B1 | 4/2010 | Bentwich |
| 7,807,618 | B2 | 10/2010 | Matalon |
| 7,901,671 | B2 | 3/2011 | LeBoulch et al. |
| 2003/0211581 | A1* | 11/2003 | Herr .................. C12N 15/85 435/325 |
| 2011/0293705 | A1 | 12/2011 | Irvine et al. |
| 2011/0294114 | A1 | 12/2011 | Van Der Loo et al. |
| 2011/0294873 | A1 | 12/2011 | Mermod et al. |
| 2012/0115227 | A1 | 5/2012 | Cohen-Haguenauer et al. |
| 2015/0316511 | A1 | 11/2015 | Guo |
| 2016/0032318 | A1 | 2/2016 | Molina et al. |
| 2020/0399655 | A1* | 12/2020 | Slepushkin ...... C07K 14/70578 |

FOREIGN PATENT DOCUMENTS

| | | | |
|---|---|---|---|
| EP | 0345242 | A2 | 12/1989 |
| GB | 2200651 | | 8/1988 |
| WO | WO 90/07936 | A1 | 7/1990 |
| WO | WO 91/02805 | A2 | 3/1991 |
| WO | WO 93/03769 | A1 | 3/1993 |
| WO | WO 93/10218 | A1 | 5/1993 |
| WO | WO 93/11230 | A1 | 6/1993 |
| WO | WO 93/19191 | A1 | 9/1993 |
| WO | WO 93/25234 | A1 | 12/1993 |
| WO | WO 93/25698 | A1 | 12/1993 |
| WO | WO 94/03622 | A1 | 2/1994 |
| WO | WO 94/12649 | A2 | 6/1994 |
| WO | WO 94/28938 | A1 | 12/1994 |
| WO | WO 95/00655 | A1 | 1/1995 |
| WO | WO 95/11984 | A2 | 5/1995 |
| WO | WO 2010/113037 | A1 | 10/2010 |
| WO | WO 2015/028683 | A1 | 3/2015 |
| WO | WO-2015028683 | A1 * | 3/2015 ............ C12N 15/86 |
| WO | WO 2015/117027 | A1 | 8/2015 |
| WO | WO 2015/138852 | A1 | 9/2015 |
| WO | WO-2018152371 | A1 * | 8/2018 ........... A61K 31/395 |

OTHER PUBLICATIONS

Guntaka, "Transcription Termination and Polyadenylation in Retroviruses," Microbiological Reviews, vol. 57, No. 3 (Year: 1993).*
WIPO English translation of Meulen et al. (DE4318387A1) (Year: 1994).*
Schambach et al., "Improving Transcriptional Termination of Self-inactivating Gamma-retroviral and Lentiviral Vectors," Molecular Therapy, vol. 15, No. 6: 1167-1173 (Year: 2007).*
Aiuti, A., et al., "Lentivirus-based Gene Therapy of Hematopoietic Stem Cells in Wiskott-Aldrich Syndrome," Science, 2013, 341(6148):1233151, 29 pgs.
Altschul, S.F., et al., "Basic Local Alignment Search Tool," J Mol Biol, 1990, 215:403-410, 8 pgs.
Altschul, S.F., et al., "Gapped BLAST and PSI-BLAST: a new generation of protein database search programs," Nucleic Acids Res, 1997, 25(17):3389-3402, 14 pgs.
Arumugam, P.I., et al., "Genotoxic Potential of Lineage-Specific Lentivirus Vectors Carrying the B-Globin Locus Control Region," Mol Ther, 2009, 17(11): 1929-1937, 9 pgs.
Arumugam, P.I., et al., "The 3' Region of the Chicken Hypersensitive Site-4 Insulator Has Properties Similar to Its Core and Is Required for Full Insulator Activity," PLOS One, 2009, 4(9): e6995, 15 pgs.
Ausubel, F.M., et al., Current Protocols in Molecular Biology, New York, John Wiley & Sons, 2006, Table of Contents Only, 4 pgs.
Barde, I., et al., "Lineage- and stage-restricted lentiviral vectors for the gene therapy of chronic granulomatous disease," Gene Ther, 2011, 18:1087-1097, 11 pgs.
Bauer, T.R., Jr., et al., "Correction of the disease phenotype in canine leukocyte adhesion deficiency using ex vivo hematopoietic stem cell gene therapy," Blood, 2006, 108:3313-3320, 8 pgs.
Bauer, T.R., Jr., et al., "Successful treatment of canine leukocyte adhesion deficiency by foamy virus vectors," Nat Med, 2008, 14(1):93-97, 12 pgs.
Bauer, T.R., Jr., et al., "Treatment of canine leukocyte adhesion deficiency by foamy virus vectors expressing CD18 from a PGK promoter," Gene Ther, 2011, 18(6):553-559, 18 pgs.
Beard, B.C., et al., "Unique Integration Profiles in a Canine Model of Long-Term Repopulating Cells Transduced with Gammaretrovirus, Lentivirus, or Foamy Virus," Hum Gene Ther, 2007, 18:423-434, 12 pgs.
Boztug, K., et al., "Stem-Cell Gene Therapy for the Wiskott-Aldrich Syndrome," N Engl J Med, 2010, 363(20): 1918-1927, 14 pgs.
Brinkman, E.K., et al., "Easy quantitative assessment of genome editing by sequence trace decomposition," Nucleic Acids Res, 2014, 42(22):e168, 8 pgs.
Browning, D.L., et al., "Evidence for the in vivo safety of insulated foamy viral vectors," Gene Ther, 2017, 24(3):187-198, 28 pgs.
Browning, D.L., et al., "Insulated Foamy Viral Vectors," Human Gene Therapy, 2016, 27(3):255-266, 12 pgs.
Certo, M.T., et al., "Salient Features of Endonuclease Platforms for Therapeutic Genome Editing," Mol Ther, 2016, 24(3): 422-429, 8 pgs.
Chiriaco, M., et al., "Dual-regulated Lentiviral Vector for Gene Therapy of X- linked Chronic Granulomatosis," Mol Ther, 2014, 22(8): 1472-1483, 12 pgs.
Cuddapah, S., et al., "Global analysis of the insulator binding protein CTCF in chromatin barrier regions reveals demarcation of active and repressive domains," Genome Res, 2009, 19:24-32, 9 pgs.
Du, Y., et al., "Cooperating cancer-gene identification through oncogenic-retrovirus-induced insertional mutagenesis," Blood, 2005, 106:2498-2505, 8 pgs.
Emery, D.W., "the Use of Chromatin Insulators to Improve the Expression and Safety of Integrating Gene Transfer Vectors," Human Gene Therapy, 2011, 22(6): 761-774, 14 pgs.
Ertel, M.K., et al., "CTCF Occupation of the Herpes Simplex Virus 1 Genome Is Disrupted at Early Times Post Reactivation in a Transcription-Dependent Manner," J Virol, 2012, 86(23): 12741-12759, 19 pgs.
Everson, E.M., et al., "A comparison of foamy and lentiviral vector genotoxicity in SCID- repopulating cells shows foamy vectors are less prone to clonal dominance," Mol Ther Methods Clin Dev, 2016, 3:16048, 9 pgs.
Falcone, V., et al., "Replication of primate foamy viruses in natural and experimental hosts," Ch. 7 in Curr Top Microbiol Immunol, 2003, 277:161-180, 20 pgs.
Gaj, T., et al., "Zfn, Talen and CRISPR/Cas-based methods for genome engineering," Trends Biotechnol, 2013, 31(7):397-405, 20 pgs.
Gibson, D.G., et al., "Enzymatic assembly of DNA molecules up to several hundred kilobases," Nature Methods, 2009, 6(5):343-345, 5 pgs.
Goodman, M.A., et al., "Foamy Virus Backbone Has Insulator Properties Which Remarkably Reduces Its Genotoxicity Potential," Blood, 2016, 128 (22):1002, 3 pgs., Abstract Only.
Goodman, M.A., et al., "Foamy Virus Vector Carries a Strong Insulator in Its Long Terminal Repeat Which Reduces Its Genotoxic Potential," J Virol, 2018, 92(1):e01639-17, 25 pgs.
Goodman, M.A., et al., "The potential of gene therapy approaches for treatment of hemoglobinopathies: achievements and challenges," Ther Adv Hematol, 2016, 7(5):302-315, 14 pgs.

(56) References Cited

OTHER PUBLICATIONS

Green, M.R. and J. Sambrook, Molecular Cloning: A Laboratory Manual, New York, Cold Spring Harbor Laboratory Press, 2012, Table of Contents Only, 29 pgs.
Hacein-Bey-Abina, S., et al., "Efficacy of Gene Therapy for X-Linked Severe Combined Immunodeficiency," N Engl J Med, 2010, 363(4):355-364, 13 pgs.
Hacein-Bey-Abina, S., et al., "Insertional oncogenesis in 4 patients after retrovirus- mediated gene therapy of SCID-X1," J Clin Invest, 2008, 118(9):3132-3142, 11 pgs.
Hacein-Bey-Abina, S., et al., "LMO2-Associated Clonal T Cell Proliferation in Two Patients after Gene Therapy for SCID-X1," Science, 2003, 302:415-419, 6 pgs.
Hacein-Bey-Abina, S., et al., "Outcomes following Gene Therapy in Patients with Severe Wiskott-Aldrich Syndrome," JAMA, 2015, 313(15): 1550-1563, 21 pgs.
Hark, A.T., et al., "CTCF mediates methylation-sensitive enhancer-blocking activity at the H19/Igf2 locus," Nature, 2000, 405:486-489, 4 pgs.
Hendrie, P.C., et al., "A Rapid and Quantitative Assay for Measuring Neighboring Gene Activation by Vector Proviruses," Mol Ther, 2008, 16(3): 534-540, 7 pgs.
Hocum, J.D., et al., "Retargeted Foamy Virus Vectors Integrate Less Frequently Near Proto-oncogenes," Sci Rep, 2016, 6:36610, 11 pgs.
Howe, S.J., et al., "Insertional mutagenesis combined with acquired somatic mutations causes leukemogenesis following gene therapy of SCID-X1 patients," J Clin Invest, 2008, 118(9):3143-3150, 8 pgs.
Hughes, D.J., et al., "Contributions of CTCF and DNA Methyltransferases DNMT1 and DNMT3B to Epstein-Barr Virus Restricted Latency," J Virol, 2012, 86:1034-1045, 12 pgs.
Hunter, M.J., et al., "Gene Therapy for Canine Leukocyte Adhesion Deficiency with Lentiviral Vectors Using the Murine Stem Cell Virus and Human Phosphoglycerate Kinase Promoters," Hum Gene Ther, 2011, 22:689-696, 8 pgs.
Josephson, N.C., et al., "Transduction of human NOD/SCID-repopulating cells with both lymphoid and myeloid potential by foamy virus vectors," Proc Natl Acad Sci USA, 2002, 99(2):8295-8300, 6 pgs.
Josephson, N.C., et al., "Transduction of Long-Term and Mobilized Peripheral Blood-Derived NOD/SCID Repopulating Cells by Foamy Virus Vectors," Hum Gene Ther, 2004, 15:87-92, 9 pgs.
Karlin, S., et al., "Applications and statistics for multiple high-scoring segments in molecular sequences," Proc Natl Acad Sci USA, 1993, 90:5873-5877, 5 pgs.
Karlin, S., et al., "Methods for assessing the statistical significance of molecular sequence features by using general scoring schemes," Proc Natl Acad Sci USA, 1990, 87:2264-2268, 5 pgs.
Kiem, H-P., et al., "Charting a Clear Path: The ASGCT Standardized Pathways Conference," Mol Ther, 2014, 22(7): 1235-1238, 4 pgs.
Kiem, H-P., et al., "Foamy virus-mediated gene transfer to canine repopulating cells," Blood, 2007, 109(1):65-70, 6 pgs.
Kustikova, O., et al., "Clonal Dominance of Hematopoietic Stem Cells Triggered by Retroviral Gene Marking," Science, 2005, 308:1171-1174, 4 pgs.
Landau, N.R., et al., "Packaging System for Rapid Production of Murine Leukemia Virus Vectors with Variable Tropism," J Virol, 1992, 66(8):5110-5113, 4 pgs.
Lang, F., et al., "CTCF interacts with the lytic HSV-1 genome to promote viral transcription," Sci Rep, 2017, 7:39861, 15 pgs.
Leurs, C., et al., "Comparison of Three Retroviral Vector Systems for Transduction of Nonobese Diabetic/Severe Combined Immuno-deficiency Mice Repopulating Human CD34+ Cord Blood Cells," Hum Gene Ther, 2003, 14:509-519, 11 pgs.
Liu, M., et al., "Genomic discovery of potent chromatin insulators for human gene therapy," Nat Biotechnol, 2015, 33(2): 198-203, 8 pgs.
Maetzig, T., et al., "Gammaretroviral Vectors: Biology, Technology and Application," Viruses, 2011, 3(6):677-713, 37 pgs.
Maruggi, G., et al., "Transcriptional Enhancers Induce Insertional Gene Deregulation Independently From the Vector Type and Design," Mol Ther, 2009, 17(5):851-856, 6 pgs.
Mehta, K., et al., "Human Papillomaviruses Activate and Recruit SMC1 Cohesion Proteins for the Differentiation-Dependent Life Cycle through Association with CTCF Insulators," PLOS Pathog, 2015, 11(4):e1004763, 25 pgs.
Mergia, A., et al., "Foamy virus vectors," Ch. 6 in Curr Top Microbiol Immunol, 2003, 277:131-159, 29 pgs.
Modlich, U., et al., "Cell-culture assays reveal the importance of retroviral vector design for insertional genotoxicity," Blood, 2006, 108:2545-2553, 9 pgs.
Modlich, U., et al., "Insertional Transformation of Hematopoietic Cells by Self-Inactivating Lentiviral and Gammaretroviral Vectors," Mol Ther, 2009, 17(11): 1919-1928, 10 pgs.
Montini, E., et al., "Hematopoietic stem cell gene transfer in a tumor-prone mouse model uncovers low genotoxicity of lentiviral vector integration," Nat Biotechnol, 2006, 24(6):687-696, 10 pgs.
Montini, E., et al., "The genotoxic potential of retroviral vectors is strongly modulated by vector design and integration site selection in a mouse model of HSC gene therapy," J Clin Invest, 2009, 119(4):964-975, 12 pgs.
Morianos, I., et al., "Comparative analysis of FV vectors with human a- or 8-globin gene regulatory elements for the correction of B-thalassemia," Gene Ther, 2012, 19:303-311, 9 pgs.
Natkunam, Y., et al., "The oncoprotein LMO2 is expressed in normal germinal- center B cells and in human B-cell lymphomas," Blood, 2007, 109:1636-1642, 7 pgs.
Ong, C-T., et al., "CTCF: An Architectural Protein Bridging Genome Topology and Function," Nat Rev Genet, 2014, 15(4):234-246, 25 pgs.
Ott, M.G., et al. "Correction of X-linked chronic granulomatous disease by gene therapy, augmented by insertional activation of MDS1-EVI1, PRDM16 or SETBP1," Nature Medicine, 2006, 12(4):401-409, 9 pgs.
Paris, C., et al., "CCCTC-Binding Factor Recruitment to the Early Region of the Human Papillomavirus 18 Genome Regulates Viral Oncogene Expression," J Virol, 2015, 89(9):4770-4785, 16 pgs.
Puthenveetil, G., et al., "Successful correction of the human B-thalassemia major phenotype using a lentiviral vector," Blood, 2004, 104:3445-3453, 9 pgs.
Rethwilm, A., "Regulation of Foamy Virus Gene Expression," Curr Top Microbiol Immunol, 1995, 193:1-24, 24 pgs.
Russell, D.W., et al., "Foamy Virus Vectors," J Virol, 1996, 70(1):217-222, 6 pgs.
Ryu, B.Y., et al., "An experimental system for the evaluation of retroviral vector design to diminish the risk for proto-oncogene activation," Blood, 2008, 111:1866-1875, 10 pgs.
Satou, Y., et al., "The retrovirus HTLV-1 inserts an ectopic CTCF-binding site into the human genome," Proc Natl Acad Sci USA, 2016, 113(11):3054-3059, 6 pgs.
Schambach, A., et al., "Equal Potency of Gammaretroviral and Lentiviral SIN Vectors for Expression of 06-Methylguanine-DNA Methyltransferase in Hematopoietic Cells," Mol Ther, 2006, 13(2):391-400, 10 pgs.
Schmidt, D., et al., "Waves of Retrotransposon Expansion Remodel Genome Organization and CTCF Binding in Multiple Mammalian Lineages," Cell, 2012, 148:335-348, 16 pgs.
Schmittgen, T.D., et al., "Analyzing real-time PCR data by the comparative CT method," Nat Protocols, 2008, 3(6):1101-1108, 8 pgs.
Shou, Y., et al., "Unique risk factors for insertional mutagenesis in a mouse model of XSCID gene therapy," Proc Natl Acad Sci, 2006, 103(31): 11730-11735, 6 pgs.
Soneoka, Y., et al., "A transient three-plasmid expression system for the production of high titer retroviral vectors," Nucl Acids Res, 1995, 23(4):628-633, 6 pgs.
Spencer, R.J., et al., "A Boundary Element Between Tsix and Xist Binds the Chromatin Insulator Ctcf and Contributes to Initiation of X-Chromosome Inactivation," Genetics, 2011, 189:441-454, 15 pgs.

(56) References Cited

OTHER PUBLICATIONS

Stein, S., et al., "Genomic instability and myelodysplasia with monosomy 7 consequent to EVI1 activation after gene therapy for chronic granulomatous disease," Nat Med, 2010, 16(2): 198-204, 8 pgs.

Tiwari, S., et al., "High Level of Perforin Expression Is Required for Effective Correction of Hemophagocytic Lymphohistiocytosis," Hum Gene Ther, 2016, 27(10):847-859, 13 pgs.

Trobridge, G., et al., "Gene Transfer with Foamy Virus Vectors," Ch. 37 in Methods Enzymol, 2002, 346:628-648, 21 pgs.

Trobridge, G., et al., "Improved Foamy Virus Vectors with Minimal Viral Sequences," Mol Ther, 2002, 6(3):321-328, 8 pgs.

Trobridge, G.D., et al., "Foamy virus vector integration sites in normal human cells," Proc Natl Acad Sci USA, 2006, 103(5): 1498-1503, 6 pgs.

Uchiyama, T., et al., "Foamy Virus Vector-Mediated Gene Correction of a Mouse Model of Wiskott-Aldrich Syndrome," Mol Ther, 2012, 20(6): 1270-1279, 10 pgs.

Vassilopoulos, G., et al., "Gene transfer into murine hematopoietic stem cells with helper-free foamy virus vectors," Blood, 2001, 98:604-609, 6 pgs.

West, A.G., et al., "Insulators: many functions, many mechanisms," Genes & Development, 2002, 16(3):271-88, 19 pgs.

Will, E., et al., "HOXB4 Inhibits Cell Growth in a Dose-Dependent Manner and Sensitizes Cells Towards Extrinsic Cues," Cell Cycle, 2006, 5(1): 14-22, 9 pgs.

Ziebarth, J.D., et al., "CTCFBSDB 2.0: a database for CTCF-binding sites and genome organization," Nucleic Acids Res, 2013, 41:D188-D194, 7 pgs.

Zychlinski, D., et al., "Physiological Promoters Reduce the Genotoxic Risk of Integrating Gene Vectors," Mol Ther, 2008, 16(4):718-725, 8 pgs.

Chinese Office Action, Notice of the First Office Action, dated Feb. 22, 2023 for Application No. CN 201880057176.7, 12 pgs.

European Search Report and Written Opinion dated Jul. 5, 2021 for Application No. EP 18856238.3, 12 pgs.

International Search Report and Written Opinion dated Mar. 13, 2019 for Application No. PCT/US2018/051590, 13 pgs.

U.S. Appl. No. 62/559,751, filed Sep. 18, 2017, by Malik, entitled: "Foamy Virus Vector Carries a Strong Insulator.".

* cited by examiner

```
CATCATTTAAGATAA  GTGTAGTTCACA  CTTATATCACTA  GATGTCTCCCTT  AGCAAGGCTAAT  ATACAAATCCTTTTACT
                        Mutated Regions (12 bp/region)                    (SEQ ID NO: 74)
                   1             2             3             4
Mutant 1
CATCATTTAAGATAA  GATATAAAGCCT  CTTATATCACTA  GATGTCTCCCTT  AGCAAGGCTAAT  ATACAAATCCTTTTACT
Mutant 2                                                                 (SEQ ID NO: 92)
CATCATTTAAGATAA  GTGTAGTTCACA  GATATAAAGCCT  GATGTCTCCCTT  AGCAAGGCTAAT  ATACAAATCCTTTTACT
Mutant 3                                                                 (SEQ ID NO: 94)
CATCATTTAAGATAA  GTGTAGTTCACA  CTTATATCACTA  GATATAAAGCCT  AGCAAGGCTAAT  ATACAAATCCTTTTACT
Mutant 4                                                                 (SEQ ID NO: 96)
CATCATTTAAGATAA  GTGTAGTTCACA  CTTATATCACTA  GATGTCTCCCTT  GATATAAAGCCT  ATACAAATCCTTTTACT
Mutant 5                                                                 (SEQ ID NO: 98)
CATCATTTAAGATAA  GATATAAAGCCT  CTTATATCACTA  TCGAATGTGCTT  AGCAAGGCTAAT  ATACAAATCCTTTTACT
Mutant 6                                                                 (SEQ ID NO: 100)
CATCATTTAAGATAA  GTGTAGTTCACA  GATATAAAGCCT  TCGAATGTGCTT  AGCAAGGCTAAT  ATACAAATCCTTTTACT
                                                                         (SEQ ID NO: 102)
```

FIG. 7D

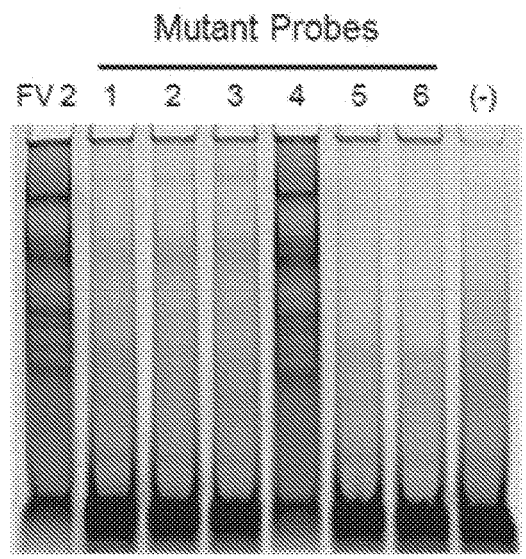

FIG. 7E

SEQUENCE LISTING

```
<160> NUMBER OF SEQ ID NOS: 147

<210> SEQ ID NO 1
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 1
gtgtagttca cacttatatc actagatgtc tccctt                                 36

<210> SEQ ID NO 2
```

```
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 2
aagggagaca tctagtgata taagtgtgaa ctacac                                 36

<210> SEQ ID NO 3
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 3
tttatttgtg aaatttgtga tgctattgct ttatttgtaa accg                       44

<210> SEQ ID NO 4
<211> LENGTH: 140
<212> TYPE: DNA
<213> ORGANISM: Artificial Sequence
<220> FEATURE:
<223> OTHER INFORMATION: Synthetic polynucleotide

<400> SEQUENCE: 4
tcgacgcagg actcggcttg ctgaagcgcg cacggcaaga ggcgaggggc ggcgactggt       60
gagtacgcca aaaattttga ctagcggagg ctagaaggag agagatgggt gcgagagcgt      120
cagtattaag cggggagaa                                                   140

<210> SEQ ID NO 5
<211> LENGTH: 858
<212> TYPE: DNA
<213> ORGANISM: Artificial Sequence
<220> FEATURE:
<223> OTHER INFORMATION: Synthetic polynucleotide

<400> SEQUENCE: 5
gatcttcaga cctggaggag gagatatgag ggacaattgg agaagtgaat tatataaata       60
taaagtagta aaaattgaac cattaggagt agcacccacc aaggcaaaga gaagagtggt      120
gcagagagaa aaaagagcag tgggaatagg agctttgttc cttgggttct gggagcagc       180 aggaagcact atgggcgcag cgtcaatgac gctgacggta caggccagac aattattgtc      240
tggtatagtg cagcagcaga acaatttgct gagggctatt gaggcgcaac agcatctgtt      300
gcaactcaca gtctggggca tcaagcagct ccaggcaaga atcctggctg tggaaagata      360
cctaaaggat caacagctcc tggggatttg gggttgctct ggaaaactca tttgcaccac      420
tgctgtgcct tggaatgcta gttggagtaa taaatctctg aacagatttt ggaatcacac      480
gacctggatg gagtgggaca gagaaattaa caattacaca agcttaatac actccttaat      540
tgaagaatcg caaaaccagc aagaaaagaa tgaacaagaa ttattggaat tagataaatg      600
ggcaagtttg tggaattggt ttaacataac aaattggctg tggtatataa aattattcat      660
aatgatagta ggaggcttgg taggtttaag aatagttttt gctgtacttt ctatagtgaa      720
tagagttagg cagggatatt caccattatc gtttcagacc cacctcccaa ccccgagggg      780
acccgacagg cccgaaggaa tagaagaaga aggtggagag agagacagag acagatccat      840
tcgattagtg aacggatc                                                   858
```

```
<210> SEQ ID NO 6
<211> LENGTH: 355
<212> TYPE: DNA
<213> ORGANISM: Artificial Sequence
<220> FEATURE:
<223> OTHER INFORMATION: Synthetic polynucleotide

<400> SEQUENCE: 6
atgggtgcga gagcgtcagt attaagcggg ggagaattag atcgcgatgg gaaaaaattc      60
ggttaaggcc agggggaaag aaaaaatata aattaaaaca tatagtatgg gcaagcaggg     120
agctagaacg attcgcagtt aatcctggcc tgttagaaac atcagaaggc tgtagacaaa     180
tactgggaca gctacaacca tcccttcaga caggatcaga agaacttaga tcattatata     240
atacagtagc aaccctctat tgtgtgcatc aaaggataga gataaaagac accaaggaag     300
ctttagacaa gatagaggaa gagcaaaaca aaagtaagac caccgcacag caagc         355

<210> SEQ ID NO 7
<211> LENGTH: 205
<212> TYPE: DNA
<213> ORGANISM: Artificial Sequence
<220> FEATURE:
<223> OTHER INFORMATION: Synthetic polynucleotide

<400> SEQUENCE: 7
ccatctgttg tttgcccctc ccccgtgcct tccttgaccc tggaaggtgc cactcccact      60
gtcctttcct aataaaatga ggaaattgca tcgcattgtc tgagtaggtg tcattctatt     120
ctggggggtg gggtggggca ggacagcaag ggggaggatt gggaagacaa tagcaggcat     180
gctggggatg cggtgggctc tatgg                                           205

<210> SEQ ID NO 8
<211> LENGTH: 1211
<212> TYPE: DNA
<213> ORGANISM: Artificial Sequence
<220> FEATURE:
<223> OTHER INFORMATION: Synthetic polynucleotide

<400> SEQUENCE: 8
gagctcacgg ggacagcccc cccccaaagc ccccagggat gtaattacgt ccctcccccg      60 ctaggggca gcagcgagcc gcccgggggct ccgctccggt ccggcgctcc ccccgcatcc     120
ccgagccggc agcgtgcggg gacagcccgg gcacggggaa ggtggcacgg gatcgctttc     180
ctctgaacgc ttctcgctgc tctttgagcc tgcagacacc tgggggggata cggggaaaaa     240 gctttaggct gaaagagaga tttagaatga cagaatcata gaacggcctg ggttgcaaag     300
gagcacagtg ctcatccaga tccaaccccc tgctatgtgc agggtcatca accagcagcc     360
caggctgccc agagccacat ccagcctggc cttgaatgcc tgcagggatg gggcatccac     420
agcctccttg ggcaacctgt tcagtgcgtc accaccctct ggggggaaaaa ctgcctcctc     480 atatccaacc caaacctccc ctgtctcagt gtaaagccat tcccccttgt cctatcaagg     540
gggagtttgc tgtgacattg ttggtctggg gtgacacatg tttgccaatt cagtgcatca     600
cggagaggca gatcttgggg ataaggaagt gcaggacagc atggacgtgg gacatgcagg     660
tgttgagggc tctgggacac tctccaagtc acagcgttca gaacagcctt aaggataaga     720
agataggata gaaggacaaa gagcaagtta aacccagca tggagaggag cacaaaaagg      780
ccacagacac tgctggtccc tgtgtctgag cctgcatgtt tgatggtgtc tggatgcaag     840
cagaaggggt ggaagagctt gcctggagag atacagctgg gtcagtagga ctgggacagg     900
```

| | |
|---|---|
| cagctggaga attgccatgt agatgttcat acaatcgtca aatcatgaag gctggaaaag | 960 |
| ccctccaaga tccccaagac caaccccaac ccacccaccg tgcccactgg ccatgtccct | 1020 |
| cagtgccaca tccccacagt tcttcatcac ctccagggac ggtgaccccc ccacctccgt | 1080 |
| gggcagctgt gccactgcag caccgctctt tggagaaggt aaatcttgct aaatccagcc | 1140 |
| cgaccctccc ctggcacaac gtaaggccat tatctctcat ccaactccag gacggagtca | 1200 |
| gtgagaatat t | 1211 |

<210> SEQ ID NO 9
<211> LENGTH: 250
<212> TYPE: DNA
<213> ORGANISM: Artificial Sequence
<220> FEATURE:
<223> OTHER INFORMATION: Synthetic polynucleotide

<400> SEQUENCE: 9

| | |
|---|---|
| gggacagccc cccccaaag ccccaggga tgtaattacg tccctccccc gctagggggc | 60 |
| agcagcgagc cgcccggggc tccgctccgg tccggcgctc cccccgcatc cccgagccgg | 120 |
| cagcgtgcgg ggacagcccg ggcacgggga aggtggcacg ggatcgcttt cctctgaacg | 180 |
| cttctcgctg ctcttttgagc ctgcagacac ctgggggggat acggggaaaa agctttaggc | 240 |
| tgaaagagat | 250 |

<210> SEQ ID NO 10
<211> LENGTH: 400
<212> TYPE: DNA
<213> ORGANISM: Artificial Sequence
<220> FEATURE:
<223> OTHER INFORMATION: Synthetic polynucleotide

<400> SEQUENCE: 10

| | |
|---|---|
| ctgagcctgc atgtttgatg gtgtctggat gcaagcagaa ggggtggaag agcttgcctg | 60 |
| gagagataca gctgggtcag taggactggg acaggcagct ggagaattgc catgtagatg | 120 |
| ttcatacaat cgtcaaatca tgaaggctgg aaaagccctc caagatcccc aagaccaacc | 180 |
| ccaacccacc caccgtgccc actggccatg tccctcagtg ccacatcccc acagttcttc | 240 |
| atcacctcca gggacggtga ccccccacc tccgtgggca gctgtgccac tgcagcaccg | 300 |
| ctctttggag aaggtaaatc ttgctaaatc cagcccgacc ctcccctggc acaacgtaag | 360 |
| gccattatct ctcatccaac tccaggacgg agtcagtgag | 400 |

<210> SEQ ID NO 11
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 11

| | |
|---|---|
| aaaagaaaag ggggga | 16 |

<210> SEQ ID NO 12
<211> LENGTH: 583
<212> TYPE: DNA
<213> ORGANISM: Artificial Sequence
<220> FEATURE:
<223> OTHER INFORMATION: Synthetic polynucleotide

<400> SEQUENCE: 12

| | |
|---|---|
| tcgacaatca acctctggat tacaaaattt gtgaaagatt gactggtatt cttaactatg | 60 |

```
ttgctccttt tacgctatgt ggatacgctg ctttaatgcc tttgtatcat gctattgctt      120
cccgtatggc tttcattttc tcctccttgt ataaatcctg gttgctgtct ctttatgagg      180
agttgtggcc cgttgtcagg caacgtggcg tggtgtgcac tgtgtttgct gacgcaaccc      240
ccactggttg gggcattgcc accacctgtc agctcctttc cgggactttc gctttccccc      300
tccctattgc cacggcggaa ctcatcgccg cctgccttgc ccgctgctgg acaggggctc      360
ggctgttggg cactgacaat ccgtggtgt tgtcggggaa gctgacgtcc tttccatggc       420
tgctcgcctg tgttgccacc tggattctgc gcgggacgtc cttctgctac gtcccttcgg      480
ccctcaatcc agcggacctt ccttcccgcg gcctgctgcc ggctctgcgg cctcttccgc      540
gtcttcgcct tcgccctcag acgagtcgga tctcccttg ggc                        583
```

<210> SEQ ID NO 13
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 13

```
aatcctttac atggagaagt tataggtctt                                       30
```

<210> SEQ ID NO 14
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 14

```
atctgaaatc tctcaatttg tccccacca                                        29
```

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15

```
gaaccttgtg tctctcatcc c                                                21
```

<210> SEQ ID NO 16
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 16

```
gacccgggag atctgaattc agtggcacag cagttagg                              38
```

<210> SEQ ID NO 17
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 17

```
aattcctaac tgctgtgcca ctgaattcag atc                                   33
```

```
<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
gtctatgagg agcaggagta                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 19
gacccgggag atctgaattc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
cctccttccc tgtaatactc                                               20

<210> SEQ ID NO 21
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 21
agtggcacag cagttagg                                                 18

<210> SEQ ID NO 22
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 22
ctggggacca tctgttcttg gccct                                         25

<210> SEQ ID NO 23
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 23
aattctctag tatgctactc gcaccgatta tctccgctgt cagt                    44

<210> SEQ ID NO 24
<211> LENGTH: 40
<212> TYPE: DNA
<213> ORGANISM: Artificial Sequence
<220> FEATURE:
<223> OTHER INFORMATION: Synthetic polynucleotide
```

```
<400> SEQUENCE: 24
actgacagcg gagataatcg gtgcgagtag catactagag                              40

<210> SEQ ID NO 25
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 25
gacttgtggt ctcgctgttc cttgg                                             25

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
actgacagcg gagataatcg                                                   20

<210> SEQ ID NO 27
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 27
ggtctcctct gagtgattga ctacc                                             25

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
gtgcgagtag catactagag                                                   20

<210> SEQ ID NO 29
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 29
tttaggttgc cctgaaaagg tg                                                22

<210> SEQ ID NO 30
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 30
gccaaacact cctaggctct tg                                                22

<210> SEQ ID NO 31
```

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
gtctctcgca gccacatggg                                              20

<210> SEQ ID NO 32
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 32
cccgtaatgc agaagaaaac catgggctgg gaggc                              35

<210> SEQ ID NO 33
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 33
gcctcccagc ccatggtttt cttctgcatt acggg                              35

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
gataccaata gatatcaatc                                              20

<210> SEQ ID NO 35
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 35
caccgggata ccaatagata tcaatc                                       26

<210> SEQ ID NO 36
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 36
aaacgattga tatctattgg tatccc                                       26

<210> SEQ ID NO 37
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 37
```
atcaccagat tgatatctat                                              20

<210> SEQ ID NO 38
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 38
caccgggatc accagattga tatctat                                      27

<210> SEQ ID NO 39
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 39
aaacatagat atcaatctgg tgatccc                                      27

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
aattgcatag tcgtgaagtc                                              20

<210> SEQ ID NO 41
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 41
caccgggaat tgcatagtcg tgaagtc                                      27

<210> SEQ ID NO 42
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 42
aaacgacttc acgactatgc aattccc                                      27

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
attgcatagt cgtgaagtca                                              20

<210> SEQ ID NO 44
<211> LENGTH: 27
<212> TYPE: DNA

<210> SEQ ID NO 44
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 44
caccgggatt gcatagtcgt gaagtca        27

<210> SEQ ID NO 45
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 45
aaactgactt cacgactatg caatccc        27

<210> SEQ ID NO 46
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 46
tcgtgaagtc agggcttcta        20

<210> SEQ ID NO 47
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 47
caccgggtcg tgaagtcagg gcttcta        27

<210> SEQ ID NO 48
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 48
aaactagaag ccctgacttc acgaccc        27

<210> SEQ ID NO 49
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 49
gcttgggttt tacacgtctt c        21

<210> SEQ ID NO 50
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 50
tcagctagaa aacaagtact tgc        23

<210> SEQ ID NO 51
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 51
agtaaaagga tttgtatatt agccttgcta agggagacat ctagtgatat aagtgtgaac    60
tacacttatc ttaaatgatg                                                80

<210> SEQ ID NO 52
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 52
agtaaaagga tttgtatatt agccttgcta agcacattcg atagtgatat aagaggcttt    60
atatcttatc ttaaatgatg                                                80

<210> SEQ ID NO 53
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 53
aagggagaca tctagtgata taagtgtgaa ctacac                              36

<210> SEQ ID NO 54
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 54
cgagcgttgg taagagaagc                                                20

<210> SEQ ID NO 55
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 55
gagatctgtc ccgctagca                                                 19

<210> SEQ ID NO 56
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 56
ggataattta caaataaacc cgacttatat tcg                                 33

<210> SEQ ID NO 57

```
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 57
tggggaacaa gtacaattttt gtg                                            23

<210> SEQ ID NO 58
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 58
caatgtggtg atatcaatct ggtg                                            24

<210> SEQ ID NO 59
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 59
acaagcgtaa attgcatagt cgtga                                           25

<210> SEQ ID NO 60
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 60
cttggtttat gaatctggct c                                               21

<210> SEQ ID NO 61
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 61
gcctttagca gttagaacac                                                 20

<210> SEQ ID NO 62
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 62
acatgctggg aatcgacttg tgat                                            24

<210> SEQ ID NO 63
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 63
```
acaagataga ggaagagcaa aacaaaagta agaccaccgc acagcaagcg gccgctgatc    60
ttcagacctg gaggaggaga tatgaggga                                     89

<210> SEQ ID NO 64
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 64
tccctcatat ctcctcctcc aggtctgaag atcagcggcc gcttgctgtg cggtggtctt    60
acttttgttt tgctcttcct ctatcttgt                                     89

<210> SEQ ID NO 65
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 65
ctcctcctcc aggt                                                     14

<210> SEQ ID NO 66
<211> LENGTH: 83
<212> TYPE: DNA
<213> ORGANISM: Artificial Sequence
<220> FEATURE:
<223> OTHER INFORMATION: Synthetic polynucleotide

<400> SEQUENCE: 66
gatacctaaa ggatcaacag ctcctgggga tttggggttg ctctggaaaa ctcatttgca    60
ccactgctgt gccttggaat gct                                           83

<210> SEQ ID NO 67
<211> LENGTH: 83
<212> TYPE: DNA
<213> ORGANISM: Artificial Sequence
<220> FEATURE:
<223> OTHER INFORMATION: Synthetic polynucleotide

<400> SEQUENCE: 67
agcattccaa ggcacagcag tggtgcaaat gagttttcca gagcaacccc aaatccccag    60
gagctgttga tcctttaggt atc                                           83

<210> SEQ ID NO 68
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 68
tccccaggag ctgttgatcc                                               20

<210> SEQ ID NO 69
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 69
gtcggggaag ctgacgtcct ttcgaattcg atatcaagct gtacctttaa gaccaatgac    60
ttacaaggca gctgtagatc                                                80

<210> SEQ ID NO 70
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 70
gatctacagc tgccttgtaa gtcattggtc ttaaaggtac agcttgatat cgaattcgaa    60
aggacgtcag cttccccgac                                                80

<210> SEQ ID NO 71
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 71
tccattaaca ctctgcttat agattgtaag ggtgattgca atgctttctg cataaaactt    60
tggttttctt gttaatcaat                                                80

<210> SEQ ID NO 72
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 72
attgattaac aagaaaacca aagttttatg cagaaagcat tgcaatcacc cttacaatct    60
ataagcagag tgttaatgga                                                80

<210> SEQ ID NO 73
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 73
agtaaaagga tttgtatatt agccttgcta agggagacat ctagtgatat aagtgtgaac    60
tacacttatc ttaaatgatg                                                80

<210> SEQ ID NO 74
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 74
catcatttaa gataagtgta gttcacactt atatcactag atgtctccct tagcaaggct    60
aatatacaaa tcctttact                                                 80

<210> SEQ ID NO 75
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 75
atatcactag atgtctccct                                                      20

<210> SEQ ID NO 76
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 76
tcgggtttat ttgtaaatta tccctaggga cctccgagca tagcgggagg catataaaag          60
ccaatagaca atggctagca                                                      80

<210> SEQ ID NO 77
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 77
tgctagccat tgtctattgg cttttatatg cctcccgcta tgctcggagg tccctaggga          60
taatttacaa ataaacccga                                                      80

<210> SEQ ID NO 78
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 78
ggcatcagcc tacaaatacc agtattcata ctgaaggcaa tgccctagca gataagcttg          60
ccacccaagg aagttatgta                                                      80

<210> SEQ ID NO 79
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 79
tacataactt ccttgggtgg caagcttatc tgctagggca ttgccttcag tatgaatact          60
ggtatttgta ggctgatgcc                                                      80

<210> SEQ ID NO 80
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 80
cgcaactgtt aaatctctca atgtactcac tagtattgca attccaaagg tgattcactc          60
tgatcaaggt gcagcattca                                                      80
```

<210> SEQ ID NO 81
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 81
tgaatgctgc accttgatca gagtgaatca cctttggaat tgcaatacta gtgagtacat    60
tgagagattt aacagttgcg                                                80

<210> SEQ ID NO 82
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 82
ctcgttcctg gtctcctgtt gttggccaat tggtccagga gagggtggct aggcctgctt    60 cttttgagacc tcgttggcat                                               80

<210> SEQ ID NO 83
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 83
atgccaacga ggtctcaaag aagcaggcct agccaccctc tcctggacca attggccaac    60
aacaggagac caggaacgag                                                80

<210> SEQ ID NO 84
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 84
tggtccagga gagggtggct                                                20

<210> SEQ ID NO 85
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 85
atgaggcact tcagaataca acaactgtga ctgaacagca gaaggaacaa attatactgg    60
acattcaaaa tgaagaagta                                                80

<210> SEQ ID NO 86
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 86
tacttcttca ttttgaatgt ccagtataat ttgttccttc tgctgttcag tcacagttgt    60
tgtattctga agtgcctcat                                                80

<210> SEQ ID NO 87
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 87
tgaacagcag aaggaacaaa                                                20

<210> SEQ ID NO 88
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 88
tatggaagct tatggacctc agagaggaag taacgaggag agggtgtggt ggaatgccac    60
tagaaaccag ggaaaacaag                                                80

<210> SEQ ID NO 89
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 89
cttgttttcc ctggtttcta gtggcattcc accacaccct ctcctcgtta cttcctctct    60
gaggtccata agcttccata                                                80

<210> SEQ ID NO 90
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 90
taacgaggag agggtgtggt                                                20

<210> SEQ ID NO 91
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 91
agtaaaagga tttgtatatt agccttgcta agggagacat ctagtgatat aagaggcttt    60
atatcttatc ttaaatgatg                                                80

<210> SEQ ID NO 92
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 92

```
catcatttaa gataagatat aaagcctctt atatcactag atgtctccct tagcaaggct    60
aatatacaaa tcctttact                                                 80
```

<210> SEQ ID NO 93
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 93

```
agtaaaagga tttgtatatt agccttgcta agggagacat caggctttat atctgtgaac    60
tacacttatc ttaaatgatg                                                80
```

<210> SEQ ID NO 94
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 94

```
catcatttaa gataagtgta gttcacagat ataaagcctg atgtctccct tagcaaggct    60
aatatacaaa tcctttact                                                 80
```

<210> SEQ ID NO 95
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 95

```
agtaaaagga tttgtatatt agccttgcta ggctttatat ctagtgatat aagtgtgaac    60
tacacttatc ttaaatgatg                                                80
```

<210> SEQ ID NO 96
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 96

```
catcatttaa gataagtgta gttcacactt atatcactag atataaagcc tagcaaggct    60
aatatacaaa tcctttact                                                 80
```

<210> SEQ ID NO 97
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 97

```
agtaaaagga tttgtatagg ctttatatca agggagacat ctagtgatat aagtgtgaac    60
tacacttatc ttaaatgatg                                                80
```

<210> SEQ ID NO 98
<211> LENGTH: 80
<212> TYPE: DNA
<213> ORGANISM: Artificial Sequence

```
<220> FEATURE:
<223> OTHER INFORMATION: Synthetic polynucleotide

<400> SEQUENCE: 98
catcatttaa gataagtgta gttcacactt atatcactag atgtctccct tgatataaag    60
cctatacaaa ccttttact                                                 80

<210> SEQ ID NO 99
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 99
agtaaaagga tttgtatatt agccttgcta agcacattcg atagtgatat aagaggcttt    60
atatcttatc ttaaatgatg                                                80

<210> SEQ ID NO 100
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 100
catcatttaa gataagatat aaagcctctt atatcactat cgaatgtgct tagcaaggct    60
aatatacaaa ccttttact                                                 80

<210> SEQ ID NO 101
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 101
agtaaaagga tttgtatatt agccttgcta agcacattcg aaggctttat atctgtgaac    60
tacacttatc ttaaatgatg                                                80

<210> SEQ ID NO 102
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 102
catcatttaa gataagtgta gttcacagat ataaagcctt cgaatgtgct tagcaaggct    60
aatatacaaa ccttttact                                                 80

<210> SEQ ID NO 103
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 103
cgagactctc caggtttggt aa                                             22

<210> SEQ ID NO 104
```

```
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 104
ggttctcgaa tcaagtcggt tt                                              22

<210> SEQ ID NO 105
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 105
aaccgacttg attcgagaac ct                                              22

<210> SEQ ID NO 106
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 106
gttgggcgcc aattgtcat                                                  19

<210> SEQ ID NO 107
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 107
actaaggctc cttctactag cg                                              22

<210> SEQ ID NO 108
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 108
gttgaagaag tgaatgctgc ac                                              22

<210> SEQ ID NO 109
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 109
ttataccatc catccacccc tc                                              22

<210> SEQ ID NO 110
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 110
```

```
gtttatgcca acgaggtctc aa                                            22

<210> SEQ ID NO 111
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 111
gcatgaggca cttcagaata ca                                            22

<210> SEQ ID NO 112
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 112
aggccaatac tcttgagcta gt                                            22

<210> SEQ ID NO 113
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 113
cccatcttgc tgacctcac                                                19

<210> SEQ ID NO 114
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 114
agacctggga cgtttctgtg                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 115
aaacctacag gtggggtctt                                               20

<210> SEQ ID NO 116
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 116
ccccacctgt aggt                                                     14

<210> SEQ ID NO 117
<211> LENGTH: 20
<212> TYPE: DNA
```

```
<213> ORGANISM: Artificial Sequence
<220> FEATURE:
<223> OTHER INFORMATION: Synthetic polynucleotide

<400> SEQUENCE: 117
aaacctacag gtggggtctt                                               20

<210> SEQ ID NO 118
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 118
ccccacctgt aggt                                                     14

<210> SEQ ID NO 119
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 119 ttcccctgg cctt                                                      14

<210> SEQ ID NO 120
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 120
ctcctcctcc aggt                                                     14

<210> SEQ ID NO 121
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 121
tccccaggag ctgttgatcc                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 122
atatcactag atgtctccct                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 123
atatcactag atgtctccct                                               20
```

<210> SEQ ID NO 124
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 124
atatcactag atgtctccc                                            19

<210> SEQ ID NO 125
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 125
agacatctag tgat                                                 14

<210> SEQ ID NO 126
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 126
tggtccagga gagggtggct                                           20

<210> SEQ ID NO 127
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 127
ggtccaggag agggtggcta                                           20

<210> SEQ ID NO 128
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 128
ggtccaggag agggtggct                                            19

<210> SEQ ID NO 129
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 129
ggtccaggag agggtggcta                                           20

<210> SEQ ID NO 130
<211> LENGTH: 14
<212> TYPE: DNA
<213> ORGANISM: Artificial Sequence
<220> FEATURE:

<223> OTHER INFORMATION: Synthetic polynucleotide

<400> SEQUENCE: 130
caccctctcc tgga                                                                14

<210> SEQ ID NO 131
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 131
tgaacagcag aaggaacaa                                                           19

<210> SEQ ID NO 132
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 132
tgaacagcag aaggaacaaa                                                          20

<210> SEQ ID NO 133
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 133
tgaacagcag aaggaacaaa                                                          20

<210> SEQ ID NO 134
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 134
ttccttctgc tgtt                                                                14

<210> SEQ ID NO 135
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 135
taacgaggag agggtgtggt                                                          20

<210> SEQ ID NO 136
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 136
caccctctcc tcgt                                                                14

```
<210> SEQ ID NO 137
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 137
atatcactag atgtctccct                                              20

<210> SEQ ID NO 138
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 138
atatcactag atgtctccct                                              20

<210> SEQ ID NO 139
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 139
atatcactag atgtctccc                                               19

<210> SEQ ID NO 140
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 140
agacatctag tgat                                                    14

<210> SEQ ID NO 141
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 141
atatcactag atgtctccct                                              20

<210> SEQ ID NO 142
<211> LENGTH: 79
<212> TYPE: DNA
<213> ORGANISM: Artificial Sequence
<220> FEATURE:
<223> OTHER INFORMATION: Synthetic polynucleotide

<400> SEQUENCE: 142
caagcgtaaa ttgcatagtc gtgaagtcag ggcttctaag gtatctatca ccagattgat   60
atctattggt atctatcac                                               79

<210> SEQ ID NO 143
<211> LENGTH: 79
<212> TYPE: DNA
<213> ORGANISM: Artificial Sequence
<220> FEATURE:
```

```
<223> OTHER INFORMATION: Synthetic polynucleotide

<400> SEQUENCE: 143
gttcgcattt aacgtatcag cacttcagtc ccgaagattc catagatagt ggtctaacta      60
tagataacca tagatagtg                                                   79

<210> SEQ ID NO 144
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 144
tatatcacta                                                             10

<210> SEQ ID NO 145
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 145
gatgtctccc                                                             10

<210> SEQ ID NO 146
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 146
tggccaaatc catagcctta ga                                               22

<210> SEQ ID NO 147
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 147
gtctctcgca gccacatggg                                                  20
```

STRONG INSULATOR AND USES THEREOF IN GENE DELIVERY

CROSS-REFERENCE TO RELATED APPLICATIONS

This application is a National Stage Application under 35 U.S.C. § 371 of International Application No. PCT/US2018/051590, filed Sep. 18, 2018, which claims the benefit under 35 U.S.C. § 119(e) of the filing date of U.S. provisional application No. 62/559,751, filed Sep. 18, 2017, the contents of each of which are incorporated by reference herein in its entirety.

INCORPORATION OF SEQUENCE LISTING

A computer readable text file, entitled "Sequence-Listing-103144-645355-70030US01.txt" created on or about Mar. 16, 2020, with a file size of about 37,000 bytes, contains the sequence listing for this application and is hereby incorporated by reference in its entirety.

BACKGROUND OF THE INVENTION

Retroviral vectors (RV) have become valuable tools in gene therapy because of their ability to enter human host cells and integrate genes of interest, particularly difficult-to-deliver DNAs, into host cells for stable gene transfer and expression. Retroviral vectors have effectively been used for the delivery and integration of therapeutic transgenes. To date, several genetic diseases have successfully been treated using this approach, for example, X-linked severe combined immunodeficiency (X-SCID), chronic granulomatous disease (CGD), adenine deaminase deficiency (ADA-SCID), and Wiskott-Aldrich syndrome (WAS) (Hacein-Bey-Abina et al., *N. Engl. J. Med.* 363:355-64, 2010; Hacein-Bey-Abina et al., *J. Clin. Invest.* 118:3132-42, 2008, Howe et al., *J. Clin. Invest.* 118:3143-50, 2008, Stein et al., *Nat. Med.* 16:198-204, 2010, Ott et al., *Nature Medicine* 12:401-9, 2006, Bortug et al., *N. Engl. J. Med.* 363:1918-27, 2010).

One major challenge in retroviral therapies is a high risk of enhancer-mediated genotoxicity or insertional oncogenesis. Retroviral vectors, such as gammaretroviral (GV) vector and lentiviral (LV) vector, have strong enhancers in the U3 region of their long terminal repeat (LTR), which can cause proto-oncogene activation as a consequence of non-random integrations near transcriptional start sites of proto-oncogenes in the host cells. This is also referred to as to as insertional activation (Maruggi et al., *Mol. Ther.* 17:851-6, 2009). Self-inactivating (SIN) GV and LV vectors with a 3'LTR U3 enhancer/promoter deletion and internal, weaker cellular/endogenous gene promoters driving transgene expression have been used to circumvent the risk of insertional oncogenesis by viral enhancers. However, the tradeoff is insufficient transgene expression for effective transgenic treatment or phenotypic correction.

It is therefore of great interest to develop new approaches to reduce genotoxicity of retroviral vectors for use in delivering genes of interests to host cells.

SUMMARY OF THE INVENTION

The present disclosure is based, at least in part, on the discovery of a strong insulator fragment from the long terminal report (LTR) of a foamy virus (FV), which substantially reduces genotoxicity when inserted into the LTR region of retroviral vectors.

Accordingly, one aspect of the present disclosure provides a nucleic acid construct for gene delivery, the nucleic acid construct comprises at least one gene of interest (GOI) flanked by an insulator fragment, wherein the insulator fragment comprises a nucleotide sequence at least 90% (e.g., at least 95%) identical to AAGGGAGACATCTAGTGA-TATAAGTGTGAA CTACAC (SEQ ID NO: 2) or the complementary sequence thereof (GTGTAGTTCACA CTTATATCACTAGATGTCTCCCTT; SEQ ID NO: 1). In some embodiments, the insulator fragment is heterologous to at least one fragment of the nucleic acid construct.

In some embodiments, the insulator fragment may comprise the nucleotide sequence of SEQ ID NO: 2 of the complementary sequence thereof. For example, the insulator fragment may comprise a single copy of SEQ ID NO: 2 or the complementary sequence thereof; or multiple copies of SEQ ID NO: 2 or the complementary sequence thereof.

The GOI may encode an agent of interest, which can be a protein or a nucleic acid. In some embodiments, the agent of interest is a therapeutic protein. Examples include, but are not limited to, an antibody, a growth factor, a cytokine, a coagulation factor, an enzyme, or a hemoglobin. In other embodiments, the agent of interest can be a nucleic acid. Examples include, but are not limited to an interfering RNA, an anti-sense oligonucleotide, or a microRNA.

In some embodiments, the insulator fragment can be located upstream to the GOI or downstream to the GOI. In other embodiments, the nucleic acid construct described herein may comprise at least two copies of the insulator fragment. One copy of the insulator can be located upstream to the GOI, and the other copy can be located downstream to the GOI. In some examples, the nucleic acid construct may comprise two GOIs, and at least one insulator fragment is located between the two GOIs.

In some embodiments, the nucleic acid construct described herein can be a vector, for example, a viral vector (e.g., a retroviral vector, an adenoviral vector, or an adeno-associated viral vector). In some instances, the viral vector is a self-inactivated (SIN) viral vector.

In some examples, the vector is a retroviral vector (e.g., a lentiviral vector or a gammretroviral vector), which may comprise a 5' long terminal repeat (LTR) and a 3'LTR. The insulator fragment can be located inside the 5' LTR, inside the 3'LTR, or inside both the 5' LTR and 3' LTR. In some instances, the insulator is heterologous to the 5' LTR and/or the 3'LTR. Exemplary retroviral vectors include, but are not limited to, a human immunodeficiency viral (HIV) vector, an avian leucosis viral (ALV) vector, a murine leukemia viral (MLV) vector, a murine mammary tumor viral (MMTV) vector, a murine stem cell virus, or human T-cell leukemia viral (HTLV) vector. In some instances, any of the retroviral vectors described herein may comprise multiple copies of the insulator fragment, at least one of which is located inside either the 5' LTR or the 3' LTR and at least one of which is located adjacent to the GOI, either upstream or downstream.

Any of the retroviral vectors described herein may comprise a 3'LTR that comprises an upstream polyadenylation (polyA) enhancer signal sequence, for example, an upstream sequence element (USE) derived from an SV40 late polyA signal sequence. In some examples, the upstream polyA enhancer signal sequence may replace a U3 region in the 3' LTR. Alternatively or in addition, the retroviral vector disclosed herein may further comprise one or more of the following elements:
(i) a psi (w) packaging signal;
(ii) a rev response element (RRE);
(iii) a gag element;

(iv) an env splice acceptor sequence;
(v) one or more copies of a heterologous polyA signal sequence downstream from the 3' LTR;
(vi) one or more chromatin insulator elements (e.g., chicken hypersensitive site-4 elements (cHS4));
(vii) a central polypurine tract (cPPT); and
(viii) a post-transcriptional regulatory element (PRE), such as a woodchuck hepatitis virus PRE.

In other embodiments, the nucleic acid construct can be a gene target construct for use in gene editing.

In another aspect, provided herein is a method for delivering an agent of interest to host cells, the method comprising contacting host cells with an effective amount of any of the nucleic acid constructs described herein. Also provided herein is a method for delivering an agent of interest to a subject, the method comprising administering to a subject in need thereof a viral particle comprising a genetic material produced from a retroviral vector as described herein.

Further, the instant application provides a method for integrating an exogenous gene into the genome of host cells, the method comprising (i) delivering an DNA endonuclease and a gene targeting construct as described herein into host cells, and (ii) incubating the host cells under conditions allowing for cleavage at a site of a chromosome of the host cells and integration of the gene targeting construct into the chromosome. Exemplary DNA endonucleases for use in the method described herein include, but are not limited to, a CRISPR associated RNA-guided endonuclease, a zinc-finger nuclease, a transcription activator-like effector nuclease (TALEN), or a meganuclease. In some embodiments, the gene targeting construct may comprise homologous arms flanking the gene(s) of interest and the insulator fragment. The homologous arms are homologous to the cleavage site of the chromosome.

Any of the methods described herein can be performed by administering the nucleic acid construct or the gene targeting construct to a subject in need thereof. In some embodiments, the subject is a human patient.

In yet another aspect, the present disclosure provides a method for reducing genotoxicity of a vector, the method comprising: (a) providing a vector comprising a gene of interest (GOI) or a site for cloning the GOI; and (b) inserting any of the insulator fragments described herein flanking the GOI or the site for cloning the GOI. The insulator fragment can be heterologous to at least one segment of the vector. In some instances, the insulator fragment comprises multiple copies of SEQ ID NO: 2 or the complementary sequence thereof. In some embodiments, the vector can be a viral vector, for example, a retroviral vector, an adenoviral vector, or an adeno-associated viral vector, such as those described herein. The insulator fragment can be located inside the vector at locations also described herein.

In some embodiments, step (b) of the method described herein can be performed by inserting multiple copies of the insulator fragment into a retroviral vector, at least one of which is inserted adjacent to the GOI or the site for cloning the GOI, either upstream or downstream, and at least one of which is inserted inside the 5'LTR or the 3' LTR.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings:

FIG. 1A: a schematic representation of the proviral forms of the vectors, including, from top to bottom, (i) a spleen focus-forming virus (SFFV, also abbreviated as SF) long terminal repeat (LTR) driven gammaretroviral (GV) vector, RSF91.eGFP.pre (SFFV-GV), which contains a U3 LTR region containing the promoter/enhancer elements of the SFFV and driving expression of eGFP cDNA; (ii) a SIN lentiviral (LV) vector, RRL.ppt.SFFV.eGFP.pre (SFFV-LV), which has a 400-bp LTR deletion and is driven by the enhancer-promoter elements from the SFFV U3 LTR region placed internally, upstream of eGFP; (iii) a SIN foamy virus vector (SFFV-FV), ΔΦSF.eGFP, which is driven by the enhancer-promoter elements from the SFFV U3 LTR region placed internally, upstream of eGFP, (iv) a murine stem cell virus (MSCV) LTR driven GV, MSCV.eGFP.pre (MSCV-GV), which contains a U3 LTR region containing the promoter/enhancer elements of the MSCV and driving expression of eGFP cDNA; (v) a SIN LV vector, RRL.ppt.MSCV.eGFP.pre (MSCV-LV), which is driven by an internal MSCV promoter/enhancer element from the MSCV U3 LTR region placed internally, upstream of eGFP; (vi) a SIN FV vector, ΔΦMSCV.eGFP (MSCV-FV), which is driven by the enhancer-promoter elements from the MSCV U3 LTR region placed internally, upstream of eGFP; and (vii) a promoterless foamy viral vector, ΔΦ.eGFP (Pr. Less-FV). ΔΦ series of vectors represent FV vectors with a 582-bp LTR deletion, and that are driven by the internal enhancer-promoter elements derived from SFFV and MSCV. All vectors encode the eGFP cDNA. The woodchuck hepatitis virus post-transcriptional regulatory element (wPRE) is present downstream of eGFP for all vectors except the MSCV-LV vector (RRL.ppt.MSCV.eGFP.pre). Δ represents an LTR with U3 deletion. The filled (black) box and empty (white) box represent the R and U5 region in an LTR, respectively. FIGS. 1B-1C: diagrams showing formation of immortalized clones (replating frequency) assessed at 2 and 5 weeks. The x axis represents replating frequency at 2 weeks (left panel) and 5 weeks (right panel) normalized to vector copy number (VCN). The y axis represents vectors tested using the in vitro immortalization (IVIM) assay. The immortalization potential of SFFV-FV (FIG. 1B) and MSCV-FV (FIG. 1C) were compared to that of SFFV-GV. The replating frequency of SFFV-LV (FIG. 1B) and MSCV-LV (FIG. 1C) were also compared to SFFV-GV. Median is indicated by the black line. Statistical significance between vector backbones is indicated by p values. *** denotes p<0.001.

FIG. 2A: a schematic illustration showing an exemplary outline of CRISPR/Cas9 insertion of the proviral sequences into the LMO2 gene. "HDR" denotes homology-directed repair. FIG. 2B: a diagram showing exemplary gRNA target sequences that target the LMO2 locus near the insertion site clinically found to be associated with insertional LMO2 transactivation and leukemogenesis, including gRNA1 (SEQ ID NO: 34), gRNA2 (SEQ ID NO: 37), gRNA3 (SEQ ID NO: 40), gRNA4 (SEQ ID NO: 43), and gRNA5 (SEQ ID NO: 46). Insertion of proviral sequences occurs at the location noted by the arrow. FIG. 2C: a diagram showing exemplary plasmid constructs as donor templates for homologous recombination (HR) for inserting GV, LV, and FV vector sequences into the LMO2 gene at this locus. Viral sequences are flanked by homology arms (HA) corresponding to the region on either side of the insertion site. Each HA tag is ~600-bp in length. All three vectors, as indicated, utilize the SFFV promoter/enhancer and encode an eGFP cDNA. Δ represents an LTR with U3 deletion. The filled (black) box and empty (white) box represent the R and U5 region in an LTR, respectively.

FIG. 3A: a diagram showing the editing efficiency of HeLa cells assessed by GFP expression at 2 weeks post transfection. GFP positive cells were sorted into single cells to establish clones. FIG. 3B: a schematic illustration showing two exemplary PCR reactions performed on HeLa cell clones to detect homology directed repair. FIG. 3C: a photo showing PCR 1 amplicon, which bridges across the 5' homology arm (HA). FIG. 3D: a photo showing PCR 2 amplicon that bridges across the 3' HA.

FIG. 4A: a chart showing the Hs001534473_m1 primer/probe set and GAPDH endogenous control. N=8 GV, 9 LV, and 11 FV clones. FIG. 4B: a chart showing the Hs001534473_m1 primer/probe set and PPIA endogenous control. N=7 GV, 8 LV, and 8 FV clones. FIG. 4C: a chart showing the Hs00277106_m1 primer/probe set and GAPDH endogenous control. N=8 GV, 9 LV, and 11 FV clones. FIG. 4D: a chart showing the Hs00277106_m1 primer/probe set and PPIA endogenous control. N=7 GV, 8 LV, and 8 FV clones.

FIG. 6A: a schematic illustration showing the proviral sequences of GV, LV, and FV (except SFFV, eGFP and wPRE sequences) that were analyzed in silico for potential CTCF binding motifs. The approximate locations of predicted binding motifs are indicated with stars above construct. FIG. 6B: a chart showing the position weight matrix (PWM) scores for the predicted CTCF binding motifs.

FIGS. 7A-7E include diagrams showing CTCF binding of the FV proviral sequence. FIG. 7A: a photo showing the CTCF-Chromatin Immunoprecipitation (CTFC-ChIP) of the FV clone (FV A2) followed by qualitative PCR, which was performed to interrogate in-cell binding of CTCF to the predicted binding sites. FIG. 7B: a photo showing that the fluorescently labeled probes corresponding to predicted CTCF binding sites in FV and LV proviral sequences were allowed to bind recombinant CTCF protein and resolved by electrophoretic mobility assay (EMSA), demonstrating binding between the FV2 probe and CTCF. FIG. 7C: a photo showing the competitive binding assay between the FV2 probe and unlabeled H19 probe. H19 was provided at the indicated molar excess. FIG. 7D: a diagram showing the sequence of the FV2 probe (top) with predicted CTCF binding sites TGTAGTTCA, TATATCACTA (SEQ ID NO: 144), and GATGTCTCCC (SEQ ID NO: 145). Mutant FV2 probes (1-6) are listed, with mutated regions indicated by underlined text. FIG. 7E: a photo showing the EMSA utilizing mutant probes. The original FV2 probe was used as positive control.

FIG. 9A: a photo showing regions overlapping the targeted LMO2 loci, revealing 4 LMO2 alleles in HeLa control cells, as determined by a fluorescence in situ hybridization (FISH) assay FIG. 9B: a chart showing copy number analysis, which was performed across the insertion site of LMO2 (intron 1). The HeLa control sample is represented by the white bar. FIG. 9C: a photo showing PCR amplification of the region bridging the gRNA target site.

DETAILED DESCRIPTION OF THE INVENTION

Figure 1A:
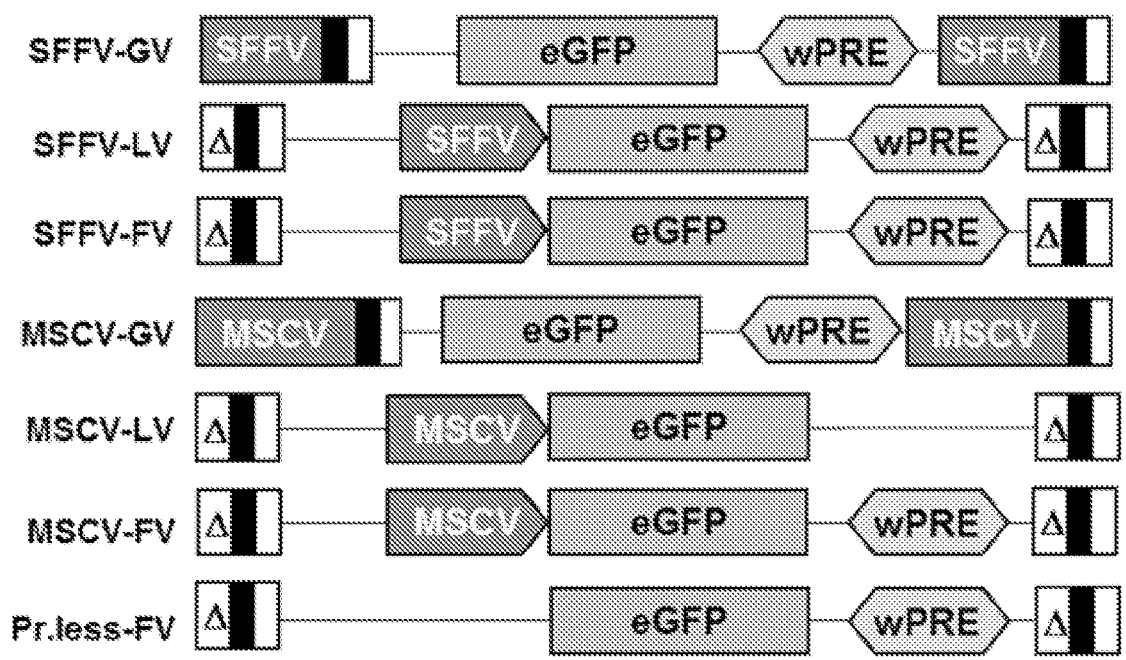
FIGS. 1A-1C include diagrams showing the immortalization frequency and replating efficiency of foamy virus (FV) vectors are significantly lower compared to lentivirus (LV) and gammaretrovirus (GV) vectors.

Understanding the genotoxic potential of viral vectors is important in designing safe and efficacious vectors for gene therapy. The present disclosure is based, at least in part, on an unexpected discovery of a unique insulator fragment, which, when inserted into a retroviral vector, significantly reduces the genotoxicity of the resultant retroviral vector. As used herein, the term "genotoxicity" refers to the property of retroviral vectors to cause damages in the genetic materials of a host cell to which the retroviral vector is introduced. Genotoxicity include insertional genotoxicity or enhancer-mediated genotoxicity, which may lead to cellular proto-oncogene activation (e.g., insertional oncogenesis), resulting in cancer development. In addition, the insulator fragment described herein, when placed flanking a transgene gene (either upstream or downstream), would be expected to reduce or eliminate the impact of a nearby gene on expression of the transgene, or vice versa.

Accordingly, provided herein are nucleic acid constructs (e.g., gene targeting constructs or vectors such as viral vectors) comprising a strong insulator fragment flanking a gene of interest (GOI). When inserted in a viral vector such as a retroviral vector (e.g., in the 5' LTR and/or 3' LTR), the insulator fragment could significantly reduce genotoxic potential of the viral vectors. Such viral vectors would be safe and effective tools for delivering genes of interest into host cells such that the therapeutic agents encoded by the GOIs could exert the desired therapeutic effects. Alternatively or in addition, when an insulator fragment is placed nearby a GOI to be inserted into the genome of a host cell, the insulator fragment could reduce or eliminate impact on the expression of the GOI due to nearby endogenous genes or reduce or eliminate impact on the expression of the nearby endogenous genes at the location where the GOI is inserted. In another example, when placed between two GOIs, the insulator could reduce or eliminate the impact on expression of one gene caused by the other one.

I. Insulator Fragments

The term "insulator fragment" as used herein refers to a type of cis-regulatory element (nucleotide fragment), which contains clustered binding sites for DNA-binding proteins (e.g., sequence-specific DNA-binding proteins) and mediate intra- and/or inter-chromosomal interactions. Insulators shield genes from inappropriate cis-regulatory signals (Ziebarth et al., *Nucleic Acids Res.* 41:D188-94, 2013) which, in the case of viral vectors, are the enhancer elements. Non-limiting examples of insulators include CCCTC-binding factor (CTCF) insulators, gypsy insulators, and β-globin loci.

The insulator fragment described herein may shield genes from inappropriate cis-regulatory signals. Thus, when placed between two genes, an insulator fragment may reduce or eliminate impact on the expression of one gene caused by the other gene. In addition, an insulator fragment described herein is capable of reducing genotoxicity of a gene transfer vector including such via any suitable mechanism, for example, by blocking the activity of an enhancer in a retroviral LTR. Besides enhancer blocking activity, an insulator may also reduce position effects, which means that an insulator will prevent surrounding chromatin from influencing integrated transgene expression or allowing silencing of the transgene by invasion of heterochromatin. Insulators have a dual function of preventing a) enhancers within vectors from activating surrounding cellular genes, and/or b) enhancers or repressors in the chromatin around the integrated vector to affect vector transgene expression. Insulators can also prevent spread of heterochromatin towards the vector. Heterochromatin is transcriptionally silent and would inactivate expression of the transgene carried by the vector.

The insulator fragment may function as an enhancer-blocker and/or a barrier. Enhancer blocking insulators are position-dependent, and typically function to block communication between regulatory elements. Enhancer blocking insulators are effective when placed between a promoter and an enhancer, and thus, prevent transcription induced by that enhancer (e.g., read-through transcription). Alternatively or in addition, the insulator can be an insulator, which prevents the silencing of genes by disruption of heterochromatin formation (West, Gaszner, and Felsenfeld, *Genes & Development*, 16(3): 271-88, 2002).

The insulator disclosed herein may comprise a nucleotide sequence at least 90% (e.g., at least 93%, at least 95%, at least 97%, at least 98%, at least 99%, or above) identical to identical to AAGGGAGACATCTAGTGATATAAGTGTGAACTACAC (SEQ ID NO: 2) or a complementary sequence thereof, e.g., GTGTAGTTCACA CTTATATCACTA GATGTCTCCCTT (SEQ ID NO:1). The "percent identity" of two nucleic acids is determined using the algorithm of Karlin and Altschul, *Proc. Natl. Acad. Sci.* USA 87:2264-68, 1990, modified as in Karlin and Altschul, Proc. *Natl. Acad. Sci.* USA 90:5873-77, 1993. Such an algorithm is incorporated into the NBLAST program (version 2.0) of Altschul et al., *J. Mol. Biol.* 215:403-10, 1990. BLAST nucleotide searches can be performed with the NBLAST program, score=100, wordlength-12 to obtain nucleotide sequences homologous to the nucleic acid molecules disclosed herein. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., NBLAST) can be used.

In some embodiments, the insulator fragment described herein comprises the nucleotide sequence of SEQ ID NO:2, or a complementary sequence thereof. Such an insulator fragment may contain one copy of SEQ ID NO:2 or a complementary sequence thereof, a functional variant thereof (e.g., sharing at least 90% sequence identity to SEQ ID NO:2 as described herein), or a complementary sequence thereof. Alternatively, it may contain multiple copies (e.g., 2, 3, 4, or 5 copies), each two of which may be linked directly in a tandem repeat format, or linked indirectly via a nucleic acid linker.

The insulator fragment described herein may have a maximum length of about 500 base-pairs (bps), for example, about 450 bps, about 400 bps, about 350 bps, about 300 bps, about 250 bps, about 200 bps, about 150 bps, about 100 bps, or about 50 bps. In one example, the insulator fragment described herein consists of SEQ ID NO:2 or a complementary sequence thereof. In general, the terms "about" and "approximately" mean within an acceptable error range for the particular value as determined by one of ordinary skill in the art. "About" can mean a range of less than ±30%, preferably less than ±20%, more preferably less than ±10%, more preferably less than ±5%, and more preferably still less than ±1% of a given value.

The insulators described herein may be capable of binding to CCCTC-binding factor (CTCF), which plays an important role in gene insulation and enhancer blocking (Schmidt et al., *Cell* 148:335-48, 2012), as well as providing chromatin barrier functions in vertebrates (Cuddapah et al., *Genome Res.* 19:24-32, 2009). CTCF binds to different DNA sequences via various combinations of 11 zinc fingers (Ziebarth et al., *Nucleic Acids Res.* 41:D188-94, 2013). In addition to its insulator and barrier functions, CTCF binding sites have been shown to reduce genotoxicity of viral vectors without diminishing viral titers (Liu et al., *Nat. Biotechnol.* 33:198-203, 2015). Without being bound by theory, the insulator fragment disclosed herein may provide a binding site for CTCF, which, upon binding to a retroviral vector at the insulator site, would act as an enhancer blocker, thereby reducing genotoxic potential of the retroviral vector. CTCF has been reported for controlling the activity of viral promoters in various types of viruses, including HPV and HTLV-1, Goodman et al., *J. Virology* 92(1): e01639-17, 2018, the relevant disclosures thereof are incorporated by reference for the purposes or subject matter referenced herein. Accordingly, the insulator fragment is expected to exhibit the intended insulator function in various types of retroviral vectors, such as those described herein.

The insulator fragment described herein may comprise one copy of a motif of SEQ ID NO:2, a functional variant thereof (e.g., share at least 90% sequence identity to SEQ ID NO:2 as described herein), or a complementary sequence thereof. Any of the insulator fragments disclosed herein is also within the scope of the present disclosure.

II. Nucleic Acid Construct Comprising the Insulator Fragment

Any of the insulator fragments disclosed herein may be used to make nucleic acid constructs, which may carry one or more genes of interest (GOI). Inclusion of the insulator fragment could shield the GOIs from inappropriate cis-regulatory signals, e.g., those located at the genome locus where the GOIs or a vector carrying such would be inserted, or shield local endogenous from cis-regulatory signals that control the expression of the GOIs. When the nucleic acid construct carries multiple GOIs, inclusion of an insulator fragment between two GOIs also could shield one from being influenced by the other.

Thus, also disclosed herein are nucleic acid constructs for the delivery of a transgene (gene of interest or GOI) carried by the nucleic acid constructs such that the expression of the transgene is not affected by nearby endogenous genes at the chromosome site where the transgene is to be inserted, or vice versa. When the nucleic acid construct contains multiple transgenes, placing an insulator fragment between two transgenes could also reduce or eliminate impact of the expression of one gene on the other.

The nucleic acid construct disclosed herein can be any type of nucleic acid molecules that comprises one or more GOIs and one or more insulator fragments flanking at least one GOI, e.g., upstream to the GOI or downstream to the GOI, or having one located upstream to the GOI and one located downstream to the GOI. The insulator fragment may be directly linked to the GOI. Alternatively, the insulator fragment may be linked to the GOI via a nucleic acid spacer. Such a nucleic acid spacer may range from 10 bps to 2 kbps, for example, 50 bps-2 kbps, 100 bp-1.5 kbps, 150 bps-1 kbps, 200 bps-500 bps, or 500 bps-1 kbps.

In some instances, the insulator fragment is located adjacent to a GOI, upstream and/or downstream to the GOI. The insulator fragment may be linked directly to the GOI or linked to the GOI via a short nucleic acid spacer, which may contain 5bp-200 bp, for example, 5-100 bps, 10-150 bps, 20-100 bps, 10-50 bps, 20-50 bps, or 20-30 bps.

The nucleic acid construct described herein may contain one GOI, which is flanked by one insulator fragment also disclosed herein either upstream or downstream to the GOI. Alternatively, the nucleic acid construct may contain two or more GOIs and an insulator fragment as described herein can be located between two GOIs. Such a nucleic acid construct may further contain additional insulator fragments flanking the GOIs, downstream and/or upstream.

In some embodiments, the nucleic acid construct disclosed herein can be a gene target construct, which can be to insert the GOI carried by the gene target construct via gene editing. A gene target construct may be a linear nucleic acid molecule, which may further comprise homologous arms at both the 5' and 3' ends of the whole construct or flanking the GOI. The homologous arms contain homologous sequences to a genome site where the gene target construct intends to insert so as to facilitate insertion of the gene target construct via homologous recombination. The gene target construct disclosed herein may contain multiple GOIs and one insulator fragment may be located between two GOIs.

In some embodiments, the nucleic acid construct disclosed herein can be a vector. A "vector" refers to a nucleic acid molecule capable of transporting another nucleic acid to which it has been linked. The vector can be capable of autonomous replication or integrate into the genome of a host cell. In some instances, the vector disclosed herein can be a viral vector, which contains elements derived from a viral genome (naturally-occurring or modified). Viral vectors can be used for the delivery of genetic materials (e.g., a transgene) into suitable host cells. Non-limiting examples of viral vectors include, but are not limited to, retroviral vectors (e.g., lentiviral vectors or gammaretroviral vectors), adenoviral vectors, adeno-associated viral vectors (AAV), and hybrid vectors (containing components from different viral genomes). Additional examples of viral vectors are provided in U.S. Pat. No. 5,698,443, U.S. Pat. No. 5,650,309, and U.S. Pat. No. 5,827,703, the relevant disclosures of each of which are herein incorporated by reference for the purpose and subject matter referenced herein.

In some examples, the nucleic acid construct disclosed herein is a retroviral vector. In some instances, at least one insulator fragment as disclosed herein can be inserted into the 5' LTR, the 3' LTR, or both in the retroviral vector to reduce genotoxicity of the retroviral vector. A retroviral vector is a DNA molecule containing proviral sequences (e.g., LTR sequences, Psi (ψ) sequence, and/or promoter/enhancer sequence) that can accommodate a gene of interest, to allow incorporation of both into target cells. The proviral sequences are derived from viral genome and are modified such that they can be used as a plasmid vehicle for carrying and transferring genetic materials. The proviral sequences are also modified to remove essential viral genes and safety concerns. Typically, a retroviral vector is incapable of self-proliferation and/or packaging to produce viral particles without presence of helper virus that provides essential viral proteins/genes.

The retroviral vector described herein comprises a 5' long terminal repeat (LTR), a 3'LTR, and any of the insulator fragments described herein, which may be inserted into one or both of the LTR regions. In addition, the retroviral vector may comprise additional viral or non-viral elements to facilitate the intended viral vector functionality as described herein.

The insulator fragment may be located inside the 5' LTR, 3'LTR or both the 5'LTR and 3'LTR in the retroviral vector described herein. The insulator fragment can be heterologous to the 5' LTR, the 3' LTR, or both, for example, when the retroviral vector is a foamy retroviral vector. The term "heterologous," as used herein, refers to two sequences derived from different viral species. In other words, the insulator sequence and one or both of the LTR sequences may not be derived from the same retroviral genome.

The LTR regions are typically located on opposite ends of a retroviral vector, which can be a linear DNA molecule. In some embodiments, the LTRs of the retroviral vector comprise a U3 region, a R region, and a U5 region. In some instances, the U3 region in the 5' LTR, the 3' LTR or both may comprise enhancer/promoter elements, which may drive the expression of genes within the retroviral vector. These enhancer/promoter elements may function as either an enhancer, a promoter, or both. Such retroviral vectors are often referred to as LTR-driven vectors (Maetzig et al., *Viruses* 3(6):677-713, 2011). In other instances, the 5' LTR, the 3' LTR, or both may have one or more of the U3 region, the R region, and the U5 region deleted (e.g., self-inactivated vectors such as those described below).

In some embodiments, the 3'-LTR may further comprise a polyadenylation (poly A) enhancer signal sequence, which is located upstream of the cleavage/polyadenylation (polyA) site (e.g., AAUAAA) and function to increase the polyA site efficiency and thus polyadenylation efficiency. Exemplary polyadenylation enhancer signal sequence includes upstream sequence element (USE) from a suitable viral gene, for example, simian virus 40 (SV40) late gene. The nucleotide sequence of an exemplary USE element for SV40 late gene is provided below:

(SEQ ID NO: 3)
TTTATTTGTGAAATTTGTGATGCTATTGCTTTATTTGTAAACCG.

Inclusion of such a polyA enhancer signal sequence may facilitate transcription termination and reduce read-through of vector transcript and improving packaging efficiency, which would lead to increased viral titer.

In addition to the insulator fragment and the LTRs described herein, the retroviral vectors also comprise components necessary for the basic functionality of the retroviral vector, for example, capable of being replicated, packed into viral particles, and/or capable of drive expression of genes of interest carried thereby in host cells. Such essential elements for constructing retroviral vectors are well known to those skilled in the art.

In some embodiments, the retroviral vectors described herein may comprise one or more of the following components: (i) a psi (ψ) packaging signal; (ii) a rev response element (RRE); (iii) a gag element; (iv) an env splice acceptor sequence; (v) one or more copies of a heterologous polyA signal sequence downstream from the 3' LTR; (vi) one or more chromatin insulator elements; (vii) a central polypurine tract (cPPT); and (viii) a post-transcriptional regulatory element (PRE).

A psi (ψ) packaging signal, also known as an encapsidation sequence, regulates the packaging of retroviral RNA into viral capsids during replication. It is typically placed downstream of 5' long terminal repeat in a retroviral vector to effectively package and deliver transgene carried by the retroviral vector. The nucleotide sequence for an exemplary ψ packaging signal is provided below:

(SEQ ID NO: 4)
TCGACGCAGGACTCGGCTTGCTGAAGCGCGCACGGCAAGAGGCGAGGGGC

GGCGACTGGTGAGTACGCCAAAAATTTTGACTAGCGGAGGCTAGAAGGAG

AGAGATGGGTGCGAGAGCGTCAGTATTAAGCGGGGGAGAA.

A rev response element (RRE) is a domain located in the env region. A RRE may have up to 360 nucleotides long within the 'env gene'. Rev protein binds to the RRE to regulate the expression of viral genes. The Rev/RRE system facilitates nuclear export of mRNAs. The nucleotide sequence for an exemplary RRE in the env gene is provided below:

(SEQ ID NO: 5)
GATCTTCAGACCTGGAGGAGGAGATATGAGGGACAATTGGAGAAGTGAAT

TATATAAATATAAAGTAGTAAAAATTGAACCATTAGGAGTAGCACCCACC

AAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAG

CGTCAATGACGCTGACGGTACAGGCCAGACAATTATTGTCTGGTATAGTG

CAGCAGCAGAACAATTTGCTGAGGGCTATTGAGGCGCAACAGCATCTGTT

GCAACTCACAGTCTGGGGCATCAAGCAGCTCCAGGCAAGAATCCTGGCTG

TGGAAAGATACCTAAAGGATCAACAGCTCCTGGGGATTTGGGGTTGCTCT

GGAAAACTCATTTGCACCACTGCTGTGCCTTGGAATGCTAGTTGGAGTAA

TAAATCTCTGGAACAGATTTGGAATCACACGACCTGGATGGAGTGGGACA

GAGAAATTAACAATTACACAAGCTTAATACACTCCTTAATTGAAGAATCG

CAAAACCAGCAAGAAAAGAATGAACAAGAATTATTGGAATTAGATAAATG

GGCAAGTTTGTGGAATTGGTTTAACATAACAAATTGGCTGTGGTATATAA

AATTATTCATAATGATAGTAGGAGGCTTGGTAGGTTTAAGAATAGTTTTT

GCTGTACTTTCTATAGTGAATAGAGTTAGGCAGGGATATTCACCATTATC

GTTTCAGACCCACCTCCCAACCCCGAGGGGACCCGACAGGCCCGAAGGAA

TAGAAGAAGAAGGTGGAGAGAGAGACAGAGACAGATCCATTCGATTAGTG

AACGGATC..

A gag (group-specific antigen) element encodes for the structural proteins (or a portion thereof) of a retrovirus, i.e., matrix, capsid and nucleocapsid components. In some instances, the retroviral vector described herein may contain a gag fragment that is the 5' fragment of a gag gene. Such a fragment may contain 250-650 bps (e.g., about 360 bps or 600 bps). Containing such a short gag fragment may enhance viral titer of retroviral vectors carrying a large gene of interest (for example, a globin gene). See, e.g., US20150316511, the relevant disclosures are incorporated by reference herein. In other instances, the retroviral vector described herein may be free of any gag fragment. The nucleotide sequence for an exemplary gag fragment is provided below:

(SEQ ID NO: 6)
ATGGGTGCGAGAGCGTCAGTATTAAGCGGGGGAGAATTAGATCGCGATGG

GAAAAAATTCGGTTAAGGCCAGGGGGAAAGAAAAAATATAAATTAAAACA

TATAGTATGGGCAAGCAGGGAGCTAGAACGATTCGCAGTTAATCCTGGCC

TGTTAGAAACATCAGAAGGCTGTAGACAAATACTGGGACAGCTACAACCA

TCCCTTCAGACAGGATCAGAAGAACTTAGATCATTATATAATACAGTAGC

AACCCTCTATTGTGTGCATCAAAGGATAGAGATAAAAGACACCAAGGAAG

CTTTAGACAAGATAGAGGAAGAGCAAAACAAAAGTAAGACCACCGCACAG

CAAGC.

An env splice acceptor sequence is a nucleotide sequence near the 3' end of the pol coding region in a retroviral genome. The splice acceptor sequence regulates the splicing of transcripts. It also enables the expression of the env coding region. The splice acceptor is highlighted in boldface and underlined in the env sequence below.

(SEQ ID NO: 5)
GATCTTCAGACCTGGAGGAGGAGATATGAGGGACAATTGGAGAAGTGAAT

TATATAAATATAAAGTAGTAAAAATTGAACCATTAGGAGTAGCACCCACC

AAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAG

CGTCAATGACGCTGACGGTACAGGCCAGACAATTATTGTCTGGTATAGTG

CAGCAGCAGAACAATTTGCTGAGGGCTATTGAGGCGCAACAGCATCTGTT

GCAACTCACAGTCTGGGGCATCAAGCAGCTCCAGGCAAGAATCCTGGCTG

TGGAAAGATACCTAAAGGATCAACAGCTCCTGGGGATTTGGGGTTGCTCT

GGAAAACTCATTTGCACCACTGCTGTGCCTTGGAATGCTAGTTGGAGTAA

TAAATCTCTGGAACAGATTTGGAATCACACGACCTGGATGGAGTGGGACA

GAGAAATTAACAATTACACAAGCTTAATACACTCCTTAATTGAAGAATCG

CAAAACCAGCAAGAAAAGAATGAACAAGAATTATTGGAATTAGATAAATG

GGCAAGTTTGTGGAATTGGTTTAACATAACAAATTGGCTGTGGTATATAA

AATTATTCATAATGATAGTAGGAGGCTTGGTAGGTTTAAGAATAGTTTTT

GCTGTACTTTCTATAGTGAATAGAGTTAGGCAGGGATATTCACCATTATC

GTTTCAGACCCACCTCCCAACCCCGAGGGGACCCGACAGGCCCGAAGGAA

TAGAAGAAGAAGGTGGAGAGAGAGACAGAGACAGATCCATTCGATTAGTG

AACGGATC..

In some instances, the retroviral vector may comprise one or more heterologous polyA signaling sites, which may be located downstream from the 3' LTR. Such heterologous polyA signaling sites may not be of a viral origin (e.g., from a non-viral gene such as a β-globin gene). Alternatively, the heterologous polyA signaling sites may be derived from a viral gene which is from a different viral species as the retroviral vector that contains the heterologous polyA signaling sites. Inclusion of such heterologous polyA signaling sites may enhance polyadenylation efficiency, thereby further reducing read-through of vector transcript and improving packaging efficiency, which would lead to increased viral titer. The nucleotide sequence for an exemplary polyA signaling sequence from a bovine growth hormone gene is provided below:

(SEQ ID NO: 7)
CCATCTGTTGTTTGCCCCTCCCCCGTGCCTTCCTTGACCCTGGAAGGTGC

CACTCCCACTGTCCTTTCCTAATAAAATGAGGAAATTGCATCGCATTGTC

TGAGTAGGTGTCATTCTATTCTGGGGGGTGGGGTGGGGCAGGACAGCAAG

GGGGAGGATTGGGAAGACAATAGCAGGCATGCTGGGGATGCGGTGGGCTC

TATGG.

In some embodiments, the retroviral vector may include one or more chromatin insulator elements. Chromatin insulators are promoter or enhancer sequences that resist heterochromatin formation. In some embodiments, a chromatin insulator can be a fragment of about 1 kb in length that blocks transcriptional activation by enhancers. It may function as barrier elements, as described herein to, inter alia, prevent the spread of heterochromatin and silencing of genes, reduce chromatin position effects and have enhancer blocking activity. These properties are desirable for consistent predictable expression and safe transgene delivery with randomly integrating vectors. Insulated vectors have reduced chromatin position effects and, provide consistent, and therefore improved overall expression.

In some examples, the one or more chromatin insulator elements in the retroviral vector described herein may be chicken hypersensitive site-4 elements (cHS4), which is a chromatin insulator from the chicken β-globin locus control region. Arumugam et al., *PLoS ONE* 4(9): e6995, 2009. In some instances, one or more full-length chromatin insulators (about 1.2 kb) of hypersensitive site-4 (cHS4) from the chicken p-globin locus can be inserted in the 3'LTR to allow its duplication into the 5'LTR in gamma-retrovirus and lentivirus vectors. In other instances, a truncated cHS4 fragment comprising a ~250-bp core may be used in the retroviral vector described herein. Such a core fragment may be combined with a 3' ~400-bp fragment from the cHS4 element. In one example, a functional reduced-length insulator of about 650 base pairs, including the core sequence and the 3'-fragment, can be used in constructing the retroviral vector described herein. Such cHS4-derived insulator sequences are described in US20150316511, the relevant disclosures are incorporated by reference herein. The nucleotide sequence of an exemplary full-length cHS4 is provided below:

(SEQ ID NO: 8)
GAGCTCACGGGGACAGCCCCCCCCCAAAGCCCCCAGGGATGTAATTACGT

CCCTCCCCCGCTAGGGGCAGCAGCGAGCCGCCCGGGGCTCCGCTCCGGT

CCGGCGCTCCCCCCGCATCCCCGAGCCGGCAGCGTGCGGGGACAGCCCGG

GCACGGGGAAGGTGGCACGGGATCGCTTTCCTCTGAACGCTTCTCGCTGC

TCTTTGAGCCTGCAGACACCTGGGGGATACGGGGAAAAAGCTTTAGGCT

GAAAGAGAGATTTAGAATGACAGAATCATAGAACGGCCTGGGTTGCAAAG

GAGCACAGTGCTCATCCAGATCCAACCCCCTGCTATGTGCAGGGTCATCA

ACCAGCAGCCCAGGCTGCCCAGAGCCACATCCAGCCTGGCCTTGAATGCC

TGCAGGGATGGGGCATCCACAGCCTCCTTGGGCAACCTGTTCAGTGCGTC

ACCACCCTCTGGGGGAAAAACTGCCTCCTCATATCCAACCCAAACCTCCC

CTGTCTCAGTGTAAAGCCATTCCCCCTTGTCCTATCAAGGGGGAGTTTGC

TGTGACATTGTTGGTCTGGGGTGACACATGTTTGCCAATTCAGTGCATCA

CGGAGAGGCAGATCTTGGGGATAAGGAAGTGCAGGACAGCATGGACGTGG

GACATGCAGGTGTTGAGGGCTCTGGGACACTCTCCAAGTCACAGCGTTCA

GAACAGCCTTAAGGATAAGAAGATAGGATAGAAGGACAAAGAGCAAGTTA

AAACCCAGCATGGAGAGGAGCACAAAAAGGCCACAGACACTGCTGGTCCC

TGTGTCTGAGCCTGCATGTTTGATGGTGTCTGGATGCAAGCAGAAGGGGT

GGAAGAGCTTGCCTGGAGAGATACAGCTGGGTCAGTAGGACTGGGACAGG

CAGCTGGAGAATTGCCATGTAGATGTTCATACAATCGTCAAATCATGAAG

GCTGGAAAAGCCCTCCAAGATCCCCAAGACCAACCCCAACCCACCCACCG

TGCCCACTGGCCATGTCCCTCAGTGCCACATCCCCACAGTTCTTCATCAC

CTCCAGGGACGGTGACCCCCCCACCTCCGTGGGCAGCTGTGCCACTGCAG

CACCGCTCTTTGGAGAAGGTAAATCTTGCTAAATCCAGCCCGACCCTCCC

CTGGCACAACGTAAGGCCATTATCTCTCATCCAACTCCAGGACGGAGTCA

GTGAGAATATT

Below is the nucleotide sequence of a 250-bp core and the 3' ~400-bp fragments from the cHS4:

250-bp core:
(SEQ ID NO: 9)
GGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTC

CCCCCGCATCCCCGAGCCGGCAGCGTGCGGGGACAGCCCGGGCACGGGGA

AGGTGGCACGGGATCGCTTTCCTCTGAACGCTTCTCGCTGCTCTTTGAGC

CTGCAGACACCTGGGGGGATACGGGGAAAAAGCTTTAGGCTGAAAGAGAT

3' ~400-bp fragment:
(SEQ ID NO: 10)
CTGAGCCTGCATGTTTGATGGTGTCTGGATGCAAGCAGAAGGGGTGGAAG

AGCTTGCCTGGAGAGATACAGCTGGGTCAGTAGGACTGGGACAGGCAGCT

GGAGAATTGCCATGTAGATGTTCATACAATCGTCAAATCATGAAGGCTGG

AAAAGCCCTCCAAGATCCCCAAGACCAACCCCAACCCACCCACCGTGCCC

ACTGGCCATGTCCCTCAGTGCCACATCCCCACAGTTCTTCATCACCTCCA

GGGACGGTGACCCCCCCACCTCCGTGGGCAGCTGTGCCACTGCAGCACCG

CTCTTTGGAGAAGGTAAATCTTGCTAAATCCAGCCCGACCCTCCCCTGGC

ACAACGTAAGGCCATTATCTCTCATCCAACTCCAGGACGGAGTCAGTGAG

Non-limiting examples of other chromatin insulators include ArsI (derived from the sea urchin arylsulfatase gene locus), sns5 (derived from the sea urchin H2A early histone gene), Ankyrin-1 gene promoter element, and Drosophila gypsy element (Emery, *Human Gene Therapy* 22(6):761-74, 2011).

A central polypurine tract (cPPT) directs penetration of viral particles through the nuclear membrane. In retroviral replication, it functions as a primer for synthesis of plus-strand DNA. It has been shown to increase the transduction efficiency and transgene expression when incorporated into retroviral vectors. The nucleotide sequence for an exemplary cPPT is shown below:

```
                                              (SEQ ID NO: 11)
AAAAGAAAAGGGGGGA.
```

A post-transcriptional regulatory element (PRE) is a sequence that, when transcribed, enhances the expression of a transgene in a viral vector. It has been shown to increase the transduction efficiency and transgene expression when incorporated into retroviral vectors. The nucleotide sequence for an exemplary PRE is provided below:

```
                                              (SEQ ID NO: 12)
TCGACAATCAACCTCTGGATTACAAAATTTGTGAAAGATTGACTGGTATT

CTTAACTATGTTGCTCCTTTTACGCTATGTGGATACGCTGCTTTAATGCC

TTTGTATCATGCTATTGCTTCCCGTATGGCTTTCATTTTCTCCTCCTTGT

ATAAATCCTGGTTGCTGTCTCTTTATGAGGAGTTGTGGCCCGTTGTCAGG

CAACGTGGCGTGGTGTGCACTGTGTTTGCTGACGCAACCCCCACTGGTTG

GGGCATTGCCACCACCTGTCAGCTCCTTTCCGGGACTTTCGCTTTCCCCC

TCCCTATTGCCACGGCGGAACTCATCGCCGCCTGCCTTGCCCGCTGCTGG

ACAGGGGCTCGGCTGTTGGGCACTGACAATTCCGTGGTGTTGTCGGGGAA

GCTGACGTCCTTTCCATGGCTGCTCGCCTGTGTTGCCACCTGGATTCTGC

GCGGGACGTCCTTCTGCTACGTCCCTTCGGCCCTCAATCCAGCGGACCTT

CCTTCCCGCGGCCTGCTGCCGGCTCTGCGGCCTCTTCCGCGTCTTCGCCT

TCGCCCTCAGACGAGTCGGATCTCCCTTTGGGC
```

In some embodiments, the PRE used in the retroviral vector is a PRE from a Hepatitis B virus (HPRE) or a PRE from a Woodchuck Hepatitis virus (WPRE). In some embodiments, there is more than one PRE in the retroviral vector, and the more than one PRE can be HPRE, WPRE, or a mixture thereof. In one embodiment, the retroviral vector does not include a PRE.

The retroviral vectors described herein may further comprise additional functional elements as known in the art to address safety concerns and/or to improve vector functions, such as packaging efficiency and/or viral titer. Additional information may be found in US20150316511 and WO2015/117027, the relevant disclosures of each of which are herein incorporated by reference for the purpose and subject matter referenced herein.

The retroviral vectors described herein may comprise the viral elements such as those described herein from one or more suitable retroviruses, which are RNA viruses with a single strand positive-sense RNA molecule. Retroviruses comprise a reverse transcriptase enzyme and an integrase enzyme. Upon entry into a target cell, retroviruses utilize their reverse transcriptase to transcribe their RNA molecule into a DNA molecule. Subsequently, the integrase enzyme is used to integrate the DNA molecule into the host cell genome. Upon integration into the host cell genome, the sequence from the retrovirus is referred to as a provirus (e.g., proviral sequence or provirus sequence). This efficient gene transfer mechanism has made retroviral vectors highly valuable tools in gene therapy, because they can be used for long term transgene expression in host cells.

Retroviruses include 7 families: alpharetrovirus (Avian leucosis virus), betaretrovirus (Mouse mammary tumor virus), gammaretrovirus (Murine leukemia virus), deltaretrovirus (Bovine leukemia virus), epsilonretrovirus (Walleye dermal sarcoma virus), lentivirus (Human immunodeficiency virus 1), and spumavirus (Human spumavirus). Six additional examples of retroviruses are provided in U.S. Pat. No. 7,901,671. Viral elements, such as those described herein, from a suitable retrovirus can be used to construct the retroviral vectors described herein. The retroviral vectors described herein may be a lentiviral vector or a gammaretroviral vector. Non-limiting examples of retroviral vectors include human immunodeficiency viral (HIV) vector, avian leucosis viral (ALV) vector, murine leukemia viral (MLV) vector, murine mammary tumor viral (MMTV) vector, murine stem cell virus, and human T-cell leukemia viral (HTLV) vector. These retroviral vectors comprise proviral sequences from the corresponding retrovirus.

The retroviral vectors described herein can be prepared by conventional recombinant technology. In some examples, an insulator fragment as those described herein may be inserted into a suitable location of a retroviral vector to reduce genotoxicity of the resultant retroviral vector. For example, the insulator fragment may be inserted inside the 5' LTR, inside the 3' LTR, or inside both the 5' LTR and the 3' LTR via conventional technology. When desired, additional insulator fragments can be inserted at suitable sites inside the retroviral vector, for example, adjacent to a transgene carried by the retroviral vector. As used herein, the term "inserting" refers to the process of adding a sequence of nucleotides to the retroviral vector by using, for example, restriction digestion and ligation or recombination. Techniques for inserting sequences into retroviral vectors would be apparent to those skilled in the art.

In some instances, the insulator fragment is inserted into a retroviral vector via the conventional cloning technology. Current Protocols in Molecular Biology, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., *Nature Methods* 6(5):343-345 (2009), the teachings of which relating to molecular cloning are herein incorporated by reference. Alternatively, insertion of the insulator fragment may be implemented by gene editing, e.g., by CRISPR.

In conventional gene therapy, self-inactivating (SIN) GV and LV vectors with a 3'LTR have been used increasingly to circumvent the risk of insertional oncogenesis by viral enhancers. These SIN GV and LV vectors have U3 enhancer/promoter deletion and internal, weaker cellular/endogenous gene promoters driving transgene expression. This deletes ubiquitously active enhancers in the U3 region of the long terminal repeats (LTR). These SIN 'LTR-less' or 'enhancer-less' vectors show reduced genotoxicity as compared to LTR-intact GV vectors in experimental systems both in vitro and in vivo (Modlich et al., *Blood* 108:2545-53, 2006, Zychlinski et al., *Mol. Ther.* 16:718-25, 2008, Montini et al., *J Clin Invest* 119:964-75, 2006). However, expression of the transgene is often not robust, and successful and complete correction of the disease phenotype is largely dependent on introduction of high numbers of transduction/vector copy number (VCN) per cell, except in diseases where modest levels of transgene expression are sufficient for correction.

In one embodiment of the present disclosure, the retroviral vector is a self-inactivating (SIN) retroviral vector. As used herein, a SIN vector is a retroviral vector that has had at least one of its U3 regions deleted. In one embodiment, the SIN vector has had the U3 region of its 5'LTR deleted. In an alternative embodiment, the SIN vector has had the U3 region of its 3'LTR deleted. In yet another embodiment, the SIN vector has had the U3 region in both its 5'LTR and 3'LTR deleted. As illustrated in FIG. 1A, some embodiments of the retroviral vector have an internal promoter region. In some embodiments said internal promoter region is operably linked to the GOI. In some embodiments, the internal promoter region is in a non-SIN vector. In some embodiments the internal promoter region is a U3 region that is either endogenous or heterologous. The term "endogenous," as used in the context of the internal promoter, refers to the internal promoter region being from the same retroviral vector or from the same species of retroviral vector. The term "heterologous," as used in the context of the internal promoter, refers to said internal promoter being from a different retroviral vector or different species of retroviral vector. In some embodiments the U3 region is substituted with a heterologous U3 region. In this particular embodiment, the term "heterologous" refers to the substituted U3 region being a different species from the R and/or U5 region of the retroviral vector.

Those of ordinary skill in the art would know that the distances of the insulator element from the promoter and the reporter gene in the constructs may vary depending upon the relative sizes of the GOI or the internal promoter used in the retroviral vector.

III. Applications of the Insulator Fragment for Effective Delivery of a Transgene Any of the nucleic acid constructs described herein may exert the insulator functions also described herein when introduced into host cells e.g., inserted into the genome of the host cells. Accordingly, provided herein are methods for delivering GOIs, which may encode agents of interest, into host cells, either in vitro or in vivo. The disclosed methods can apply in an experimental, veterinary, and medical context.

In some embodiments, any of the nucleic acid constructs described herein (e.g., gene target constructs or viral vectors such as retroviral vectors) is transfected into suitable host cells for producing viral particles. Techniques for transduction of nucleic acid construct into host cells such as into mammalian cells are well established in the art. Some examples are provided in U.S. Pat. No. 5,399,346. Methods of nucleic acid transfection are well established in the arts and range from chemical, to biological, and to physical methods. Chemical methods include, but are not limited to, calcium phosphate transfection, cationic polymer transfection, lipofection, FUGENE®, and DEAE-Dextran-mediated transfection. Other methods of transfection include, but are not limited to, electroporation, sonoporation, cell squeezing, impalefection, optical transfection, protoplast fusion, magnetofection™, and particle bombardment.

When the nucleic acid construct is a viral vector such as a retroviral vector, the host cells can be packaging cells that express viral structural and/or accessory proteins (e.g., retroviral structural and/or accessory proteins), for example, gag, pol, env, tat, rev, vif, vpr, vpu, vpx, and/or nef. Viral envelope proteins (env) determine the range of host cells to which the viral particles can infected and transform by recombinant retroviruses generated from the packaging cell lines. In the case of lentiviruses, such as HIV-1, HIV-2, SIV, FIV and EIV, the env proteins include gp41 and gp120. In some instances, a gene coding for the viral env proteins may be on a separate vector as those encoding for viral gag and pol. In other instances, genes coding for env, pol, and gag may be located on the same vector. Such vectors can be transfected into suitable host cells for stable expression of the viral proteins.

Packaging cells do not contain a packaging signal in its genetic materials and are capable of expressing (e.g., stably) viral structural proteins, replication enzymes (e.g., gag, pol, and env), as well as others that are necessary for the packaging of viral particles. Any suitable cell lines, for example, mammalian cell lines, can be employed to prepare packaging cells. Examples include CHO cells, BHK cells, MDCK cells, COS cells, VERO cells, 3T3 cells, NIH3T3 cells, HepG2 cells, HeLa cells, 293 cells, 293T cells, or A549 cells.

Methods of preparing viral stock solutions from packaging cells are known in the art and are illustrated by, e.g., Y. Soneoka et al., Nucl. Acids Res. 23:628-633, 1995 and N. R. Landau et al., J. Virol. 66:5110-5113, 1992. Infectious virus particles may be collected from the packaging cells using conventional techniques. For example, the infectious particles can be collected by cell lysis, or collection of the supernatant of the cell culture, as is known in the art. If needed, the collected virus particles may be purified using conventional technology.

The viral particles thus produced, which comprise RNA molecules transcribed from any of the retroviral vectors described herein, can be used to infect suitable host cells, thereby delivering the gene of interest carried by the retroviral vector. In some examples, the viral particles can be brought in contact with the host cells in cell culture for expressing an agent of interest encoded by the gene of interest in vitro. In other examples, the viral particles may be administered to a subject (e.g., a human subject) in need of the treatment via a suitable route (e.g., intravenous injection or local injection). In some examples, the viral particles can be administered to a subject in need of the treatment intravenously, intradermally, intraarterially, intralesionally, intratumorally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, or intraumbilically; or by other method or any combination of the forgoing as would be known to one of ordinary skill in the art (see, for example, Remington's Pharmaceutical Sciences (1990)).

Any of the nucleic acid constructs or viral particles carrying genetic materials derived from the nucleic acid constructs (e.g., RNA molecules transcribed from a retroviral vector) can be delivered to a subject in need of the treatment via a suitable route. In other embodiments, any of the nucleic acid constructs described herein can be used to manipulate cells in vitro or ex vivo, where the manipulated cells can be administered to the subject in need.

In some embodiments, the subject is a mammal. In some embodiments the subject is a human or human patient. In some embodiments, the subject is an animal (e.g., animal model). In other embodiments the subject is a mouse. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., rats, rabbits, etc.), and the like.

In some embodiments, the retroviral vectors disclosed herein are for use in delivering an agent of interest, which is encoded by the gene of interest included in the retroviral vector. Exemplary viral methods for delivery include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors, and adeno-associated virus (AAV) vectors (see, e.g., PCT Publication Nos. WO 94/12649, WO 93/03769; WO 93/19191; WO 94/28938; WO 95/11984 and WO 95/00655).

A GOI carried by a nucleic acid construct described herein may encode an agent of interest, which can be a therapeutic agent. When delivered to a subject, the GOI may express the agent of interest, which would exhibit therapeutic activities for treating a target disease or disorder in the subject. The therapeutic agent may be a therapeutic protein, for example, an antibody, a growth factor, a cytokine, a coagulation factor, an enzyme, or a hemoglobin.

Antibodies (also referred to as immunoglobulins) are large proteins that are produced in response to antigens and function primarily to neutralize pathogens. Non-limiting examples of antibodies of therapeutic interest can be found in US Patent Application No. 2011/0293705 A1.

Growth factors are proteins that regulate cell division, cell survival, and inflammation, among other cellular functions. Non-limiting examples of growth factors include Adrenomedullin (AM), Angiopoietin (Ang), Autocrine motility factor, Bone morphogenetic proteins (BMPs), Ciliary neurotrophic factor (CNTF), Leukemia inhibitory factor (LIF), Interleukin-6 (IL-6), Macrophage colony-stimulating factor (m-CSF), Granulocyte colony-stimulating factor (G-CSF), Granulocyte macrophage colony-stimulating factor (GM-CSF), Epidermal growth factor (EGF), Ephrin A1, Ephrin A2, Ephrin A3, Ephrin A4, Ephrin A5, Ephrin B1, Ephrin B2, Ephrin B3, Erythropoietin (EPO), Fibroblast growth factor 1(FGF1), Fibroblast growth factor 2(FGF2), Fibroblast growth factor 3(FGF3), Fibroblast growth factor 4(FGF4), Fibroblast growth factor 5(FGF5), Fibroblast growth factor 6(FGF6), Fibroblast growth factor 7(FGF7), Fibroblast growth factor 8(FGF8), Fibroblast growth factor 9(FGF9), Fibroblast growth factor 10(FGF10), Fibroblast growth factor 11(FGF11), Fibroblast growth factor 12(FGF12), Fibroblast growth factor 13(FGF13), Fibroblast growth factor 14(FGF14), Fibroblast growth factor 15(FGF15), Fibroblast growth factor 16(FGF16), Fibroblast growth factor 17(FGF17), Fibroblast growth factor 18(FGF18), Fibroblast growth factor 19(FGF19), Fibroblast growth factor 20(FGF20), Fibroblast growth factor 21(FGF21), Fibroblast growth factor 22(FGF22), Fibroblast growth factor 23(FGF23), Fetal Bovine Somatotrophin (FBS), Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factor-1 (IGF-1), Insulin-like growth factor-2 (IGF-2), Interleukin-1 (IL-1),IL-2,IL-3, IL-4, IL-5, IL-6, IL-7, Keratinocyte growth factor (KGF), Migration-stimulating factor (MSF), Macrophage-stimulating protein (MSP), Myostatin (GDF-8), Neuregulin 1 (NRG1), Neuregulin 2 (NRG2), Neuregulin 3 (NRG3), Neuregulin 4 (NRG4), Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS), T-cell growth factor (TCGF), Thrombopoietin (TPO), Transforming growth factor alpha (TGF-α), Transforming growth factor beta (TGF-β), Tumor necrosis factor-alpha (TNF-α), and Vascular endothelial growth factor (VEGF).

Cytokines are small molecules known to enhance the cellular immune response. Non-limiting examples of cytokines include TNFα, IFN-γ, IFN-α, TGF-β, IL-1, IL-2, IL-4, IL-10, IL-13, IL-17, IL-18, and chemokines. Non-limiting examples of chemokines include CCL14, CCL19, CCL20, CCL21, CCL25, CCL27, CXCL12, CXCL13, CXCL-8, CCL2, CCL3, CCL4, CCL5, CCL11, and CXCL10.

Coagulation factors regulate clotting. Non-limiting examples of coagulation factors include fibrinogen, prothrombin, tissue factor or tissue thromboplastin, IV (calcium), proaccelerin (labile factor), VI, stable factor (proconvertin), Antihemophilic factor A, Antihemophilic factor B or Christmas factor, Stuart-Prower factor, plasma thromboplastin antecedent, Hageman factor, fibrin-stabilizing factor, von Willebrand factor, prekallikrein (Fletcher factor), high-molecular-weight kininogen (HMWK) (Fitzgerald factor), fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), and cancer procoagulant.

Enzymes are polypeptides that function as biological catalysts. Non-limiting examples of therapeutic enzymes are provided in U.S. Pat. No. 7,807,618.

Hemoglobin is a protein found in red blood cells that functions as an oxygen-transport metalloprotein.

Genes that are of interest in the context of the present disclosure are provided in US Application No. 2011/0294114A1. In some embodiments, the gene encoding an agent of interest is β-globin or γ-globin, which can be used for treating anemia, e.g., sickle cell anemia or β-thalassemia.

In some embodiments, the agent of interest is a fluorescent protein (e.g., mCherry, eGFP, etc.). Non-limiting examples of fluorescent proteins include wt-GFP, green fluorescent protein (e.g, EGFP, Emerald, Superfolder GFP, Azami Green, mWasabi, TagGFP, TurboGFP, AcGFP, ZsGreen, T-Sapphire, etc.), blue fluorescent protein, (e.g., EBFP, EBFP2, Azurite, mTagBFP, etc), cyan fluorescent protein (e.g., ECFP, mECFP, Cerulean, mTurquoise, CyPet, AmCyan1, Midori-Ishi Cyan, TagCFP, mTFP1 (Teal), etc.), yellow fluorescent protein (e.g., EYFP, Topaz, Venus, mCitrine, YPet, TagYFP, PhiYFP, ZsYellow1, mBanana, etc.), orange fluorescent protein (e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, etc.), or red fluorescent protein (e.g., mRuby, mApple, mStrawberry, AsRed2, mRFP1, JRed, mCherry, HcRed1, mRaspberry, dKeima-Tandem, HcRed-Tandem, mPlum, AQ143, etc.).

In other embodiments, the agent of interest can be a nucleic acid. Examples include an interfering RNA (e.g., siRNA or shRNA), an anti-sense oligonucleotide, or a microRNA.

IV. Application of Insulator Fragment in Gene Editing

Any of the insulator fragment disclosed herein may also be used for insulation purposes in gene editing, e.g., those known in the art. For example, an insulator fragment can be in a gene targeting construct used in gene editing, flanking a gene to be integrated into a suitable chromosomal site in a host cell (either at one side or at both sides). In another example, a gene targeting construct used in gene editing may contain two or more genes to be inserted into the genome of a host cell and one or more insulator fragments may be inserted flanking the two or more genes. Such a gene targeting construct may be used in a suitable gene editing method, by which the gene target construct or a portion thereof can be integrated into the genome of a host cell, e.g., at a specific site. In some embodiments, the gene target construct may contain arms at both 5' and 3' ends that are homologous to the target site where the gene target construct is intended to integrate. The insulator fragment could function to insulate expression of the two or more genes carried by the gene target construct (e.g., expression of one gene has low or no impact on expression of another gene). Alternatively or in addition, the insulator fragment can also function to insulate one gene carried by the gene target construct and a nearby gene at the chromosomal site where the target gene construct or a portion thereof is integrated (e.g., expression of the target gene has low or no impact on expression of the nearby native gene or vice versa).

To perform the gene editing method described herein, a gene target construct as disclosed herein may be delivered to suitable host cells together with an endonuclease. The endonuclease can be a restriction endonuclease or DNA endonuclease, allowing site specific insertion of the gene targeting construct. DNA endonucleases and techniques for the targeted insertion of genes via gene editing are well known in the art. Non-limiting examples of DNA endonucleases include zinc finger nucleases, transcription activator-like effector nucleases (TALEN®), CRISPR/Cas-based RNA guided DNA endonucleases, and homing endonucleases (a.k.a., meganucleases). Examples of some of these endonucleases are provided in Gaj et el., *Trends Biotechnol.* 31(7): 397-405, 2013 and Certo and Morgan, *Molecular Therapy* 24(3):422-29, 2016, the relevant disclosures of each of which are herein incorporated by reference for the purpose and subject matter referenced herein.

In one example, the gene target construct described herein is used in a CRISPR method, which may involve a plasmid encoding a gRNA and a CRISPR nuclease such as cas9, and a gene target construct as a DNA template. The gRNA can be designed based on a desired target site where the target gene construct or a portion thereof is to be integrated. The gene target construct may be flanked by homology arms that would facilitate integration of the target gene construct by homology-directed repair (HDR) at the target site in the target cells. This CRISPR/Cas-based method described herein is a flexible, extremely efficient one-step process, where Cas9/gRNA plasmid and the template target gene construct can be transfected together, with derivation of clones within a short length of time (e.g., 2-3 weeks) following transfection, and easily implementable in a variety of cell types.

In some examples, the gene target construct may comprise proviral sequences and the CRISPR/Cas (e.g., CRISPR/Cas9)-based method described herein can be used to detect presence of viral vector sequences nearby a proto-oncogene of interest. Switching from one proto-oncogene to another would require only cloning of a donor plasmid with the provirus sequence flanked by relevant homology arms, and changing the gRNA sequence. Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Strong viral enhancers in γ-retrovirus vectors have caused cellular proto-oncogene activation and leukemia, necessitating use of cellular promoters in 'enhancer-less' self-inactivating integrating vectors. However, cellular promoters result in relatively low transgene expression, often leading to inadequate disease correction. Vectors derived from foamy virus, a nonpathogenic retrovirus, show higher preference for non-genic integrations than γ-retroviruses/lentiviruses and preferential integration near transcriptional start sites, like γ-retroviruses. Herein, the results found foamy virus vectors to be remarkably less genotoxic; well below what is expected from their integration site preferences. Further, the results found that strong viral enhancer/promoters placed in foamy viral vectors caused extremely low immortalization of primary mouse hematopoietic stem/progenitor cells compared to analogous γ-retrovirus/lentivirus vectors carrying the same enhancer/promoters; an effect not explained solely by foamy virus' modest insertional site preference for non-genic regions, compared to γ-retrovirus/lentivirus vectors. Using CRISPR/Cas9-mediated targeted insertion of analogous proviral sequences into the LMO2 gene and then measuring LMO2 expression, the results demonstrated a sequence specific effect of foamy virus, independent of insertional bias, contributing to reduced genotoxicity. These results showed that this effect is mediated by a 36-bp insulator located in the foamy virus long-terminal-repeat (LTR) regions that has high affinity binding for the CCCTC-binding factor (CTCF). Using an LMO2 activation assay, LMO2 expression was significantly increased when this insulator was removed from foamy virus, and significantly reduced when this insulator was inserted into the lentiviral LTR. These results elucidate a mechanism underlying the low genotoxicity of foamy virus, identify a novel, unique insulator, and support the use of foamy virus as a vector for gene therapy, especially when strong enhancer/promoters are required.

Materials And Methods

Vector design and production. The vectors SFFV-GV (RSF91.eGFP.pre) and SFFV-LV (RRL.ppt.SF.eGFP.pre) used in this disclosure have been described previously (Modlich et al., *Blood* 108:2545-53, 2006; Schambach et al., *Mol. Ther.* 13:391-400, 2006). The MSCV-GV eGFP.pre has been described (Bauer et al., *Blood* 108:3313-20, 2006). The MSCV-LV (RRL.ppt MSCV.eGFP.pre) is illustrated in FIG. 1A. A 388-bp region of the MSCV promoter (identical in sequence to the MSCV LTR promoter/enhancer in ΔΦMSCV CD18 (Bauer et al., *Nat. Med.* 14:93-7, 2008) was obtained through PCR amplification with artificial XhoI and AgeI ends, and then cloned into XhoI/AgeI restriction enzyme digested pRRLSIN.cPPT.PGK.eGFP.WPRE (Addgene, Cambridge, Mass.), to create pRRL.ppt.MSCV.eGFP-.pre (M. J. Hunter, D. D. Hickstein, unpublished results). All FV were in the ΔΦ backbone. The FV ΔΦMSCV.eGFP has been described (Trobridge et al., *Mol. Ther.* 6:321-8, 2002, Kiem et al., *Blood* 109:65-70, 2007). The SFFV promoter replaced the MSCV promoter in ΔΦMSCV.eGFP FV vector to create ΔΦSF.eGFP. All vectors encode eGFP cDNA. The promoterless FV was derived from the ΔΦMSCV.eGFP vector by removing the MSCV enhancer/promoter and religation.

Ecotropic GV supernatants were produced in 293T cells, by transient transfection as described in (Arumugam et al. 2009) and titers determined on NIH 3T3 fibroblast cells (American Type Culture Collection (ATCC)). Virus titers were in the range of $10^6$-$10^7$ infectious units/mL. The LV vectors SFFV-LV and MSCV-LV were produced by transient co-transfection of 293T cells (ATCC) as described in (Puthenveetil et al. 2004). The SFFV-FV, MSCV-FV, and Promoterless (Pr-less) FV were produced by four plasmid

[pCiES (Env), pCiGSΔΨ (Gag), pCiPs (Pol) and vector (pΔΦ)] transient transfection as described in (Trobridge et al., *Mol. Ther.* 6:321-8, 2002). The pCiGSΔΨ is the Gag expression cassette (Russell D W; unpublished) with a more complete deletion in the packaging signal. The pΔΦ is a deleted FV backbone with a polylinker to insert the transgene cassette.

FV were resuspended in Stemspan (Stem Cell Technologies, Vancouver, BC, Canada) containing 2% heat inactivated fetal bovine serum (FBS; Hyclone, Logan, Utah) and 5% DMSO (Sigma, St. Louis, Mo.) and was stored frozen in 5% DMSO until use. Titers of Pr-less FV were determined by measuring the genomic copy number of transduced HT1080 cells by quantitative real-time PCR (qRT-PCR) using primers that recognize wPRE while titers of the other vectors were determined by quantifying GFP expression by fluorescence-activated cell sorting (FACS). The titers of FV were in the range of $3 \times 10^7$ IU/ml to $1 \times 10^8$ IU/ml.

Isolation of lineage negative (Lin−) cells. Bone marrow from C57BL/6J mice was used for the isolation of Lin− cells using biotinylated lineage specific antibodies (Lineage cell depletion kit; BD Biosciences, San Jose, Calif.) using methods described in (Arumugam et al., *Mol. Ther.* 17:1929-37, 2009, Modlich et al., *Mol. Ther.* 17:1919-28, 2009). The biotin-labeled Lin− cells were incubated with Anti-Biotin Microbeads (Miltenyi Biotech) followed by magnetic sorting of unlabeled Lin− cells. Isolated Lin− cells were pre-stimulated for viral transductions in Stemspan medium (Stem Cell Technologies) containing 1% penicillin/streptomycin, 50 ng/ml mSCF, 100 ng/ml hIL-11 and 10 ng/ml mIL-3.

In vitro immortalization assay. Lin− cells were prestimulated overnight in Stemspan medium containing 1% penicillin/streptomycin, 50 ng/ml mSCF, 100 ng/ml hIL-11 and 10 ng/ml mIL-3. On day 2, 100 000 Lin− cells were used for each LV vector transduction. Lin− cells were transduced at a multiplicity of infection (MOI) of 20, twice at 8 hour intervals using concentrated LV vector supernatants. For GV transduction, lineage-negative cells were pre-stimulated for 2 days in Stemspan-cytokine cocktail. GV transductions were performed on day 3 and day 4 on RetroNectin recombinant human fibronectin fragment (Takara Bio Inc., Kusatsu, Shiga, Japan) coated 24 well dishes preloaded with retroviral vectors SFFV-GV and MSCV-GV at an MOI of 20. After the final transductions, transduced Lin− cells were washed and expanded as bulk cultures in a Stemspan-cytokine cocktail for 19 days.

FV stocks were rapidly thawed by adding warm pre-stimulation medium and Lin− cells were transduced once with FV in 48 well plates, pre-coated with RetroNectin recombinant human fibronectin fragment at a concentration of 8 μg/cm² at MOI 50. A higher MOI was chosen for transduction as foamy virus transductions were done only once compared to two transductions with lentiviral vectors. After 16 hours, cells were washed and expanded in the Stemspan-cytokine cocktail. The toxicity in Lin− cells (50-60% viability) following foamy viral vector transductions was observed, even at ≤1% DMSO final concentration during transduction. At day 4 after final transduction, transgene expression from transduced bulk cultures was analyzed using flow cytometry. In bulk cultures with lower gene transfer efficiency, GFP+ cells were sorted using BD FACS Aria II (BD Biosciences) and expanded until plated. Bulk cultures with higher gene transfer were also sorted for GFP+ cells and the replating frequency was compared between sorted pools and unsorted transduced pools. During expansion, transduced bulk cultures were maintained at a concentration of $2-5 \times 10^5$ cells/mL. After expansion, cells were plated in 96 well plates at a density of 100 cells/well. After 2 weeks of plating, the 96 well plates were examined and scored for the presence of wells with proliferating cell populations (positive/immortalized well). Under these conditions, the mock cells barely survive. Mock transductions were those without addition of virus and were negative controls for each experiment. A promoterless FV was also included as a negative control. The positive wells were further expanded for molecular analysis. At 5 weeks, some of the clones expanded at 2 weeks had terminally differentiated and died by 5 weeks. The replating frequency of each vector tested at 2 weeks and 5 weeks was calculated based on Poisson statistics using L-Calc software (Stem Cell Technologies). Replating frequency was normalized to the mean vector copy number (VCN) of the Lin− bulk culture population prior to replating.

Immortalized clones derived from SFFV-GV could be replated at the same frequency at 2 weeks and 5 weeks, allowing comparison of the relative genotoxicity of the vectors to the highly genotoxic SFFV-GV vector. In contrast, clones derived from vectors with low genotoxic potential showed initial growth and replating potential at 2 weeks, but terminally differentiated thereafter and lost their replating frequency by 5 weeks. To be able to compare immortalization frequency/VCN of sorted and unsorted populations, a portion of the transduced bulk cultures from SFFV-GV, MSCV-GV, SFFV-LV, MSCV-LV, SFFV-FV and MSCV-FV transduced Lin− cells were sorted for GFP expression, and showed proportional immortalization before and after sorting, validating this modification to give a similar immortalization readout. Immortalization frequencies/VCNs before sorting of SFFV-GV, SFFV-LV and SFFV-FV transduced cells were 0.001755, 0.000176, and 0.000006, respectively. After sorting, frequencies were 0.002016, 0.000128, and 0.000023, respectively. For the vector-transduced group negative for replating clones, calculations were based on the assumption that a replating clone would be detected if 97 wells were plated instead of 96 wells (Zychlinski et al., *Mol. Ther.* 16:718-25, 2008).

Phenotypic analysis of immortalized clones. Immortalized clones were labeled with antibodies that recognize cell surface markers Sca-1 PE (Clone D7, Cat #553108) and c-Kit APC (Clone 2B8, Cat #553356) from BD Biosciences, and analyzed using a Fluorescence Activated Cell Sorter (FACS) Canto (BD Biosciences).

Vector copy number analysis. Quantitative real-time PCR was performed to assess the gene transfer efficiency of GV, LV, and FV vector-transduced bulk cultures. For GV vectors, LV vectors, and FV vectors, primers which recognize the wPRE region were used to measure the VCN in bulk cultures. Genomic DNA from a single copy NIH 3T3 cell clone carrying a single copy of MM13 vector was used as a standard for copy number analysis. The MM13 plasmid has been described previously (Will et al., *Cell Cycle* 5:14-22, 2006). Primers in the FV backbone were used to measure copy number as well. FV backbone forward primer: 5'-AATCCTTTACATGGAGAAGTTATAGGTCTT-3' (SEQ ID NO: 13), reverse primer: 5'-TGGCCAAATCCAT-AGCCTTAGA-3' (SEQ ID NO: 146). PCR reaction was carried out with Taqman Probe: 5'-ATCTGAAATCTCT-CAATTTGTCCCCACCA-3' (SEQ ID NO: 14) with tetramethyl-6-carboxyrhodamine dye as quencher. The FV or the wPRE specific signal was normalized to mouse ApoB in each sample. Genomic DNA (50 ng) from a single copy murine erythroleukemia cell (MEL) clone transduced with FV was diluted with untransduced MEL DNA to generate copy number standards. Quantitative PCR was performed using Applied Biosystems 7900HT Real-Time PCR system (Thermo Fisher, Grand Island, N.Y.) using thermocycler protocol for 96 well plates according to manufacturer's instructions.

Ligation amplification mediated PCR to determine insertion sites in immortalized clones. For LAM-PCR, the junction sequences between the viral LTR and the mouse genome was linearly amplified twice with 100 ng of genomic DNA from FV immortalized clones using 0.25 pmol of the FV-specific 5' biotinylated primer [5'-GAACCTTGTGTCTCTCATCCC-3'] (SEQ ID NO: 15) and 2.5 units of Qiagen Taq polymerase (Qiagen, Hilden, Germany), with cycling conditions of initial denaturation at 95° C. for 3 min, 50 cycles of amplification (95° C. for 30 sec, 55° C. for 30 sec, 72° C. for 1 min), and a final extension at 72° C. for 3 min. After DNA enrichment of the biotinylated DNA, hexanucleotide primer extension was carried out using Klenow (Promega, Madison, Wis.) and the primer extended product was digested with TasI [New England Biolabs (NEB), Ipswich, MA]. Following TasI digestion, the DNA was ligated to TasI specific double stranded linkers 5'-GACCCGGGAGATCTGAAT-TCAGTGGCACAGCAGTTAGG-3' (SEQ ID NO: 16)/5'-AATTCCTAACTGCTGTGCCACTGAATTCAGATC-3' (SEQ ID NO: 17). The first exponential amplification of linked products was performed using 12.5 pmol each of FV-specific primer [5'-GTCTATGAGGAGCAGGAGTA-3'] (SEQ ID NO: 18) and linker cassette-specific primer [5'-GACCCGGGAGATCTGAATTC-3'] (SEQ ID NO: 19). Eight percent of the first exponential PCR reaction was then used as template for a second exponential nested PCR amplification using 12.5 pmol each of nested FV-specific primer [5'-CCTCCTTCCCTGTAATACTC-3'] (SEQ ID NO: 20) and nested linker cassette-specific primer [5'-AGTGGCACAGCAGTTAGG-3'] (SEQ ID NO: 21) using the same conditions as the first PCR. To detect the insertion sites from the MSCV GV immortalized clones, 100 ng of genomic DNA was linear-amplified using MSCV LTR specific 5'-biotinylated primer (LTR1): 5'-CTGGGGAC-CATCTGTTCTTGGCCCT-3' (SEQ ID NO: 22), enriched with Dynabeads M-280 streptavidin (Thermo Fisher), digested with Tsp509I (NEB) and was linked to an asymmetric linker cassette (5'-AATTCTCTAGTATGC-TACTCGCACCG ATTATCTCCGCTGTCAGT-3' (SEQ ID NO: 23) and 5'-ACTGACAGCGGAGATAA TCGGTGCGAGTAGCATACTAGAG-3' (SEQ ID NO: 24)). Ligation products were then amplified with LTR and linker specific primers LTR2 (5'-GACTTGTGGTCTCGCTGTTC CTTGG-3') (SEQ ID NO: 25) and a linker cassette primer LC1 (5'-ACTGACAGCG-GAG ATAATCG-3') (SEQ ID NO: 26) ($1^{st}$ exponential PCR). The second exponential PCR was carried out with primers LTR3: (5'-GGTCTCCTCTGAGTGATTGAC-TACC-3') (SEQ ID NO: 27) and LC2: (5'-GTGCGAGTAG-CATACTAGAG-3') (SEQ ID NO: 28) (Shou et al., *Proc. of the Nat. Acad. of Sci.* 103:11730-11735, 2006).

Next Generation Sequencing of Ligation Amplification Mediated (LAM) PCR Products.

The products from the second exponential PCR were processed for next generation DNA sequencing at the Cincinnati Children's Hospital Medical Center (CCHMC) DNA Sequencing Core. LAM $2^{nd}$ exponential PCR products were purified using QIAquick PCR purification kit (Qiagen) then rendered blunt ended by end repair with T4 DNA polymerase, Klenow and T4 PNK (Promega) in the presence of 10 mM dNTPs (Thermo Fisher). Blunt-end products were randomly concatenated by treatment with T4 Quick Ligase (NEB) at room temperature for 15 min. Next generation sequencing libraries compatible with the Illumina system were prepared using the Nextera in-vitro transposition kit (Epicentre, Madison, Wis.) as per the manufacturer's recommendations and amplified using a different molecular barcode for each sample. After another round of PCR purification, all 10 libraries were quality checked on an Agilent Bioanalyzer (Agilent, Santa Clara, Calif.) then mixed in equal amount in a single pool. Sequencing was conducted on an Illumina HiSeq2000 (Illumina, San Diego, Calif.) in single read mode with indexing, producing 100 base long sequences.

After de-multiplexing of all the sequences in the pool and assignment to their respective samples, reads were processed and aligned to the mm9 mouse reference assembly using the CASAVA 1.8 package. Results were generated in the QSEQ SORTED file format so that alignments could be visualized using the ChIP-SEQ module of Illumina's Genome Studio software. Insertion sites detected by LAM PCR are characterized by an LTR sequence upstream of the insertion and an adapter sequence downstream. While the aligner was configured to position reads that contain only mouse genome sequence, reads that contained some LTR or some adapter sequence along with a majority of mouse sequence were also positioned. By zooming in to the base level display in Genome Studio (Illumina) it was possible to determine the edge of the covered regions and sides that matched the adapter sequence and the sides that matched the LTR sequence, allowing for the determination of the insertion point and the direction in which the provirus integrated. All identified insertions were compared to the National Center for Biotechnology Information (NCBI) mouse build 37 genome database (www.ncbi.nlm.nih.gov).

CRISPR/Cas9 Insertion of Proviral Sequences gRNA development. The reference sequence used for the initial description (Natkunam et al., *Blood* 109:1636-1642, 2007) of the LMO2 integration site (Homo sapiens chromosome 11 clone RP1-22J9 map of p12-14.1, GenBank #AL135799.8) was obtained from NCBI. This corresponds to GRCh38.p2 chr11:33890271. Genomic DNA was isolated from Jurkat cells and the region around the insertion site was PCR amplified using Q5 polymerase (NEB) and sequenced by the CCHMC DNA Sequencing and Genotyping Core. PCR primers were LMO2 FWD PCR (5'-TT-TAGGTTGCCCTGAAAAGGTG-3') (SEQ ID NO: 29) and LMO2 REV PCR (5'-GCCAAACACTCCTAGGCTCTTG-3') (SEQ ID NO: 30). Sequencing primers were LMO2 FWD PCR, LMO2 REV PCR, and LMO2 seq1 (5'-GTCTCTCGCAGCCACATGGG-3') (SEQ ID NO: 31). The region around the insertion site was analyzed for potential gRNA target sites using the Benchling CRISPR design program (https://benchling.com). Five gRNA were chosen on the basis of proximity to the planned insertion site, and low-predicted off-target effects. A plasmid containing both a gRNA and Cas9-T2A-eGFP expression cassettes (pX458m) (Transgenic Animal and Genome Editing Core, CCHMC). eGFP cDNA was first replaced with a mCherry reporter (pX458m-mCherry). Site-directed mutagenesis was performed using a QuikChange II XL Site-Directed Mutagenesis Kit (Agilent) to remove a BbsI site within the mCherry sequence (Primers 5'-CCCGTAATGCAGAAGAAAAC-CATGGGCTGGGAGGC-3' (SEQ ID NO: 32) and 5'-GCCTCCCAGCCCATGGTTTTCTTCTGCAT-TACGGG-3' (SEQ ID NO: 33). DNA oligos for cloning the target sequences into the pX458m-mCherry vector were designed and obtained from Integrated DNA Technologies (Coralville, Iowa). Oligos used to generate gRNA 1 with targeting sequence GATACCAATAGATATCAATC (SEQ ID NO: 34) were LMO2 gRNA 1 FWD (5'-CACCGGGA-TACCAATAGATATCAATC-3') (SEQ ID NO: 35) and LMO2 gRNA 1 REV (5'-AAACGATTGATATCTAT-TGGTATCCC-3') (SEQ ID NO: 36). Oligos used to generate gRNA 2 with targeting sequence ATCACCAGATTGA-TATCTAT (SEQ ID NO: 37) were LMO2 gRNA 2 FWD (5'-CACCGGGATCACCAGATTGATAT CTAT-3') (SEQ ID NO: 38) and LMO2 gRNA 2 REV (5'-AAACATAGA-TATCAATCTGGTGATCCC-3') (SEQ ID NO: 39). Oligos used to generate gRNA 3 with targeting sequence AATTG-CATAGTCGTGAAGTC (SEQ ID NO: 40) were LMO2 gRNA 3 FWD (5'-CACCGGGAATTGCATAGTCGT-GAAGTC-3') (SEQ ID NO: 41) and LMO2 gRNA 3 REV (5'-AAACGACTTCACGACTATGCAATTCCC-3') (SEQ ID NO: 42). Oligos used to generate gRNA 4 with targeting sequence ATTGCATAGTCGT GAAGTCA (SEQ ID NO: 43) were LMO2 gRNA 4 FWD (5'-CACCGGGATTGCAT-AGT CGTGAAGTCA-3') (SEQ ID NO: 44) and LMO2 gRNA 4 REV (5'-AAACTGACTTCA CGAC-TATGCAATCCC-3') (SEQ ID NO: 45). Oligos used to generate gRNA 5 with targeting sequence TCGT-GAAGTCAGGGCTTCTA (SEQ ID NO: 46) were LMO2 gRNA 5 FWD (5'-CACCGGGTCGT-GAAGTCAGGGCTTCTA-3') (SEQ ID NO: 47) and LMO2 gRNA 5 REV (5'-AAACTAGAAGCCCTGACTT-CACGACCC-3') (SEQ ID NO: 48).

pX458m-mCherry was digested with FastDigest BbsI (Thermo Fisher) and simultaneously dephosphorylated with FastAP (Thermo Fisher). The digested product was then gel purified. Oligo pairs were phosphorylated and annealed in a reaction of 100 μM of each oligo and T4 Polynucleotide Kinase (NEB) and placed in a Veriti 96-Well Fast Thermal Cycler (Thermo Fisher) for 37° C.×30 min, 95° C.×5 min, then ramped down to 25° C. at 5° C./min. The annealed oligos were then ligated into the cleaved pX458m plasmid and transformed into PX5-α competent cells (Protein Express, Cincinnati, Ohio). Plasmid was subsequently prepared using an EndoFree Plasmid Maxi Kit (Qiagen). 2 μg of each gRNA/Cas9 plasmid were transfected into 2.4×10$^5$ Jurkat cells in a 24-well plate using Lipofectamine 3000 (Thermo Fisher) per manufacturers' protocol. At day 7, cells were harvested and genomic DNA purified. The area around the target site was amplified using Q5 polymerase and sequenced (PCR primers: LMO2 FWD v3 5'-GCTTGGGTTTTACACG TCTTC-3' (SEQ ID NO: 49) and LMO2 REV v3 5'-TCAGCTAGAAAACAAGTACTTGC-3' (SEQ ID NO: 50), sequencing primer LMO2 seq1 5'-GTCTCTCGCAGC-CACATGGG-3') (SEQ ID NO: 147). The gRNA efficiency was determined using the Tracking of Indels by Decomposition (TIDE) assay (Shou et al., *Proc. of the Nat. Acad. of Sci.* 103:11730-11735, 2006).

Donor vector templates for homology directed repair (HDR). After sequencing the LMO2 region in Jurkat cells, about 600-bp homology arms were designed with a multiple cloning site region at the chosen insertion site. The homology vector was ordered as a plasmid in the pUC57 backbone from GenScript. The foamy virus pΔΦ.SF.eGFP.PRE was cut at the LTRs with XbaI and EcoNI and inserted between NheI and EcoNI. The lentivirus pRRL.PPT.SF.eGFP.PRE was cut at the LTRs with BsaI and PsiI and inserted between BbsI and NaeI. Retrovirus pRSF91.eGFP.PRE was cut at the LTRs between XhoI and HindIII and inserted between BsmFI and XhoI. The resulting clones were checked by restriction digest and sequenced for verification. For GV, the entire LTR sequences, which contain SFFV promoter/enhancers, were contained in the cloned sequence. To facilitate cloning of LV and FV, sequences from the R region of the 5' LTR through the entire 3' LTR were cloned from viral production plasmids. For the LV vector, the 40-bp of the 5' ΔU3 region (left after deletion of the U3 promoter/enhancer in the LTR), were not part of the cloned 'proviral' construct. This small region does not have enhancer/promoter activity and therefore was inconsequential for the purpose of studying genotoxicity. Similarly, in the case of the FV vector, the omitted 5' U3 region contains a 582-bp deletion, which removes the U3 TATA box and transcriptional enhancer sites of the LTR, leading to silencing of the LTR (Trobridge et al., *Methods Enzymol.* 346:628-48, 2002). As used herein, the term "provirus" refers to these LV and FV constructs.

After identifying the 36-bp insulator region in the FV LTR, the LMO2 donor containing pΔΦ.SF.eGFP.PRE was modified at the 5' LTR and 3' LTR to remove the identified CTCF binding sites. The initial sequence of this region was AGT AAA AGG ATT TGT ATA TTA GCC TTG CTA AGG GAG ACA TCT AGT GAT ATA AGT GTG AAC TAC ACT TAT CTT AAA TGA TG (SEQ ID NO: 51) to AGT AAA AGG ATT TGT ATA TTA GCC TTG CTA AGC ACA TTC GAT AGT GAT ATA AGA GGC TTT ATA TCT TAT CTT AAA TGA TG (SEQ ID NO: 52) (the insulator sequence is underlined). For the 3' LTR of the proviral sequence, a geneblock containing the modified insulator sequence was ordered from IDT to replace the ~800-bp region between EcoNI and MluI. For the 5' LTR, a gene synthesis product was ordered from GenScript to replace the ~550-bp region between PacI and AvrII. The resulting plasmid was confirmed by sequencing.

To add the 36-bp insulator sequence to the lentiviral LTRs, the following sequence was added ahead of the R region of the LTRs in the LMO2 donor containing pRRL.PPT.SF.eGFP.PRE: AAG GGA GAC ATC TAG TGA TAT AAG TGT GAA CTA CAC (SEQ ID NO: 53). Two geneblocks were ordered from IDT to replace the ~1 kb region between BsiWI and MluI encompassing the 3' LTR and the ~900-bp region between BspEI and MfeI encompassing the 5' LTR. The resulting plasmid was confirmed by sequencing.

Figure 3A:
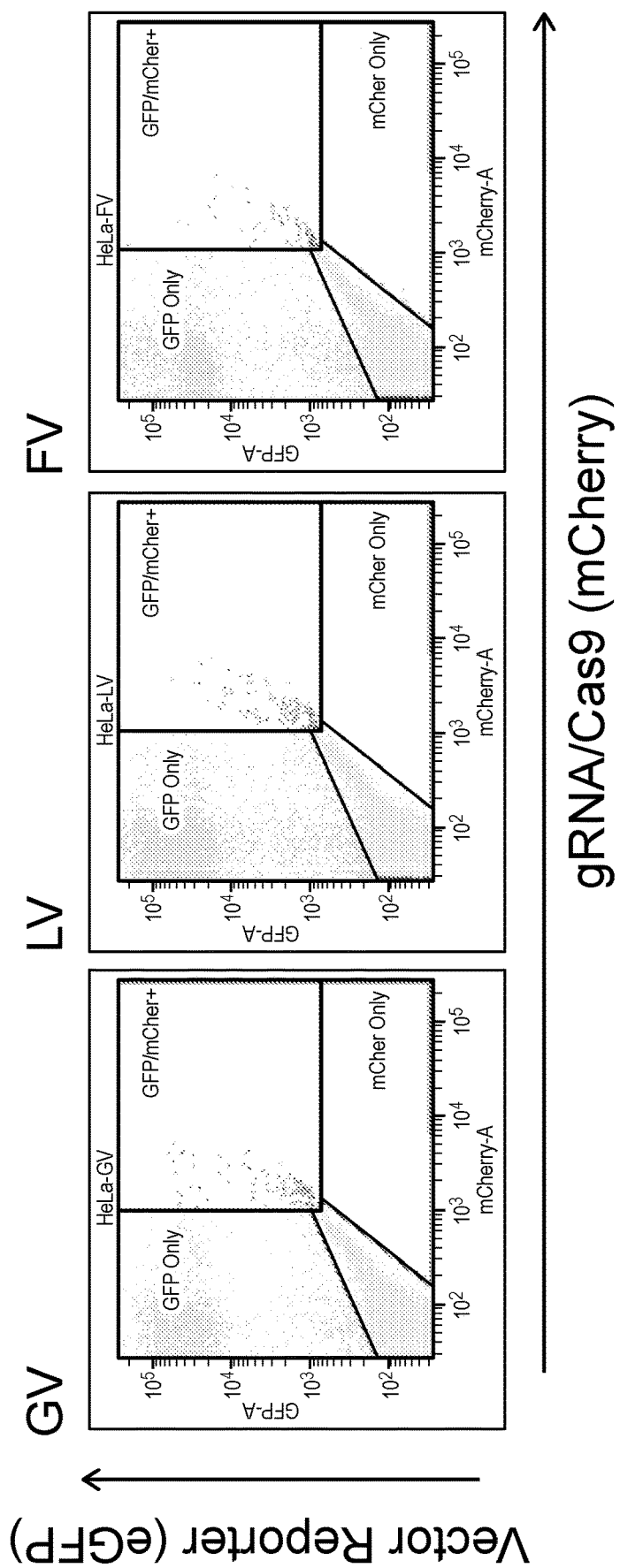
FIGS. 3A-3D include diagrams showing the establishment of HeLa LMO2 clones, following transfection and successful insertion of the proviral sequence via CRISPR/Cas9-mediated HR as indicated by GFP expression.

Generation of HeLa clones. On day −1, 5×10$^4$ cells were seeded into a 24-well plate. Cells were transfected with the LMO2 gRNA 5 plasmid as well as with one of the three (GV, LV, or FV) LMO2 donor plasmids. 500 ng of total DNA was transfected divided at an approximate molar ratio of 1:2 of LMO2 gRNA 5 plasmid to donor plasmid. Transfection was performed using 1.5 μL of Lipofectamine 3000 (Thermo Fisher) according to manufacturer's recommendations. Successful transfection was verified on day 2 by analyzing a portion of cells for expression of both eGFP (donor plasmid) and mCherry (LMO2 gRNA 5 plasmid) using a FACS Canto (BD Biosciences). At 2 weeks, cells were re-analyzed for eGFP and mCherry by FACS. GFP-positive and mCherry-negative cells were sorted as single cells into a 96-well plate using a BD FACSAria II by the Research Flow Cytometry Core at CCHMC (FIG. 3A).

After reaching at least 80% confluency, a portion of cells was harvested. DNA was purified by resuspending the cell pellet in 20 μL of QuickExtract DNA Extraction Solution (Epicentre) and incubated at 65° C. for 15 min, at 68° C. for 15 min, and at 98° C. for 10 min. Purified DNA was then screened for correct integration of the donor sequence by PCR using primer sets flanking the homology arms. The first PCR for ensuring correct 5' homology used primers LMO2 FWD v3 and Viral FWD (5'-

Figure 3B:
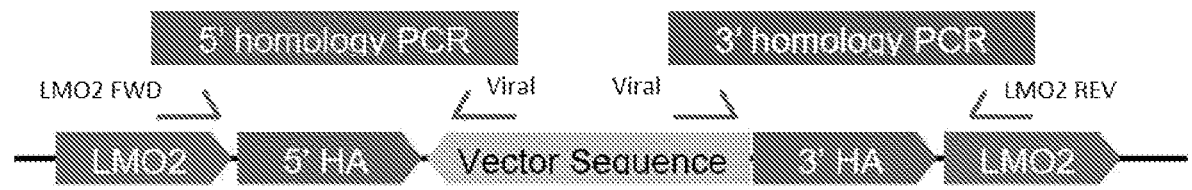
Figure 3C:
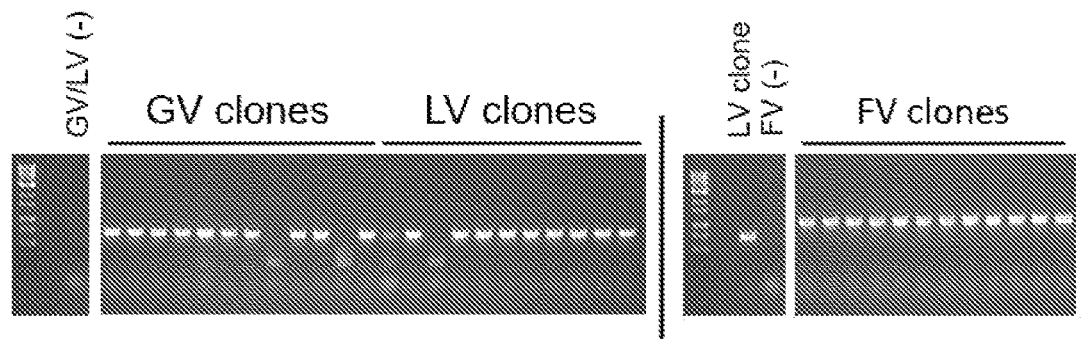
Figure 3D:
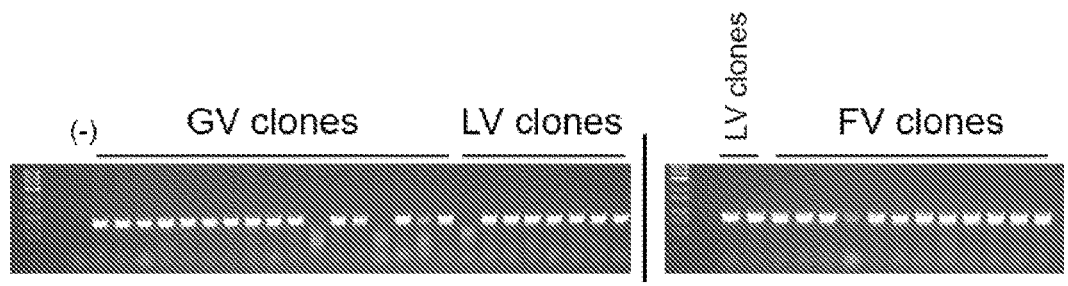
Figure 4A:
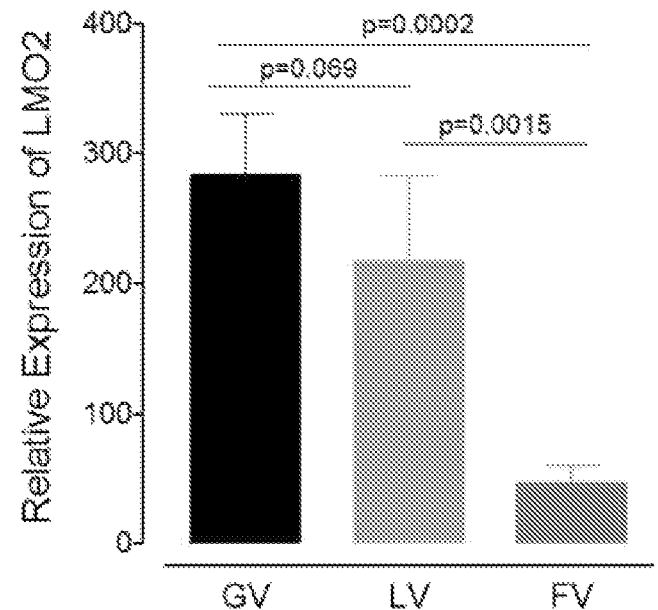
FIGS. 4A-4D include diagrams showing FV induces LMO2 mRNA expression to a lesser extent than either GV or LV. Depicted are data using two different primer/probe sets and two different endogenous controls.
Figure 4B:
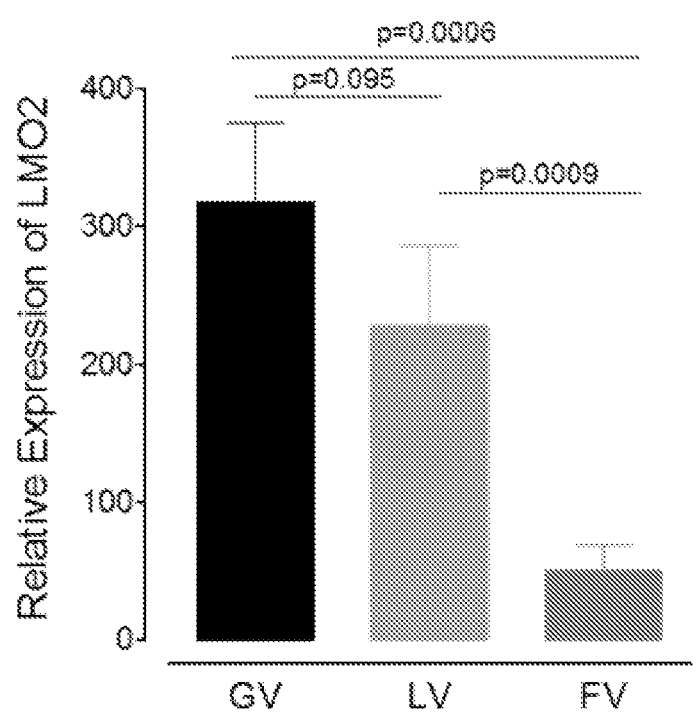
Figure 4C:
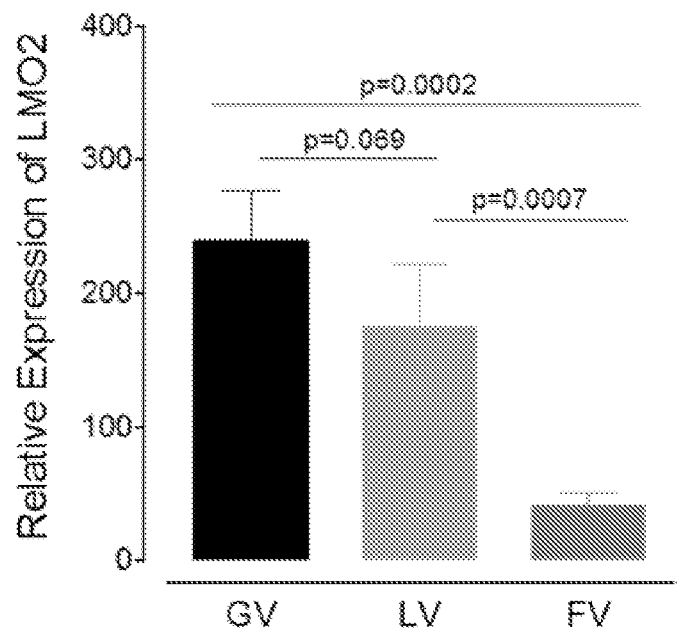
Figure 4D:
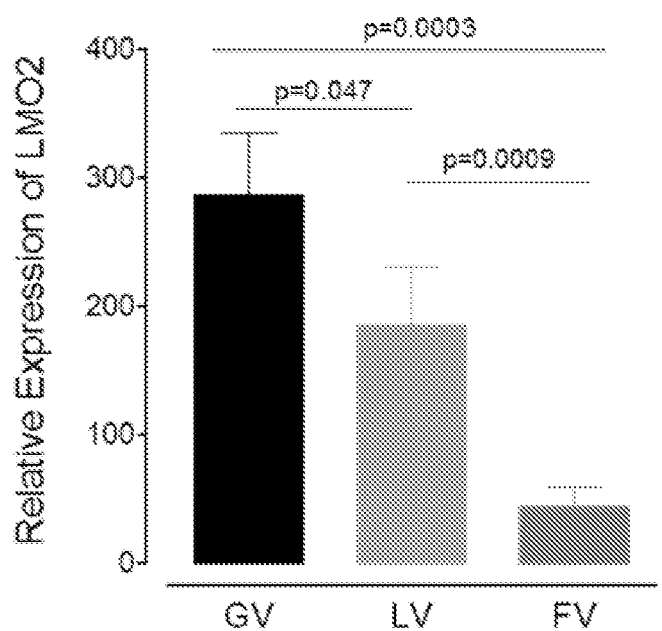
Figure 9A:
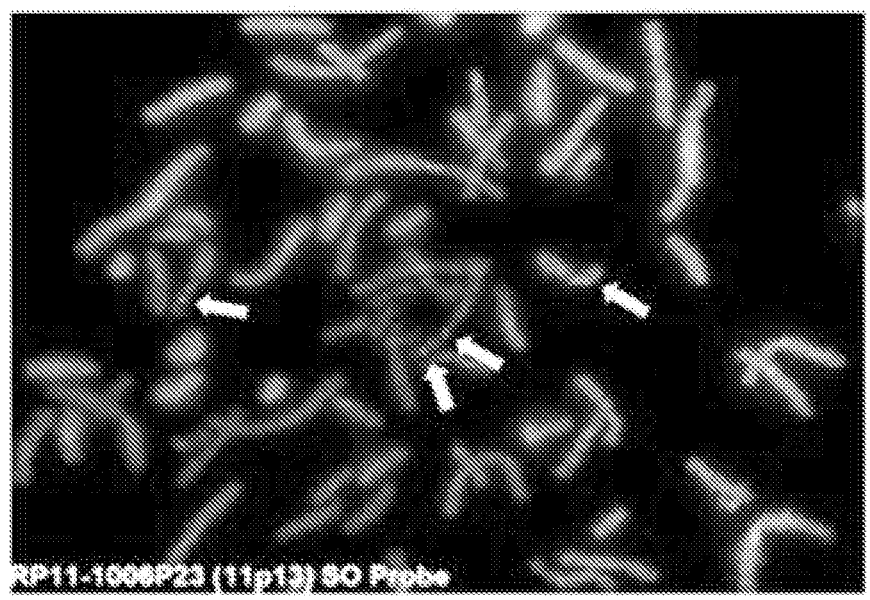
FIGS. 9A-9C include diagrams showing analysis of LMO2 copy numbers.
Figure 9B:
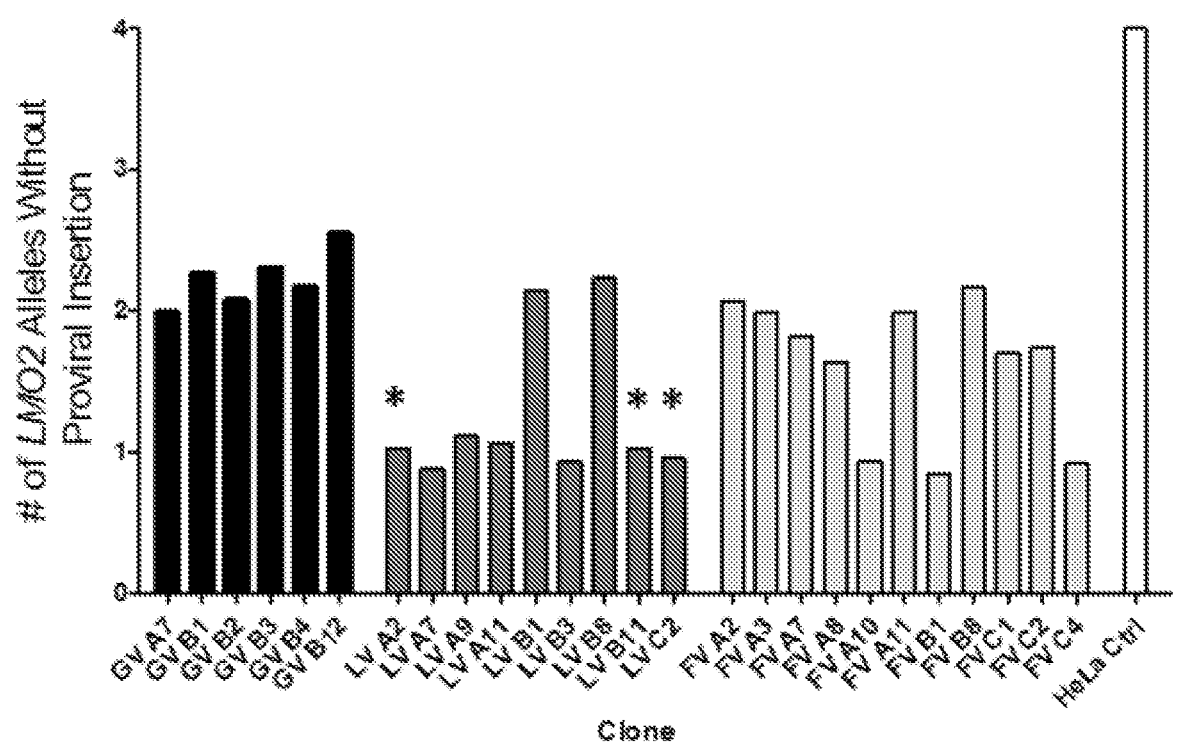
Figure 9C:
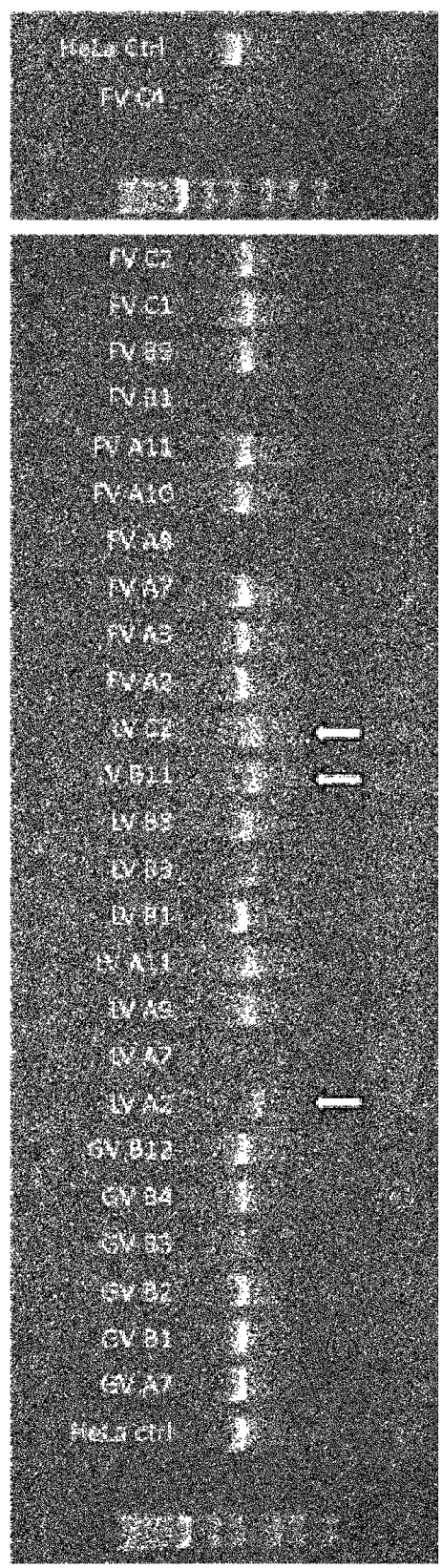

CGAGCGTTGGTAAGAGAAGC-3') (SEQ ID NO: 54). The second PCR (PCR 2) for ensuring correct 3' homology used a different FWD primer for FV. The second PCR for ensuring correct 3' homology used primers LMO2 REV v3 and either Viral REV1 (5'-GAGATCTGTCCCGCTAGCA-3') (SEQ ID NO: 55) for GV and LV or Viral REV2 (5'-GGATAATTTACAAATAAACCCGAC TTATATTCG-3') (SEQ ID NO: 56) for FV. Only correctly integrated sequences produced amplicons (FIGS. 3B-3D). Clones which had correct bands for both PCRs were considered to have correctly inserted viral sequences by HDR. HeLa cells have been reported to contain 3-4 copies of chromosome 11p, on which the LMO2 gene resides. Steps to estimate targeted allele copy number were the following: i) confirming that unedited/WT HeLa cells had 4 LMO2 alleles by fluorescent in situ hybridization (FISH) (FIG. 9A), ii) determining the number of edited non-targeted or WT LMO2 alleles using primers in the LMO2 gene that flank the Cas9 DSB/proviral insertion site, so that only WT/edited non-targeted LMO2 would be detected and LMO2 loci containing a provirus sequence insertion would not be amplified—WT/non-targeted LMO2 copy number analysis showed that all evaluable clones had 1-2 WT/non-targeted LMO2 copy (FIG. 9B)—and iii) further interrogating clones by PCR amplifying across the gRNA target site, followed by sequencing (PCR/sequencing primers were the same as those used for the TIDE assay) to assess for the presence of large deletions and indels in each clone (FIG. 9C). FISH was performed using a RP11-1006P23 FISH Probe (Empire Genomics, Buffalo, N.Y.) recognizing chromosome 11 (Chr11) (33,736,494-33,907,488). The number of non-targeted/WT LMO2 alleles was calculated relative to unedited HeLa cells. There was relatively similar non-targeted/WT LMO2 copy numbers between clones. N=3 for each clone.

LMO2 expression analysis by qRT-PCR. RNA was prepared by lysing cells in RNA Stat-60 (AMS Biotechnology, Abingdon, United Kingdom) and passing over a QIAshredder column (Qiagen). RNA was isolated by chloroform phase separation. The aqueous layer was precipitated with isopropanol and the resulting pellet was washed with 75% ethanol. RNA pellets were re-suspended in nuclease-free molecular-grade water and dissolved by incubation at 55° C. RNA was quantified using a NanoDrop 1000 Spectrophotometer (Thermo Fisher). cDNA was prepared with purified RNA using the High-Capacity cDNA Reverse Transcription Kit (Thermo Fisher). cDNA was generated from LMO2-modified clones containing FV, LV, FV with no insulator, and LV with FV insulator placed in the LTR. LMO2 mRNA expression was determined using qRT-PCR. An Hs001534473_m1 primer/probe set and PPIA endogenous control were used to acquire the data. N=5, 6, 17, and 9 clones, respectively (FIG. 8). cDNA was also generated from GV, LV, and FV clones, and LMO2 mRNA expression determined using RT-PCR. LMO2 mRNA expression in HeLa clones was determined by RT-PCR with two probe and primer sets, LMO2 TaqMan Genomic Assays Hs00277106 and Hs00153473 (Thermo Fisher), corresponding to two different regions in LMO2 cDNA, and using two different validated loading controls for HeLa cells, human PPIA and GAPDH (Thermo Fisher) (Stein et al., *Nat Med* 16:198-204, 2010). The LMO2 regions amplified are found in all reported transcript variants. Both probe/primer sets bridge exons, so only mRNA will be amplified. For LMO2 transcript variant 1 (NM_005574.3) the probe/primer sets bridge exons 4-5 and 5-6, respectively. qRT-PCR reactions were prepared with iTaq Universal Probes Supermix (Bio-Rad, Hercules, Calif.). The ABI 7900HT Real-Time PCR System was used to run the qRT-PCR. Data from the RT-PCR was analyzed by relative quantification using the $2^{-\Delta\Delta C_T}$ method (Schmittgen et al., *Nat. Protocols* 3:1101-1108, 2008) using human GAPDH/PPIA to normalize results and determine fold induction. Unedited HeLa samples were used as calibrators.

WT LMO2 copy number analysis. Genomic DNA was isolated from HeLa clones. Reactions were prepared with iTaq Universal Probes Supermix (Bio-Rad). Human ApoB was used as an endogenous control gene. The CFX Connect Real-Time PCR Detection System (Bio-Rad) was used to run the qRT-PCR. Data from the RT-PCR was analyzed by relative quantification using the $2^{-\Delta\Delta C_T}$ method (Schmittgen et al., *Nat. Protocols* 3:1101-1108, 2008) using a K562 cell line and unedited HeLa cells to normalize results and determine copy number. Primer and probe sets were the following:

```
LMO2-CN-FW
                                (SEQ ID NO: 57)
(5'-TGGGGAACAAGTACAATTTTGTG-3'),

LMO2-CN-RV2
                                (SEQ ID NO: 58)
(5'-CAATGTGGTGATATCAATCTGGTG-3'),

LMO2-CN-Probe
                                (SEQ ID NO: 59)
(5'-ACAAGCGTAAATTGCATAGTCGTGA-3'), hApoB-CN-FW
                                (SEQ ID NO: 60)
(5'-CTTGGTTTATGAATCTGGCTC-3'), hApoB-CN-RV
                                (SEQ ID NO: 61)
(5'-GCCTTTAGCAGTTAGAACAC-3'), hApoB-CN-Probe
                                (SEQ ID NO: 62)
(5'-ACATGCTGGGAATCGACTTGTGAT-3').
```

Western blot analysis of LMO2 protein expression. Western blot analysis for LMO2 expression was performed on SFFV-GV, SFFV-LV, and SFFV-FV clones. The clones used are indicated by the letter and number designations above each row in FIG. 5. Untransduced HeLa cells (−) and K562 cells (+) serve as the negative and positive controls, respectively. Endogenous GAPDH expression was used as a loading control. First, cells were lysed in RIPA lysis buffer (Santa Cruz, Dallas, Tex.) and 20 µL of protein lysate (containing between 30 and 87 micrograms protein per sample) was separated on a 4-15% Mini-PROTEAN TGX precast protein gel (Bio-Rad) and transferred onto a nitrocellulose PVDF membrane (Bio-Rad). The membrane was blocked with Odyssey Blocking Buffer (LI-COR Biosciences, Lincoln, Nebr.) and probed with a primary human LMO2 antibody and secondary anti-goat IRDye 800CW antibody (LI-COR Biosciences). The membrane was then re-probed with a primary human GAPDH antibody (Fitzgerald, Acton, Mass.) and secondary anti-mouse IRDye 680LT (LI-COR Biosciences). Signals were visualized using an Odyssey 9120 Infrared Imager (LI-COR Biosciences).

Electrophoretic mobility shift assay. Oligos were designed corresponding to predict CTCF binding sites in the LV and FV proviral sequences. Oligos labeled with IRDye® 700 at the 5' end were ordered from Integrated DNA Technologies (IDT). LV1 probe, made by annealing oligos 5'-ACAAGATAGAGGAAGAGCAAAACAAAAGTAA-GACCACCGCACAGCAAGCGGCC GCTGATCTTCA-GACCTGGAGGAGGAGATATGAGGGA-3' (SEQ ID NO:

63) and 5'-TCCCTCATATCTCCTCCTCCAGGTCTGAA-GATCAGCGGCCGCTTGCTGTGCGGTG GTCT-TACTTTTGTTTTGCTCTTCCTCTATCTTGT-3' (SEQ ID NO: 64), contained the GGAAGAGCA and CTCCTCCTCCAGGT (SEQ ID NO: 65) sequence motifs. LV2 probe, made by annealing oligos 5'-GA-TACCTAAAGGATCAACAGCTCCTGGGGAT-TTGGGGT TGCTCTGGAAAACTCATTTGCAC-CACTGCTGTGCCTTGGAATGCT-3' (SEQ ID NO: 66) and 5'-AGCATTCCAAGGCACAGCAGTGGTGCAAAT-GAGTTTTCCAGAGCAAC CCCAAATCCCCAG-GAGCTGTTGATCCTTTAGGTATC-3' (SEQ ID NO: 67), contained the TCCCCAGGAGCTGTTGATCC (SEQ ID NO: 68) and GGCACAGCA sequence motifs. LV3 probe, made by annealing oligos 5'-GTCGGG-GAAGCTGACGTCCTTTCGAATTCGA TAT-CAAGCTGTACCTTTAAGACCAATGACTTA-CAAGGCAGCTGTAGATC-3' (SEQ ID NO: 69) and 5'-GATCTACAGCTGCCTTGTAAGTCATTGGTCT-TAAAGGTACAGC TTGATATCGAAT-TCGAAAGGACGTCAGCTTCCCCGAC-3' (SEQ ID NO: 70), contained the GGTACAGCT sequence motif. FV1 probe, made by annealing oligos 5'-TCCAT-TAACACTCTGCTTATAGATTGTAAGGGTGAT-TGCAATGCTTTCTGCATAA AACTTTGGTTTTCTTGT-TAATCAAT-3' (SEQ ID NO: 71) and 5'-ATTGATTAACAAGA AAACCAAAGTTT-TATGCAGAAAGCATTGCAATCACCCTTACAATC-TATAAGCAGA GTGTTAATGGA-3' (SEQ ID NO: 72), contained the AGCATTGCA sequence motif. FV2 probe, made by annealing oligos 5'-AGTAAAAGGATTTGTAT-ATTAGCCTTGCTAA GGGAGACATCTAGTGA-TATAAGTGTGAACTACACTTATCTTAAATGATG-3' (SEQ ID NO: 73) and 5'-CATCATTTAAGA-TAAGTGTAGTTCACACTTATATCACTAGATG TCTCCCTTAGCAAGGCTAATATACAAATCCTTT-TACT-3' (SEQ ID NO: 74), contained the ATATCACTA-GATGTCTCCCT (SEQ ID NO: 75) and overlapping sequence motifs. FV3 probe, made by annealing oligos 5'-TCGGGTTTATTTGTAAATTATCCCTAGGG ACCTCCGAGCATAGCGGGAGGCATATAAAAGC-CAATAGACAATGGCTAGCA-3' (SEQ ID NO: 76) and 5'-TGCTAGCCATTGTCTATTGGCTTT-TATATGCTCCCGCTAT GCTCGGAGGTCCCTAGG-GATAATTTACAAATAAACCCGA-3' (SEQ ID NO: 77), contained the AGCATAGCG sequence motif. FV4 probe, made by annealing oligos 5'-GGCATCAGCCTA-CAAATACCAGTATTCATACT-GAAGGCAATGCCCTAGCAGATA AGCTTGCCACC-CAAGGAAGTTATGTA-3' (SEQ ID NO: 78) and 5'-TACATAACTT CCTTGGGTGGCAAGCT-TATCTGCTAGGGCATTGCCTTCAGTAT-GAATACTGGTAT TTGTAGGCTGATGCC-3' (SEQ ID NO: 79), contained the GGCATTGCC sequence motif. FV5 probe, made by annealing oligos 5'-CGCAACTGT-TAAATCTCTCAATGTACTCACT AGTATTGCAATTC-CAAAGGTGATTCACTCTGATCAAGGTGCAGCAT-TCA-3' (SEQ ID NO: 80) and 5'-TGAATGCTGCACCTTGATCAGAGTGAAT-CACCTTTGGAATTGC AATACTAGTGAGTACATT-GAGAGATTTAACAGTTGCG-3' (SEQ ID NO: 81), contained the GGAATTGCA sequence motif. FV6 probe, made by annealing oligos 5'-CTCGTTCCTGGTCTCCTGTTGTTGGCCAAT-TGGTCCAGGAGAGGGTGGCTAGGCC TGCTTCTTT-GAGACCTCGTTGGCAT-3' (SEQ ID NO: 82) and 5'-ATGCCAACGAG GTCT-CAAAGAAGCAGGCCTAGCCACCCTCTCCTGGAC-CAATTGGCCAACAACAG GAGACCAGGAACGAG-3' (SEQ ID NO: 83), contained the TGGTCCAGGAGAGGGT GGCT (SEQ ID NO: 84) and overlapping sequence motifs. FV7 probe, made by annealing oligos 5'-AT-GAGGCACTTCAGAATACAACAACTGTGACT-GAACAGCAGAAGGA ACAAATTATACTGGACATT-CAAAATGAAGAAGTA-3' (SEQ ID NO: 85) and 5'-TACTTCTTCATTTTGAATGTCCAGTATAAT-TTGTTCCTTCTGCTGTTCAGTCACAGT TGTTGTAT-TCTGAAGTGCCTCAT-3' (SEQ ID NO: 86), contained the TGAACAGCAG AAGGAACAAA (SEQ ID NO: 87) and overlapping sequence motifs. FV8 probe, made by annealing oligos 5'-TATGGAAGCTTATGGACCTCAGAGAG-GAAGTAACGAGGAG AGGGTGTGGTGGAATGC-CACTAGAAACCAGGGAAAACAAG-3' (SEQ ID NO: 88) and 5'-CTTGTTTTCCCTGGTTTCTAGTGGCATTC-CACCACACCCTCTCCTCGTTA CTTCCTCTCT-GAGGTCCATAAGCTTCCATA-3' (SEQ ID NO: 89), contained TAACGAGGAGAGGGTGTGGT (SEQ ID NO: 90), GGCATTCCA and overlapping sequence motifs. Similarly, FV2 mutant 1 probe was made by annealing oligos 5'-AGTAAAAGGATTTGTATATTAGCCTTGCTAAGG-GAGACATCTAGTGATATAAGag gctttatatcTTATCT-TAAATGATG-3' (SEQ ID NO: 91) and 5'-CATCATTTAA-GATAAgata taaagcctCTTATATCACTAGATGTCTCCCT-TAGCAAGGCTAATATACAAATCCTTTTA CT-3' (SEQ ID NO: 92). FV2 mutant 2 probe was made by annealing oligos 5'-AGTAAAAGGATTTGTATATT-AGCCTTGCTAAGGGAGACATCaggctttatatcTGTGAAC TACACTTATCTTAAATGATG-3' (SEQ ID NO: 93) and 5'-CATCATTTAAGATAAG TGTAGTTCACAga-tataaagcctGATGTCTCCCTTAGCAAGGCTAATATA-CAAATCCTTT TACT-3' (SEQ ID NO: 94). FV2 mutant 3 probe was made by annealing oligos 5'-AGTAAAAGGAT-TTGTATATTAGCCTTGCTaggctttatatcTAGTGA-TATAAGTGTGAAC TACACTTATCTTAAATGATG-3' (SEQ ID NO: 95) and 5'-CATCATTTAAGATAAGTG TAGTTCACACTTATATCACTAga-tataaagcctAGCAAGGCTAATATACAAATCCTTTTA CT-3' (SEQ ID NO: 96). FV2 mutant 4 probe was made by annealing oligos 5'-AGTAAAAGGATTTGTATaggctttatat-cAAGGGAGACATCTAGTGATATAAGTGTGAA CTA-CACTTATCTTAAATGATG-3' (SEQ ID NO: 97) and 5'-CATCATTTAAGATAA GTGTAGTTCACACTTATAT-CACTAGATGTCTCCCTTgatataaagcctATA-CAAATCCTTT TACT-3' (SEQ ID NO: 98). FV2 mutant 5 probe was made by annealing oligos 5'-AGTAAAAGGAT-TTGTATATTAGCCTTGCTaagcacattcgaTAGTGA-TATAAGaggctttatatc TTATCTTAAATGATG-3' (SEQ ID NO: 99) and 5'-CATCATTTAAGATAAgatataaagcct CTTATATCACTAtcgaatgtgcttAGCAAGGCTAATATA-CAAATCCTTTTACT-3' (SEQ ID NO: 100). FV2 mutant 6 probe was made by annealing oligos 5'-AGTAAAAGGAT-TTG TATATTAGCCTTGCTaagcacattcgaaggctttatatcTGT-GAACTACACTTATCTTAAATGAT G-3' (SEQ ID NO: 101) and 5'-CATCATTTAAGATAAGTGTAGTTCACAga-tataaagccttc gaatgtgcttAGCAAGGCTAATATA-CAAATCCTTTTACT-3' (SEQ ID NO: 102). Of note, one LV predicted binding site was not interrogated. A probe corresponding to the H19-Igf2 locus (H19), previously shown to bind CTCF, was used as a positive control (Hark et al., Nature 405:486-489, 2000). Unlabeled H19 probe was used for competition assays. Oligos were annealed in duplex buffer (IDT). Purified full-length human recombinant CTCF protein (Abnova, Taipei City, Taiwan) and labeled oligo-nucleotides were incubated at room temperature for 30 min in 20 mM HEPES (pH 7.5), 50 mM KCl, 5 mM MgCl$_2$, 3.3 µM ZnSO$_4$, 1 mM dithiothreitol, 0.3 mg/ml BSA, 0.5 µg poly(dI:dC), 5% glycerol, and 0.5% triton X-100 (Spencer et al., *Genetics* 189:441-454, 2011). Binding reactions were then resolved on 6% Novex TBE gels (Thermo Fisher) using 0.5×TBE running buffer (Thermo Fisher). Gels were imaged using an Odyssey 9120 Infrared Imager.

Chromatin Immunoprecipitation (ChIP). PCR was performed on ChIP input for HeLa control cells and the FV A2 clone, and on ChIP product for the FV A2 clone. Briefly, HeLa cell clones (1–2×10$^7$ cells) from transfected FV, LV and untransfected control HeLa cells were treated with formaldehyde (1% final concentration) and incubated at 37° C. for 10 min to crosslink histones to DNA. The formaldehyde was neutralized with 2.5M glycine (final concentration 0.25M) for 5-10 min at room temperature and centrifuged for 5 min at 2000 rpm. The cells were pelleted and stored at −80° C. For ChIP, cells were thawed and pellet was resuspended in 200 µl of SDS lysis buffer (Millipore, Billerica, Mass.) and incubate on ice for 10 min and protease inhibitors (Pierce protease inhibitor, Thermo Fisher) were added (1 mM phenyylmethylsulfonyl fluoride (PMSF), 1 µg/mL aprotinin and 1 µg/mL pepstatin A) to the cell lysate. The lysate was sheared under optimized conditions [in Covaris TM S220 (Covaris, Woburn, Mass.) for 70 sec at 4° C., under peak power: 105, Duty factor: 10 and Cycles/Burst: 200] to generate cross-linked DNA fragments of 200-1000 base pairs in length. The sonicated samples were centrifuged for 10 minutes at 13,000 rpm at 4° C. The supernatant was diluted 10-fold with ChIP dilution buffer (Millipore) and protease inhibitors were added as above. A portion (1%) of the sample was retained as the input sample. The diluted samples were then precleared with 75 µl of Salmon Sperm DNA/Protein A Agarose-50% slurry (Millipore) for 30 minutes at 4° C. with agitation. The agarose was pelleted by brief centrifugation and the 2 µl anti-CTCF antibody (Millipore) was added to 2 ml of precleared supernatant and incubated overnight at 4° C. with constant rotation. The next day, 60 µl of Salmon Sperm DNA/Protein A Agarose-50% slurry was added for one hour at 4° C. with rotation to collect the antibody/histone complex. The agarose was pelleted by gentle centrifugation at 1000×g for 1 minute and the supernatant with unbound chromatin was discarded. The protein A agarose/antibody/chromatin complex was washed sequentially with 1 ml each of low salt immune complex (Millipore), high salt immune complex (Millipore), LiCL immune complex (Millipore) and twice with TE buffer (Millipore) for 5 min at 4° C. with rotation. The TE wash buffer was removed and the protein A agarose/antibody/chromatin complex was resuspended in 250 µl of fresh elution buffer (1% SDS, 0.1M NaHCO3) and incubated at room temperature for 15 minutes with rotation. Agarose beads were spun down and the process was repeated twice and the eluates were combined. The crosslinks were reversed by adding 20 µl of 5M NaCl (Millipore) to the combined eluates and heated at 65° C. for 4 hours, followed by the addition of 10 µl of 0.5M EDTA (Millipore), 20 µl of 1M Tris-HCl, pH 6.5 (Millipore) and 2 µl of 10 mg/ml Proteinase K to the eluates. This mixture was incubated for one hour at 45° C. DNA was recovered from this eluate by using a PCR clean up kit (Qiagen). Following ChIP purification, eluted products were analyzed by qualitative PCR. The following primers, corresponding to predicted CTCF binding sites, were utilized: FV1 (5'-CGAGACTCTCCAGGTTTGGTAA-3' (SEQ ID NO: 103) and 5'-GGTTCTCGAATCAAGTCGGTTT-3' (SEQ ID NO: 104)), FV2, (5'-AACCGACTTGATTCGAGAACCT-3' (SEQ ID NO: 105) and 5'-GTTGGGCGCCAATTGTCAT-3' (SEQ ID NO: 106)), FV5 (5'-ACTAAGGCTCCTTC-TACTAGCG-3' (SEQ ID NO: 107) and 5'-GTT-GAAGAAGTGAATGCTGCAC-3' (SEQ ID NO: 108)), FV6 (5'-TTATACCATCCATCCACCCCTC-3' (SEQ ID NO: 109) and 5'-GTTTATGCCAACGA GGTCTCAA-3' (SEQ ID NO: 110)), and FV7 (5'-GCAT-GAGGCACTTCAGAATACA-3' (SEQ ID NO: 111) and 5'-AGGCCAATACTCTTGAGCTAGT-3' (SEQ ID NO: 112)). The H19 locus was again used as a positive control, using primers 5'-CCCATCTTGCTGAC CTCAC-3' (SEQ ID NO: 113) and 5'-AGACCTGGGACGTTT CTGTG-3' (SEQ ID NO: 114). The size of the amplicons for H19, FV1, FV2, FV5, FV6, and FV7 are 165, 157, 188, 110, 115, and 155-bp, respectively. ChIP input for HeLa control cells and a HeLa FV clone (FVA2), as well as ChIP product for the HeLa FV clone were assayed.

Statistical analysis. Two-tailed student's unpaired t-tests, using GraphPad software (GraphPad Software, Inc., La Jolla, Calif.), were used to calculate the statistical differences between groups in the immortalization assay. Immortalization frequency of SFFV and MSCV series of FV and LV vectors were compared against the replating frequency of SFFV-GV. Data are presented as mean±standard error of the mean (SEM) and differences of p<0.05 were considered statistically significant. RT-PCR data was analyzed using a one-tailed Mann-Whitney U test.

Results (A) Vector Design for Comparative Genotoxicity

The spleen focus-forming virus (SFFV) vector, a GV, was previously reported to generate a high frequency of immortalized clones in the in vitro immortalization (IVIM) assay (Modlich et al., *Blood* 108:2545-53, 2006, Zychlinski et al., *Mol. Ther.* 16:718-25, 2008), which has correlated with the occurrence of leukemia in mice (Zychlinski et al., *Mol. Ther.* 16:718-25, 2008) and with a high incidence (80-100%) of MDS and leukemia in the CGD and WAS gene therapy trials. Herein, analogous enhanced green fluorescent protein (eGFP) encoding FV and LV vectors carrying the internal enhancer/promoters from the U3 region of the SFFV LTR, or FV and LV vectors carrying internal enhancer/promoter from another GV LTR from the murine stem cell virus (MSCV) was constructed: (1) ΔΦSF.eGFP carries an internal SFFV enhancer/promoter (SFFV-FV); (2) ΔΦMSCV.eGFP carries an internal MSCV enhancer/promoter (MSCV-FV). These vectors were compared to the analogous LV vector, RRL.ppt.SF.eGFP.pre, which carries an internal SFFV enhancer/promoter (SFFV-LV) and GV, SF91-eGFP.pre, which is driven by the SFFV LTR (SFFV-GV). MSCV.eGFP.pre, a GV carrying the MSCV LTR (MSCV-GV), and RRL.ppt.MSCV.eGFP.pre, a LV vector carrying an internal MSCV enhancer/promoter (MSCV-LV), were generated as positive controls with known high genotoxic potential (FIG. 1A). A promoter-less FV vector, M.eGFP, and mock transductions were included as negative controls.

(B) FV Vectors Showed Significantly Less Immortalization of Primary Mouse HSPC than GV and LV Vectors.

To compare the genotoxic potential, the above viral vectors were used in the in vitro immortalization (IVIM) assay. This assay is widely used as a preclinical screening tool and is particularly sensitive for a relative quantitative detection of myeloid lineage-related genotoxicity (Du et al., *Blood* 106:2498-505, 2005).

Lineage-negative (Lin−) cells from bone marrow of WT (C57BL/6J) mice were transduced with the SFFV and MSCV GV, LV and FV vectors using optimized transduction protocols for each vector (Ott et al., *Nature Medicine* 12:401-9, 2006, Bauer et al., *Nat. Med.* 14:93-7, 2008, Puthenveetil et al., *Blood* 104:3445-53, 2004). Cells were expanded for 2 weeks and then cloned, as previously described (Arumugam et al., *Mol. Ther.* 17:1929-37, 2009). By 2 weeks, untransduced/mock Lin– cells terminally differentiated and died. If vector insertion conferred a proliferative potential, clonal outgrowth occurred, creating 'immortalized' clones. The replating frequency (immortalization frequency) of cells transduced with GV, LV and FV vectors was assessed at 2 weeks and at 5 weeks. All wells with immortalized cells were picked for expansion. Cells transduced with SFFV driven GV or LV vectors expanded robustly, even at 5 weeks. Transduction efficiency (measured by GFP marking) of Lin– cells in SFFV-GV, MSCV-GV, SFFV-LV, MSCV-LV, SFFV-FV, MSCV-FV transduced Lin– cells was 91%, 70%, 89%, 99%, 93%, 75%, respectively. The average VCN in Lin– cells transduced with the SFFV-GV, MSCV-GV, SFFV-LV, MSCV-LV, SFFV-FV, and MSCV-FV vectors was 8±2, 9±0.3, 10±2, 27±2, 7±0.8, 8.5±0.7 (mean±standard error of the mean), respectively (Table 1).

TABLE 1

Frequency of IVIM assay mutants

| Vector | Number of independent transductions | S/US cells plated | IVIM wells per 96-wells (at 2 Wk)* | 2 Wk replating frequency ** | Vector Copy number (VCN) | 5 Wk replating frequency *** | 5 Wk Replating Frequency/VCN **** |
|---|---|---|---|---|---|---|---|
| SFFV-GV | Transduction 1 | US | 15 | 0.00200 | 1.0 | 0.00200 | 0.002000 |
|  |  | S | 58 | 0.01000 | 5.7 | 0.00900 | 0.001579 |
|  | Transduction 2 | US | 17 | 0.00200 | 3.0 | 0.00200 | 0.000667 |
|  |  | S | 60 | 0.01000 | 5.4 | 0.01000 | 0.001852 |
|  | Transduction 3 | S | 96 | 0.04500 | 12 | 0.04500 | 0.003750 |
|  | Transduction 4 | US | 93 | 0.03400 | 14 | 0.03400 | 0.002429 |
|  | Transduction 5 | US | 92 | 0.03200 | 15 | 0.03200 | 0.002133 |
|  | Transduction 6 | US | 70 | 0.01300 | 8.0 | 0.01300 | 0.001625 |
|  | Transduction 7 | S | 82 | 0.01800 | 7.3 | 0.01800 | 0.002466 |
| Average |  |  | 65 | 0.01844 | 7.9 | 0.01844 | 0.002311 |
|  |  |  |  | (1 in 54)# |  | (1 in 54) | (1 in 452) |
| SFFV-LV | Transduction 1 | US | 13 | 0.00100 | 11.5 | 0.00100 | 0.000087 |
|  | Transduction 2 | US | 11 | 0.00120 | 15.0 | 0.00120 | 0.000080 |
|  |  | S | 20 | 0.00110 | 8.6 | 0.00110 | 0.000128 |
|  | Transduction 3 | US | 7 | 0.00080 | 6.0 | 0.00080 | 0.000133 |
|  | Transduction 4 | US | 25 | 0.00300 | 14.0 | 0.00300 | 0.000214 |
|  | Transduction 5 | US | 27 | 0.00300 | 10.0 | 0.00300 | 0.000300 |
|  | Transduction 6 | US | 21 | 0.00260 | 10.5 | 0.00260 | 0.000248 |
| Average |  |  | 18 | 0.00181 | 10.8 | 0.00181 | 0.000168 |
|  |  |  |  | (1 in 552) |  | (1 in 552) | (1 in 5,952) |
| SFFV-FV | Transduction 1 | US | 1 | 0.00003 | 3.7 | 0.00003 | 0.000008 |
|  |  | S | 2 | 0.00020 | 8.6 | 0.00020 | 0.000023 |
|  | Transduction 2 | US | 1 | 0.00002 | 6.8 | 0.00002 | 0.000003 |
|  |  | S | 2 | 0.00020 | 8.3 | 0.00010 | 0.000012 |
|  | Transduction 3 | S | 5 | 0.00026 | 9 | 0.00020 | 0.000022 |
|  | Transduction 4 | US | 4 | 0.00008 | 6 | 0.00003 | 0.000005 |
|  |  | S | 3 | 0.00030 | 9.3 | 0.00003 | 0.000003 |
| Average |  |  | 3 | 0.00015 | 7.4 | 0.00009 | 0.000012 |
|  |  |  |  | (1 in 6667) |  | (1 in 11,111) | (1 in 83,333) |
| Promoter-less FV | Transduction 1 | US | 0 | 0.00005 | 3.8 | 0.00000 | 0.000000 |
|  | Transduction 2 | US | 1 | 0.00010 | 16.8 | 0.00001 | 0.000001 |
|  | Transduction 3 | US | 0 | 0.00005 | 6 | 0.00000 | 0.000000 |
|  | Transduction 4 | US | 1 | 0.00010 | 12 | 0.00001 | 0.000001 |
| Average |  |  | 0.5 | 0.00008 | 9.6 | 0.00001 | 0.000001 |
|  |  |  |  | (1 in 12,500) |  | (1 in 100,000) | (1 in 1000,000) |
| MSCV-GV | Transduction 1 | US | 48 | 0.00680 | 9.6 | 0.00680 | 0.000708 |
|  |  | S | 36 | 0.00469 | 9.2 | 0.00469 | 0.000510 |
|  | Transduction 2 | US | 28 | 0.00344 | 8.2 | 0.00344 | 0.000420 |
|  |  | S | 65 | 0.0110 | 9.6 | 0.0110 | 0.001146 |
| Average |  |  | 44 | 0.00648 | 9.2 | 0.00648 | 0.000708 |
|  |  |  |  | (1 in 154) |  | (1 in 154) | (1 in 1,412) |
| MSCV-LV | Transduction 1 | US | 40 | 0.00530 | 25 | 0.0053 | 0.000212 |
|  | Transduction 2 | US | 23 | 0.00270 | 29 | 0.0027 | 0.000093 |
| Average |  |  | 32 | 0.00400 | 27 | 0.00400 | 0.000148 |
|  |  |  |  | (1 in 250) |  | (1 in 250) | (1 in 6,757) |
| MSCV-FV | Transduction 1 | S | 8 | 0.00087 | 9 | 0.00032 | 0.000036 |
|  | Transduction 2 | S | 9 | 0.00098 | 9 | 0.00021 | 0.000023 |
|  | Transduction 3 | US | 0 | 0.00000 | 6.4 | 0.00000 | 0.000000 |
|  |  | S | 3 | 0.00015 | 10 | 0.00005 | 0.000005 |
|  | Transduction 4 | US | 2 | 0.00010 | 6.5 | 0.00005 | 0.000008 |
|  |  | S | 3 | 0.00015 | 10 | 0.00005 | 0.000005 |
| Average |  |  | 4 | 0.00038 | 8.5 | 0.00011 | 0.000013 |
|  |  |  |  | (1 in 2631) |  | (1 in 9091) | (1 in 76,923) |

TABLE 1-continued

Frequency of IVIM assay mutants

| Vector | Number of independent transductions | S/US cells plated | IVIM wells per 96-wells (at 2 Wk)* | 2 Wk replating frequency ** | Vector Copy number (VCN) | 5 Wk replating frequency *** | 5 Wk Replating Frequency/VCN **** |
|---|---|---|---|---|---|---|---|
| Mock | NA | | 0 | 0 | 0 | 0 | 0 |
| | NA | | 0 | 0 | 0 | 0 | 0 |
| | NA | | 0 | 0 | 0 | 0 | 0 |
| | NA | | 0 | 0 | 0 | 0 | 0 |
| | NA | | 0 | 0 | 0 | 0 | 0 |
| | NA | | 0 | 0 | 0 | 0 | 0 |
| Average | NA | | 0 | 0 | 0 | 0 | 0 |

Column 3 shows the transduction pools that were sorted for eGFP+ cells by FACS.
NA—not applicable,
US—unsorted,
S—Sorted
*Column 4 depicts the number of wells with immortalized cells after 100,000 Lin− cells were, transduced, expanded and plated in a limiting dilution at 100 cells/well in 96-well plates.
Column 5: represents wells with immortalized cells (replating frequency) at 2 weeks calculated using Poisson statistics using the L-Calc software. The average replating frequency from individual transductions for each vector is denoted in shaded rows.
Data in parenthesis is another way of listing the frequency of Lin− cells immortalized by vector insertion. E.g. replating frequency of 0.001 means 1 in 1000 Lin− cells are immortalized by that vector.
** For vector-transduced wells negative for replating clones, calculations are based on the assumption that a replating clone would be detected if 97 wells were plated instead of 96 (Zychlinski et al., Mol. Ther. 16: 718-25, 2008).
Column 6 represents vector copy number (VCN) of transduced pools prior to plating in 96 wells.
Column 7 represents replating frequency at 5 weeks.
*** Since numerous immortalized clones were present with the SFFV-GV and SFFV-LV groups, based upon our previously reported equal fitness of these clones at 2 and 5 weeks, only a subset of 2 week immortalized were expanded for 5 weeks with these vectors. However, all the immortalized clones from the foamy viral vector group were expanded for 5 weeks further analysis.
**** Column 8: Immortalization frequency is normalized for vector copy number (with the assumption that one immortalization event is caused by a one vector insertion and immortalization frequency correlates linearly with vector copy number).

The fitness of immortalized clones (i.e. the ability to be replated and expand) after transduction with GV or LV vectors with SFFV/MSCV enhancers at 5 weeks was similar to that at 2 weeks. The number of immortalized clones with SFFV-GV and SFFV-LV was consistent with previously reported studies (Modlich et al., Mol. Ther. 17:1919-28, 2009). Notably, the immortalization frequencies of SFFV-FV and MSCV-FV were remarkably lower, by more than two orders of magnitude, as compared to their analogous SFFV-GV and MSCV-GV (p<0.01). The analogous SFFV-LV and MSCV-LV showed a 10-14 fold reduction in immortalization frequency as compared to SFFV-GV, consistent with prior reports (Modlich et al., Mol. Ther. 17:1919-28, 2009). In addition, the immortalized clones derived from FV transduction were not as fit as those derived from LV or GV transductions, as they had a lower expansion potential compared to clones with SFFV-GV and SFFV-LV insertions, and therefore lower 5-week replating frequency. Mean Sca-1 and c-Kit expression trended lower for SFFV-FV and MSCV-FV clones (69.6 and 57.5%, respectively) compared to SFFV-GV, SFFV-LV, and MSCV-LV clones (89.0, 76.6, and 70.5%, respectively), but the differences were not statistically significant (Mann Whitney, one tailed). The percentage of unique insertions from FV and LV vectors with respect to gene transcriptional units and non-genic/repeat sequences demonstrated a unique integration profile for FV compared to LV insertions. Integration sites for FV within genes, into non-genic/repeat sequences, and non-assignable were 27, 62, and 11%, respectively. LV was 60, 6, and 34%, respectively. The number of unique insertions for SFFV-FV and MSCV FV were 121 and 65 respectively. The number of unique insertions identified for MSCV LV was 270.

Figure 1B:
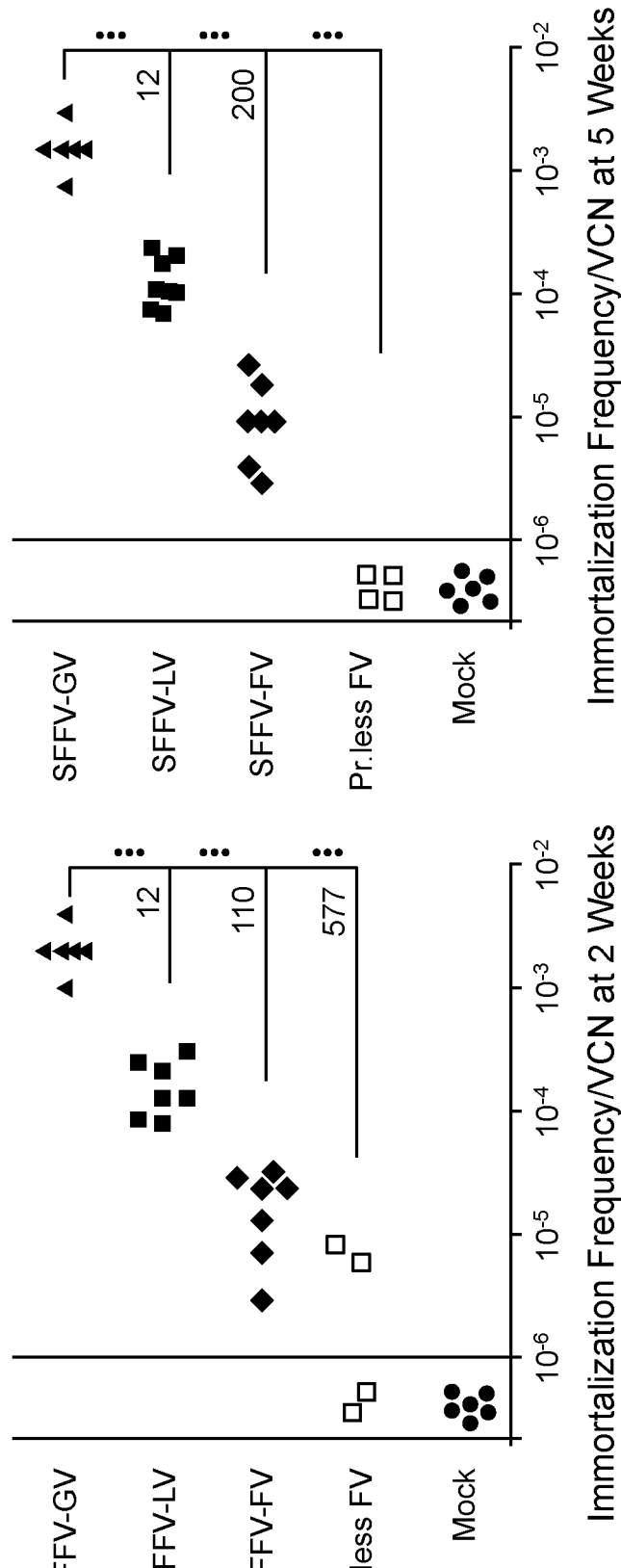
Figure 1C:
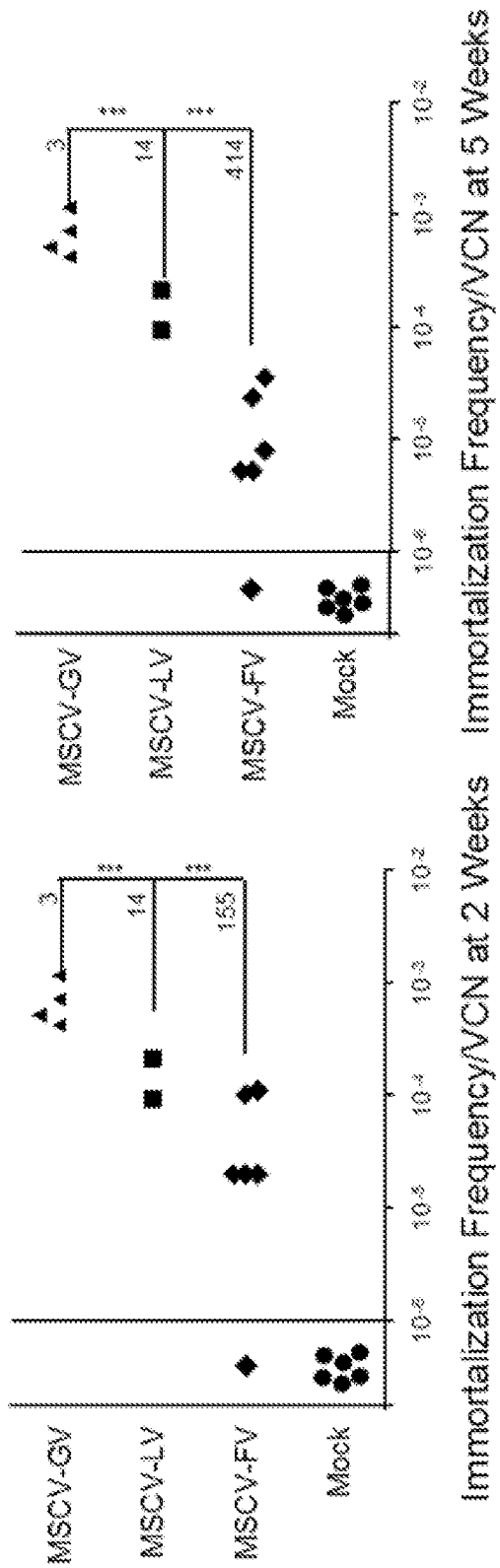

Each symbol in FIGS. 1B-1C represents the replating frequency normalized for VCN from one independent transduction experiment using the specified vector. Data points to the left of the horizontal line indicate independent transductions with no replating clones. Fold reduction in the frequency of immortalized mutants are denoted in FIGS. 1B-1C. To exclude differences in immortalization frequency due to VCN, the immortalization frequency of each vector was normalized to VCN (FIGS. 1B-1C), allowing comparative analysis of the relative genotoxicity. When normalized for VCN, the MSCV-GV vector had a 3-fold lower immortalization potential as compared to the SFFV-GV vector. Importantly, at 2 weeks the SFFV-FV and MSCV-FV vectors showed a 110-fold and 156-fold lower immortalization potential, respectively, as compared to the SFFV-GV vector. By 5 weeks, the immortalization potential of FV vectors declined even further, resulting in 155-fold and 414-fold lower immortalization potential of SFFV-FV and MSCV-FV vectors, respectively, as compared to the SFFV-GV vector. The SFFV-LV and MSCV-LV vectors showed a 12- and 14-fold reduction in immortalization frequency compared to the SFFV-GV vector, consistent with prior reports (Zychlinski et al., Mol. Ther. 16:718-25, 2008, Modlich et al., Mol. Ther. 17:1919-28, 2009). Supporting that immortalization in this assay occurred secondary to vector integration: i) there were no detectable immortalized clones in the mock transduced progenitor cultures, and ii) Promoterless FV had live wells at 2 weeks, but contained lower cell numbers, and were lost by 5 weeks, suggesting that they were not truly immortalized.

Figure 2A:
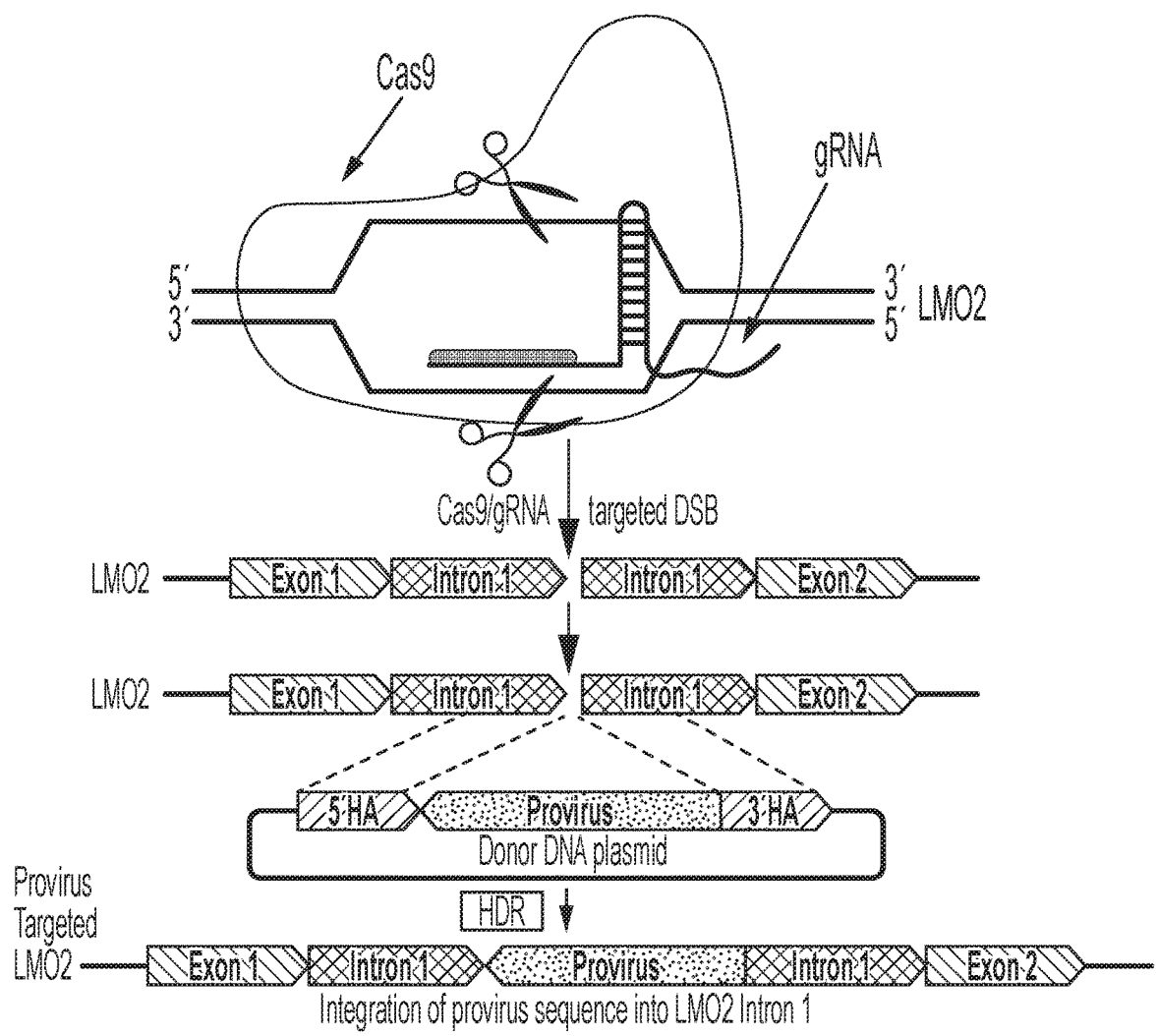
FIGS. 2A-2C include diagrams illustrating CRISPR/Cas9 facilitated insertion of GV, LV, and FV proviral sequences into a known locus previously shown to increase expression of LMO2.

(C) SFFV Provirus Showed Significantly Less LMO2 Expression than LV and GV Proviral Sequences as Determined by CRISPR/Cas9-Mediated Targeted Insertion The SFFV enhancer has been shown in the IVIM assay, in mice and in human trials to be one of the most genotoxic enhancers—(Ott et al., Nature Medicine 12:401-9, 2006, Montini et al., J Clin Invest 119:964-75, 2009, Modlich et al., Mol. Ther. 17:1919-28, 2009). The remarkably reduced genotoxicity (150- to 400-fold less) in the IVIM assay from the SFFV/MSCV enhancers in a FV vector, as shown here, could not be fully explained by the reported 2-fold higher propensity of FV to integrate in non-genic regions, especially when FV tends to integrate near TSS, like GV. These results suggest that the FV backbone may have an enhancer-blocking/insulator effect. To assess the potential enhancer blocking functionality of the vector backbone, without the confounding effects of the promoter/enhancer, transgene, or integration site, proviral forms of SFFV-GV, SFFV-LV and SFFV-FV were targeted into the LMO2 gene at the retroviral integration site (RIS) known to cause multiple cases of secondary leukemia (1-3). In order to isolate the genotoxic effects of viral vector backbone sequences from integration site effects, a CRISPR/Cas9-based assay was devised that allowed for integration of the proviral sequences of GV, LV, and FV, all encoding eGFP transgene driven by the SFFV promoter enhancer, at precisely the same locus within LMO2, and in the same direction (FIG. 2A). The insertion site for the viral vector sequences was based on a previous report of secondary leukemia in a patient following gene therapy for SCID-X1 using a GV vector (Hacein-Bey-Abina et al., Science 302:415-9, 2003). As illustrated in FIG. 2A, the gRNA/Cas9 ribonucleoprotein complex created a double strand break (DSB) near the insertion site. The DSB was generally repaired by non-homologous end joining (NHEJ), or by homologous recombination (HR) if a donor DNA, encoding the designed genetic modification flanked by homology arms, was provided.

Figure 2B:
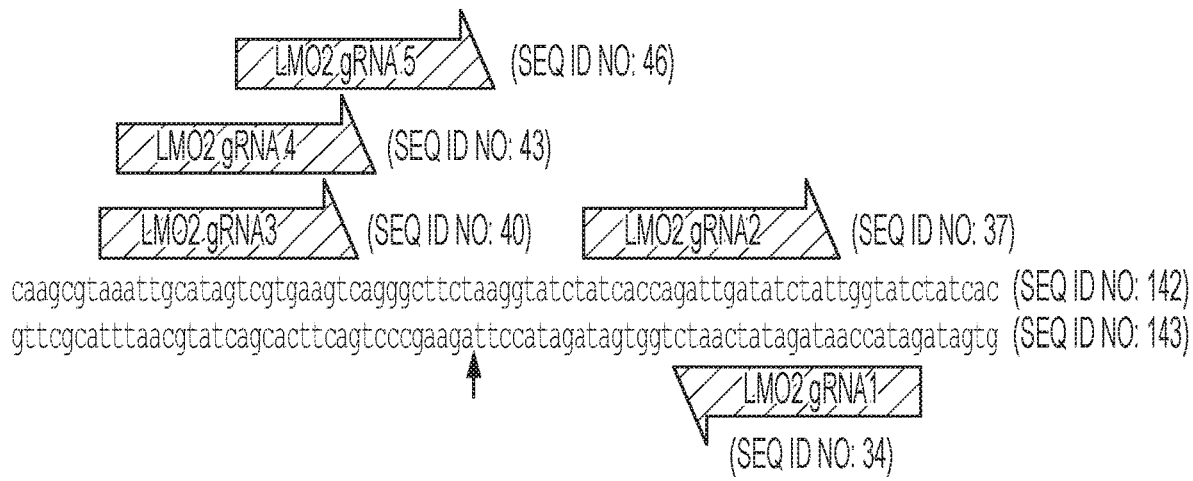
Figure 2C:
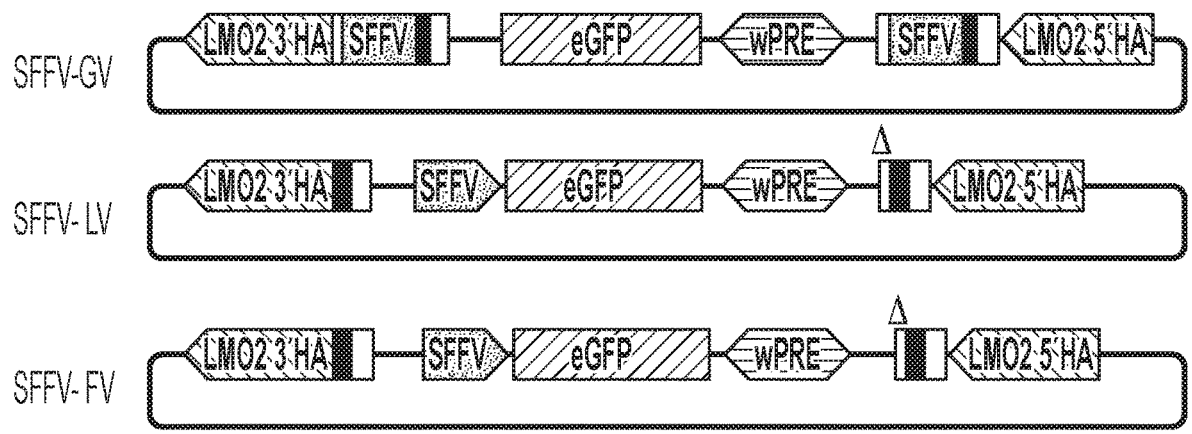

Five potential gRNA target sequences, each with low predicted off-target activity and in close proximity to the insertion site, were identified (FIG. 2B). LMO2 gRNA 5 was the most efficient, with an indel generation efficiency of 24.1% (efficiencies for gRNA 1-4 were 0, 13.3, 0, and 1.5%, respectively), and was used for subsequent experiments. Donor plasmids containing proviral cassettes for GV, LV, or FV were cloned (FIG. 2C). Sequences were constructed in reverse orientation to match the directionality of the insertion described previously (Hacein-Bey-Abina et al., Science 302:415-9, 2003). HeLa cells, which have very low LMO2 mRNA expression and absent LMO2 protein (Natkunam et al., Blood 109:1636-1642, 2007), were simultaneously transfected with the gRNA/Cas9 plasmid and one of the donor (provirus-containing) plasmids. Approximately 2 weeks after transfection, 9.7%, 28.2%, and 12.1% of GV, LV, and FV transfected pools showed GFP transgene expression, when GFP positive cells were sorted into single cells (FIG. 3A). Clones were then harvested and screened by PCR for homology directed insertion of the proviruses (FIGS. 3B-D).

When editing with CRISPR/Cas9, it is possible to edit more than one allele in a given clone, especially in highly transfectable cell lines. This would result in either proviral sequences integrated into multiple LMO2 alleles in a given HeLa cell (provirus-targeted alleles), or the double strand break (DSB) would be repaired by non-homologous end joining, creating a small indel (termed 'edited non-targeted' alleles hereafter). Since HeLa cells have very low LMO2 mRNA expression, do not express LMO2 protein, and the proviruses are being targeted to an intron of the LMO2 gene, LMO2 expression would be influenced by the virus enhancers only in the provirus-targeted alleles. Moreover, the reading frame of LMO2 (and its mRNA expression) would not be altered by an edited non-targeted allele. The proviral plasmid could also randomly integrate into the genome in HeLa cells, resulting in GFP expression, but would not affect LMO2 expression. Due to the potential for random integration, the number of provirus-targeted LMO2 alleles that the clones had could not be determined by qPCR of the proviral sequences. Therefore, the targeted allele copy number was calculated indirectly (see Materials and Methods and Table 2). Briefly, FISH for the LMO2 locus on control HeLa cells showed four LMO2 alleles. Next, copy number analysis was used to detect unedited alleles and alleles containing small indels. PCR across the target site with a larger amplicon followed by gel electrophoresis and sequencing was used to detect larger indels that would not be detected by copy number analysis. Upon sequencing of the PCR product, one LMO2 allele with a 261-bp deletion was found in three of the LV clones that initially showed only one non-targeted/WT allele on copy number analysis (indicated by stars in FIG. 9B and arrows in FIG. 9C). One LV clone and three FV clones did not amplify (FIG. 9C). The number of targeted alleles for a given clone equals the number of LMO2 loci, subtracted by the number of non-targeted alleles detected by copy number analysis and PCR, and are listed in Table 2. Overall, comparable numbers of LMO2 alleles were targeted (2-3 targeted alleles in most clones) with FV, LV or GV.

Figure 5:
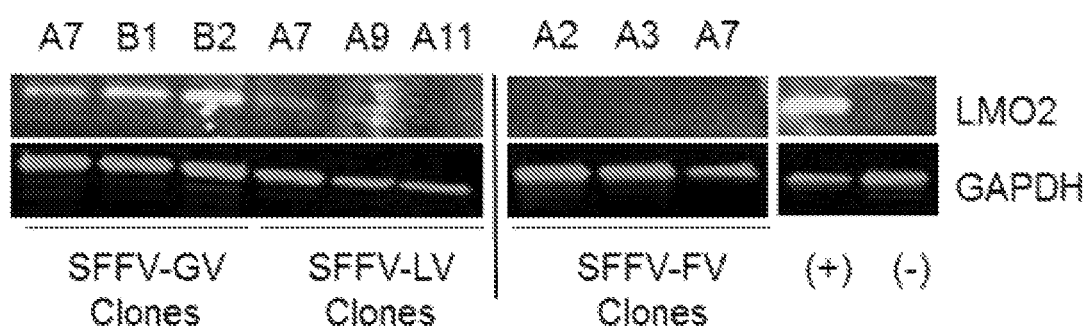
FIG. 5 is a photo showing that FV induces LMO2 protein expression to a lesser extent than either GV or LV. (−) and (+) denote the negative and positive controls, respectively.

The advantage to using the HeLa cell line without significant endogenous LMO2 expression is that editing events that abrogate gene expression would not significantly affect the overall increase in LMO2 expression due to directed proviral insertion events. LMO2 mRNA expression in the generated HeLa clones was determined by qRT-PCR with two probe and primer sets. The primers were selected to detect all spliced transcript variants expressed from the LMO2 promoter, from both modified or WT alleles. Data from both primer sets using two different loading controls were very similar (FIGS. 4A-4D). Overall, the results found the SFFV enhancer in GV demonstrated the greatest fold-increase in LMO2 mRNA expression (median increase of 280±23-fold over unmodified HeLa cells), followed by the SFFV enhancer in LV (median 200±27-fold increase). It is to be noted that SFFV-GV provirus had two copies of the enhancer at either LTR, while the SFFV-LV (and SFFV-FV) had only one copy of the SFFV enhancer. However, the same SFFV enhancer in FV showed a remarkably lower (45±7-fold median) increase in LMO2 mRNA expression, a 4- and 6-fold reduced expression than was seen with the SFFV enhancer in LV and GV, respectively. Subsequently, a western blot analysis to detect LMO2 protein expression from three representative clones from the ones used for qRT-PCR was performed (FIG. 5 and Table 2.) LMO2 expression in SFFV-FV clones was not detected, which was similar to baseline in mock (non-edited) HeLa cells. However, significantly higher LMO2 protein was detectable in GV and LV clones. Taken together, the qRT-PCR and western blot analysis confirm that the FV backbone/cis-elements have a strong enhancer blocking or insulator effect, which likely contributes to the reduced ability of SFFV enhancer to upregulate the expression of LMO2.

TABLE 2

Number or WT or indel alleles in each clone

| Clone | Number of WT or indel alleles | [Calculated Provirus-Targeted Alleles]** | Used for western blot |
|---|---|---|---|
| GV A7 | 2 | 2 | X |
| GV B1 | 2 | 2 | X |
| GV B2 | 2 | 2 | X |
| GV B3 | 2 | 2 | |
| GV B4 | 2 | 2 | |
| GV B12 | 3 | 1 | |
| LV A2* | 2 | 2 | |
| LV A7# | 1 | 3 | X |
| LV A9 | 1 | 3 | X |
| LV A11 | 1 | 3 | X |
| LV B1 | 2 | 2 | |
| LV B3 | 1 | 3 | |
| LV B8 | 2 | 2 | |
| LV B11* | 2 | 2 | |

TABLE 2-continued

Number or WT or indel alleles in each clone

| Clone | Number of WT or indel alleles | [Calculated Provirus-Targeted Alleles]** | Used for western blot |
|---|---|---|---|
| LV C2* | 2 | 2 | |
| FV A2 | 2 | 2 | X |
| FV A3 | 2 | 2 | X |
| FV A7 | 2 | 2 | X |
| FV A8# | 2 | 2 | |
| FV A10 | 1 | 3 | |
| FV A11 | 2 | 2 | |
| FV B1# | 1 | 3 | |
| FV B8## | 2 | 2 | |
| FV C1 | 2 | 2 | |
| FV C2 | 2 | 2 | |
| FV C4# | 1 | 3 | |

*Clones LV A2, LV B11, and LV C2 contain an allele with a 261-bp intronic deletion that would not be detected via copy number analysis.
**Assuming that all clones have 4 LMO2 alleles, like the parental HeLa cells from which they were derived.
Clones LV A7, FV A8, FV B1, and FV C4 had no PCR amplicon when assessing for large deletions by PCR.
Clone FV B8 was not assayed for large deletions due to lack of sample material. For clones LV A7, FV A8, FV B1, FV B8, and FV C4, the calculated provirus-targeted-alleles were calculated solely on copy number analysis.

(D) In Silico Insulator Analysis Identified a Greater Number of CTCF Binding Motifs in the FV Backbone than in the GV and LV Backbones.

A likely mechanism for the observed enhancer blocking effect of the FV backbone, based on the results, is that it contains one or more insulator elements. To test this, an in silico analysis for CTCF binding sites, the main insulator in vertebrates, was performed. The proviral sequences of GV, LV, and FV vectors (excluding the SFFV enhancer/promoter, eGFP and WPRE sequences) were analyzed for predicted CTCF binding sites, or consensus sequences, using the CTCFBSDB 2.0 database (http://insulatordb.uthsc.edu/) (Ziebarth et al., *Nucleic Acids Res.* 41:D188-94, 2013) to identify core motifs for CTCF binding, represented as position weight matrices (PWM). The algorithm searches for identified core motifs for CTCF binding sites and represents the motifs as PWM. PWM scores correspond to the log-odds of the observed sequence being generated by the motif versus being generated by the background. A PWM score >3.0 is suggestive of a significant match. A limitation of the prediction tool is that it only returns the best match for a given PWM in a sequence. Therefore, other putative CTCF consensus sequences for a given motif within the same analyzed sequence are not revealed. To partially account for this, sequences were divided into several fragments and each fragment was analyzed separately.

Figure 6A:
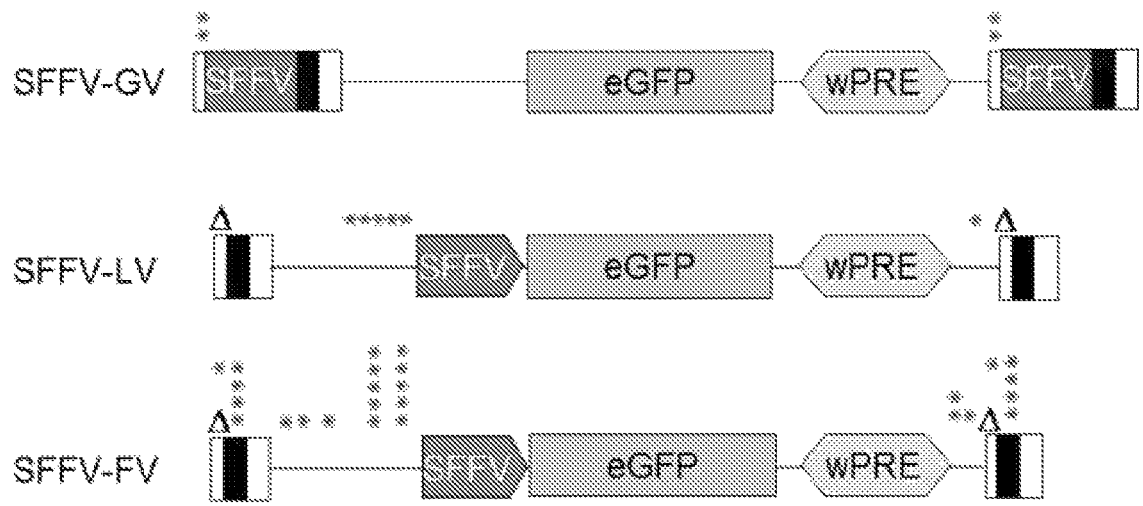
FIGS. 6A-6B include diagrams showing high number of CCCTC binding factor (CTCF) insulator binding sites in the sequence of FV.
Figure 6B:
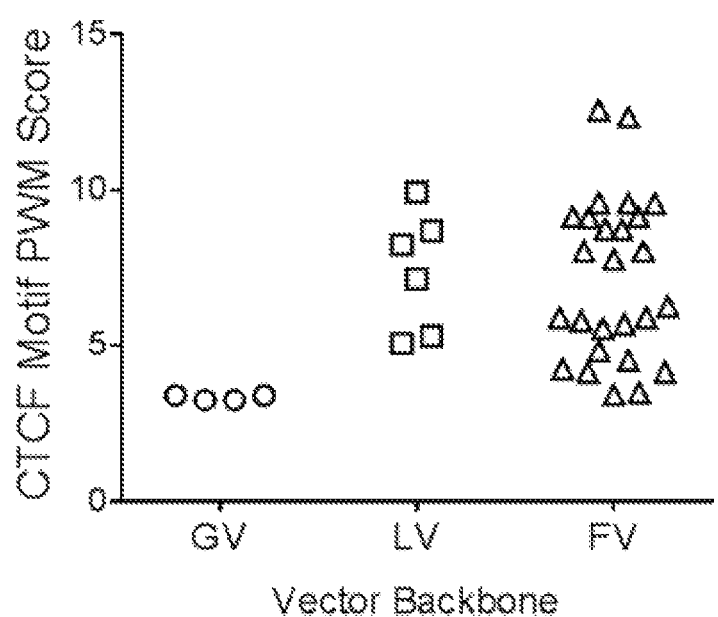

Analysis of the vector backbone sequences identified a total of 4, 6 and 26 motifs with PWM>3 for GV, LV, and FV, respectively. The location of the motifs in the vector backbone is depicted in FIG. 6A and Table 3, and their PWM score in FIG. 6B. Besides the number of significant PWMs, the PWM scores for GV were lower in general, and ranged from 3.3 to 3.4, while PWM scores for LV ranged from 5.1 to 9.9 and PWM scores for FV ranged from 3.4 to 12.6. Motifs for FV were dispersed both in the LTR and the cis-sequences compared to GV. Overall, the in silico analysis suggested that FV had a greater number of predicted CTCF binding motifs and motifs with higher PWM scores, compared to GV and LV.

TABLE 3

Predicted CTCF binding motifs

| Vector | Motif PWM | Motif Sequence | Score | Location from 3' HA | Motif Orientation | Associated Feature |
|---|---|---|---|---|---|---|
| GV | MIT_LM23 | AAACCTACAGGTGGGGTCTT (SEQ ID NO: 115) | 3.40278 | 88 | − | 5' LTR |
| | EMBL_M1 | CCCCACCTGTAGGT(SEQ ID NO: 116) | 3.2515 | 92 | + | 5' LTR |
| | MIT_LM23 | AAACCTACAGGTGGGGTCTT(SEQ ID NO: 117) | 3.40278 | 2105 | − | 3' LTR |
| | EMBL_M1 | CCCCACCTGTAGGT(SEQ ID NO: 118) | 3.2515 | 2109 | + | 3' LTR |
| LV | EMBL_M1 | TTCCCCCTGGCCTT(SEQ ID NO: 119) | 5.30958 | 427 | − | after Psi |
| | EMBL_M2 | GGAAGAGCA | 8.68716 | 679 | + | after Psi |
| | EMBL_M1 | CTCCTCCTCCAGGT(SEQ ID NO: 120) | 7.14542 | 734 | − | after Psi |
| | MIT_LM7 | TCCCCAGGAGCTGTTGATCC(SEQ ID NO: 121) | 5.08224 | 1091 | − | after Psi |
| | EMBL_M2 | GGCACAGCA | 9.92719 | 1145 | − | after Psi |
| | EMBL_M2 | GGTACAGCT | 8.25192 | 3579 | − | before 3' LTR |
| FV | EMBL_M2 | AGCATTGCA | 9.5685 | 142 | − | 5' LTR |
| | MIT_LM23 | ATATCACTAGATGTCTCCCT(SEQ ID NO: 122) | 4.14861 | 273 | − | 5' LTR |

TABLE 3-continued

Predicted CTCF binding motifs

| Vector | Motif PWM | Motif Sequence | Score | Location from 3' HA | Motif Orientation | Associated Feature |
|---|---|---|---|---|---|---|
| | MIT_LM7 | ATATCACTAGATGTCTCCCT(SEQ ID NO: 123) | 8.73461 | 273 | − | 5' LTR |
| | MIT_LM2 | ATATCACTAGATGTCTCCC(SEQ ID NO: 124) | 8.02923 | 274 | − | 5' LTR |
| | EMBL_M1 | AGACATCTAGTGAT(SEQ ID NO: 125) | 5.89526 | 277 | + | 5' LTR |
| | EMBL_M2 | AGCATAGCG | 3.42649 | 429 | + | before gag |
| | EMBL_M2 | GGCATTGCC | 9.56461 | 1304 | − | Pro-Pol |
| | EMBL_M2 | GGAATTGCA | 12.3512 | 1882 | − | Pro-Pol/Integrase |
| | REN_20 | TGGTCCAGGAGAGGGTGGCT(SEQ ID NO: 126) | 9.14351 | 2319 | + | Pro-Pol/Integrase |
| | MIT_LM23 | GGTCCAGGAGAGGGTGGCTA(SEQ ID NO: 127) | 3.48392 | 2320 | + | Pro-Pol/Integrase |
| | MIT_LM2 | GGTCCAGGAGAGGGTGGCT(SEQ ID NO: 128) | 5.54859 | 2320 | + | Pro-Pol/Integrase |
| | MIT_LM7 | GGTCCAGGAGAGGGTGGCTA(SEQ ID NO: 129) | 9.1009 | 2320 | + | Pro-Pol/Integrase |
| | EMBL_M1 | CACCCTCTCCTGGA(SEQ ID NO: 130) | 12.5569 | 2322 | − | Pro-Pol/Integrase |
| | MIT_LM2 | TGAACAGCAGAAGGAACAA(SEQ ID NO: 131) | 4.26098 | 2570 | + | ENV |
| | MIT_LM23 | TGAACAGCAGAAGGAACAAA(SEQ ID NO: 132) | 4.51999 | 2570 | + | ENV |
| | MIT_LM7 | TGAACAGCAGAAGGAACAAA(SEQ ID NO: 133) | 6.26218 | 2570 | + | ENV |
| | EMBL_M2 | TGAACAGCA | 7.76981 | 2570 | + | ENV |
| | EMBL_M1 | TTCCTTCTGCTGTT(SEQ ID NO: 134) | 9.13542 | 2572 | − | ENV |
| | MIT_LM7 | TAACGAGGAGAGGGTGTGGT(SEQ ID NO: 135) | 4.82626 | 4898 | + | BEL3 |
| | EMBL_M1 | CACCCTCTCCTCGT(SEQ ID NO: 136) | 5.68719 | 4900 | − | BEL3 |
| | EMBL_M2 | GGCATTCCA | 5.79638 | 4917 | − | BEL3 |
| | EMBL_M2 | AGCATTGCA | 9.5685 | 5234 | − | 3' LTR |
| | MIT_LM23 | ATATCACTAGATGTCTCCCT(SEQ ID NO: 137) | 4.14861 | 5365 | − | 3' LTR |
| | MIT_LM7 | ATATCACTAGATGTCTCCCT(SEQ ID NO: 138) | 8.73461 | 5365 | − | 3' LTR |

TABLE 3-continued

Predicted CTCF binding motifs

| Vector | Motif PWM | Motif Sequence | Score | Location from 3' HA | Motif Orientation | Associated Feature |
|---|---|---|---|---|---|---|
| | MIT_LM2 | ATATCACTAGATGTCTCCC (SEQ ID NO: 139) | 8.02923 | 5366 | – | 3' LTR |
| | EMBL_M1 | AGACATCTAGTGAT (SEQ ID NO: 140) | 5.89526 | 5369 | + | 3' LTR |

(E) A Unique 36-bp Enhancer Blocking Element was Mapped in the FV Backbone

Figure 7A:
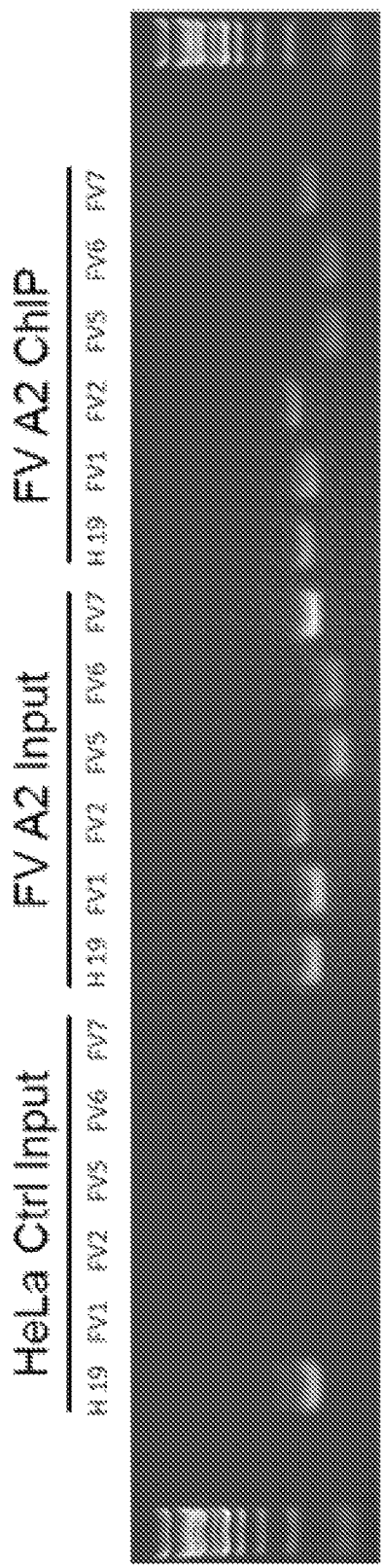

To assess for binding of CTCF to the proviral sequences within HeLa cells, ChIP purification of CTCF bound DNA was performed, followed by qualitative PCR for predicted binding sites within the FV proviral sequence (FIG. 7A). Using HeLa control cells, analysis of the ChIP input material showed amplification of only the H19-Igf2 locus, a known CTCF binding site. However, both the input material as well as the ChIP purified DNA from one of the FV clones (FVA2) showed amplification of five tested sites with high level of predicted binding. While ChIP analysis showed presence of CTCF binding, the close proximity of the assayed regions limits the resolution between sites by this ChIP-PCR assay. Regardless, the ChIP-PCR assay demonstrated in-cell binding of CTCF to the FV proviral sequence. An electrophoretic mobility shift assay (EMSA) was then used to map the predicted CTCF binding sites within LV and FV. 80-90-bp DNA fragments, corresponding to predicted CTCF binding sites by in silico analysis, labeled at both 5' ends with fluorescent dye were used as the EMSA probe. Five of the six predicted binding sites in LV were probed, and probes LV1, LV2, and FV8 contain two predicted CTCF binding motif sequences. EMSA was conducted using recombinant human CTCF. An H19 oligonucleotide, containing a consensus known to bind CTCF with high affinity was the positive control.

Figure 7B:
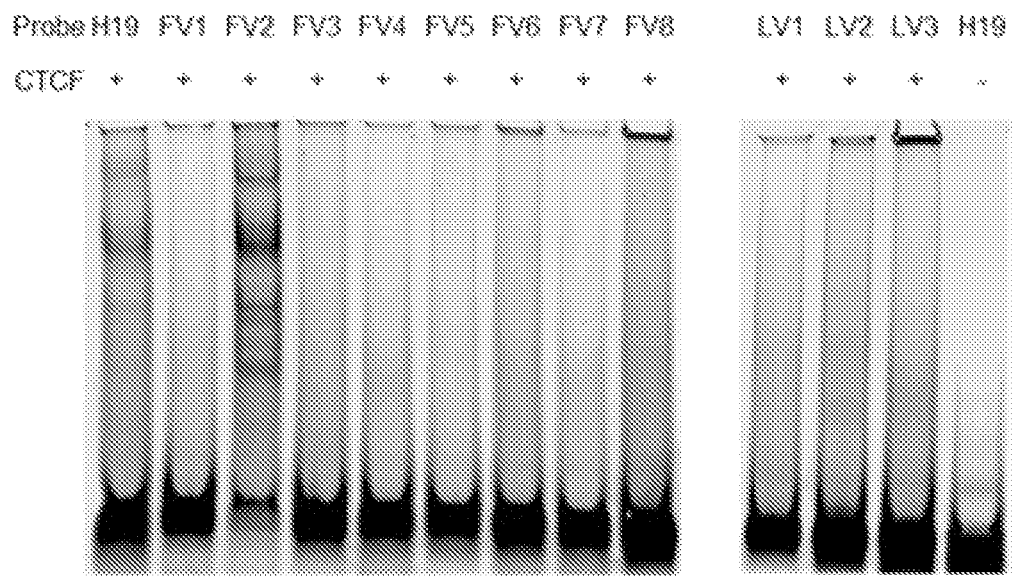
Figure 7C:
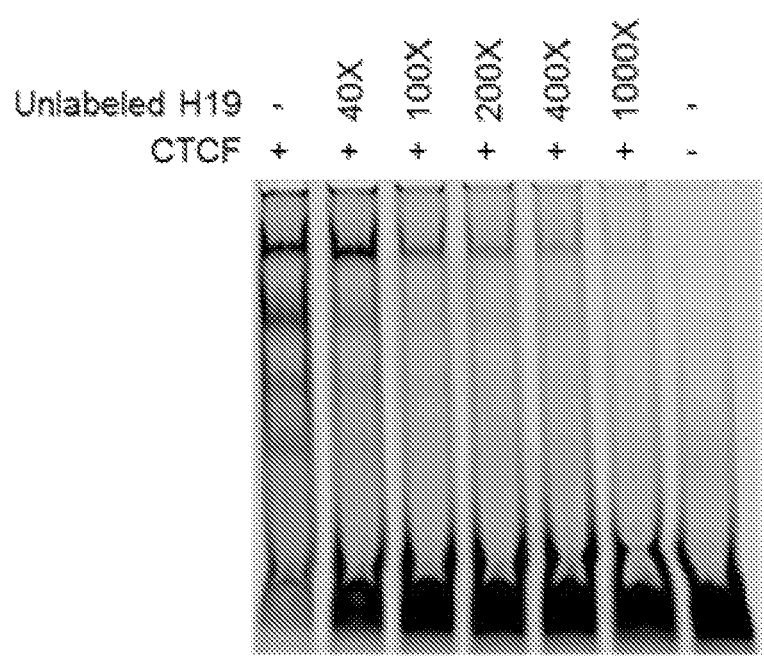

None of the LV probes demonstrated any binding to CTCF. However, probe FV2, corresponding to the sequence ATATCACTAGATGTCTCCCT (SEQ ID NO: 141) (located in the LTR, and containing four motifs with PWM scores of 4.1, 8.7, 8.0, and 5.9) demonstrated a significant band shift (FIG. 7B). Additionally, the labeled probe could be competed off with unlabeled H19 probe (FIG. 7C). The sequence for the FV2 probe was analyzed in silico for predicted CTCF binding sites. In addition to the previously predicted site, a second site was identified, 5'-TGTAGTTCA-3' with a score of 6.8. The central region of the FV2 probe was divided into four regions (1-4). Region 1 contained the newly identified predicted binding site. Regions 2-3 contained the original predicted binding site. Six mutant probes were designed that replaced one or more of the four regions with a scrambled DNA sequence (FIG. 7D). Sequences were analyzed to insure that no new predicted CTCF binding sites were created. Mutating region 1, 2, or 3 reduced the CTCF binding (EMSA band intensities, FIG. 7E). Mutating region 4 appeared to have no effect. Mutating region 1 and 3 together, or 2 and 3 together, further reduced CTCF binding. Therefore, the results found that CTCF binds the 36-bp sequence defined by regions 1-3 of the FV2 probe. A blast search (https://blast.ncbi.nlm.nih.gov/) using the defined sequence did not reveal matches to any sequences other than foamy virus.

(F) Insulator Function was Verified by Targeted Insertion into the LMO2 Gene

Figure 8:
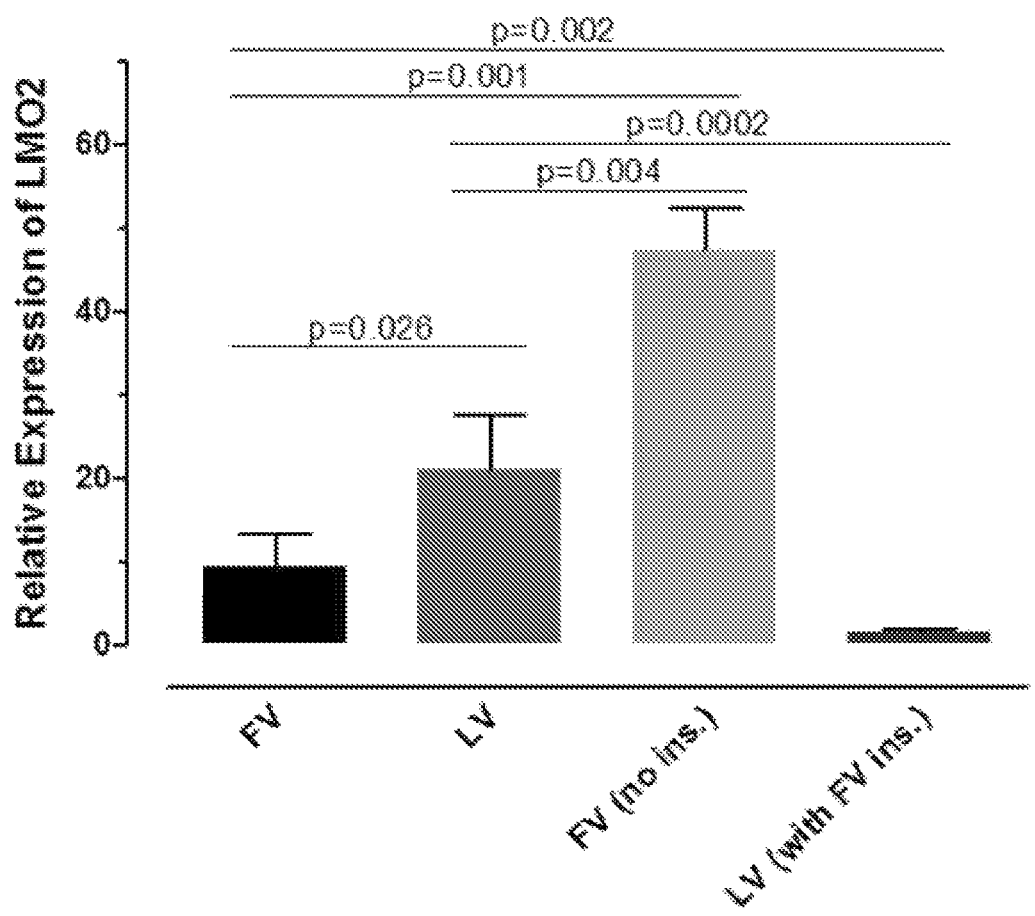
FIG. 8 is a chart showing that induction of LMO2 mRNA expression by FV is increased when the insulator (ins.) is removed and induction of LMO2 mRNA expression by LV is decreased when the insulator is added to the LV LTR.

To verify the insulator function of the defined CTCF-binding sequence: 1) the 36-bp sequence was precisely excised from the proviral SFFV-FV sequence, leaving the rest of the sequence intact; and 2) the proposed insulator was inserted into both the LTRs of the SFFV-LV proviral sequence. The modified proviral sequences were then inserted into the LMO2 gene using the CRISPR/Cas9 based targeted insertional genotoxicity assay, as before. Expression of LMO2 relative to control HeLa cells, and LV and FV clones used previously, was determined by qPCR using the Hs001534473_m1 primer/probe set and PPIA endogenous control (FIG. 8). Removing the insulator from the FV LTR resulted in an over 5-fold increase in relative LMO2 expression (9.4 to 47.4, p=0.001). Inserting the sequence into the LV LTR resulted in an over 13-fold drop in relative LMO2 expression (21.0 to 1.6, p=0.0002). Interestingly, placing the insulator into the LTR of SFFV-LV resulted in LMO2 expression that was only 1.6-fold higher than control HeLa cells and significantly less than the original SFFV-FV containing the insulator (p=0.002). The overall lower relative expression seen in this assay, compared to the prior assay using GV, LV, and FV, was due to higher observed expression of LMO2 in the control HeLa cells. Based on the prior assay, the number of inserted proviral sequences did not correlate well with LMO2 expression. Copy number determined by qPCR only, predicted that all of the new FV clones without the insulator had three correctly placed proviral sequences. Of the new LV clones containing the insulator 6, 1, and 2 clones contained 1, 2, and 3 copies of the proviral sequence, respectively. Again, the number of inserted proviral sequences did not seem to correlate with expression levels.

Taken together, the results showed that FV LTRs contain a strong 36-bp CTCF binding motif that has potent CTCF binding that produces an enhancer blocking effect, and serves to protect nearby genes from the enhancer activity of a delivered transgene. These data provide novel insight into the remarkably low immortalization potential of SFFV (and MSCV) in FV vectors, demonstrating a previously unreported and significant mechanism contributing to the lower genotoxicity of FV carrying strong viral enhancers.

Discussion

Vector-driven genotoxicity is primarily caused by the use of strong enhancers (in the LTR) (Modlich et al., Blood 108:2545-53, 2006, Zychlinski et al., Mol. Ther. 16:718-25, 2008, Kustikova et al., Science 308:1171-4, 2005, Maruggi et al., Mol. Ther. 17:851-6, 2009) and by the integration site preference of the vector (Montini et al., J. Clin. Invest. 119:964-75, 2009, Montini et al., Nat. Biotechnol. 24:687-96, 2006). GV LTR enhancers ubiquitously and strongly enhance expression of the transgene, leading to a therapeutic correction, but also enhance expression of genes flanking the transgene insertion site, that can lead to leukemia. In addition, both GV and LV integrases target the provirus to gene-rich regions nearly 60-70% of the time, while GV vectors tend to integrate near TSS, and LV vectors have a strong preference for integrating within introns of active transcriptional units, and thus have a lower propensity to activate transcription of cellular genes (Modlich et al., *Blood* 108:2545-53, 2006, Zychlinski et al., *Mol. Ther.* 16:718-25, 2008, Kustikova et al., *Science* 308:1171-4, 2005, Maruggi et al., *Mol. Ther.* 17:851-6, 2009). Overall, LV vectors carrying GV LTR enhancers tend to have an approximately 10-20 fold lower genotoxic potential in in vitro and in vivo experimental systems, when compared to GV vectors carrying the same enhancers (Modlich et al., *Blood* 108:2545-53, 2006, Montini et al. *J. Clin. Invest.* 119:964-75, 2009).

LMO2 targeted GV, LV, and FV clones assayed by qRT-PCR and western blot for LMO2 expression mirrored the immortalization assay results: a 6-fold reduced SFFV enhancer effect was seen with FV as compared to GV. This may be partly explained by the fact that the GV vector has two SFFV enhancers, while the FV vector has only one. However, FV also had a 4-fold reduction in enhancer effect when compared to LV, which also has only a single SFFV enhancer placed internally, similar to FV. Similarly, Western blot analysis of LMO2 protein expression demonstrated a 3-fold reduction in LMO2 expression in LV clones compared to GV clones. LMO2 expression was undetectable for FV clones, showing a very potent SFFV enhancer blocking by the FV vector sequences.

This remarkable reduction in the effect of a strong enhancer, such as SFFV, led to the unexpected discovery of an insulator in the FV vector cis sequences. In silico analysis for binding sites for CTCF, the primary vertebrate insulator protein, showed CTCF Position Weight Matrices (PWMs) for GV in the beginning of the U3 region of each LTR just prior to the enhancer/promoter, but all with low PWM scores below 3.5 (Table 3 lists the location of the motifs). LV had 6 unique CTCF PWMs with scores ranging from 5.3 to 9.9. FV had 26 CTCF PWMs with scores ranging from 3.5 to 12.6 that were present in the SIN LTR and the portions of gag, pro-pol, env and bel cis sequences retrained in the FV vector, of which eleven were non-overlapping CTCF PWMs, and two were within the R-region of the LTRs. If a more stringent score cut-off for PWM score is used, e.g. 3.5, GV lost all of its CTCF binding sites, while none of the LV and only 2 of the FV CTCF binding sites were lost. However, no detectable CTCF binding to the tested in silico predicted LV CTCF-binding sites was observed.

Binding of CTCF to one of the predicted binding sites within the FV LTR sequences was demonstrated using EMSA, and the CTCF binding was mapped to a 36-bp region. Location within the LTR is notable, as this would provide insulation at both ends of the proviral sequence. Recently, CTCF binding sites experimentally inserted into the LV or FV LTR have shown to reduce genotoxicity (Liu et al., *Nat. Biotechnol.* 33:198-203, 2015, Browning et al., *Human Gene Therapy* 27:255-266, 2015, Browning et al., *Gene Ther.* 24:187-198, 2017) Our studies show that inherent CTCF binding sites already exist within the FV LTR. By removing the CTCF binding site from the FV proviral sequence, the reduction in genotoxicity seen in our LMO2 activation assay was abrogated. Conversely, inserting this site into the LV LTR significantly reduced genotoxicity in the same assay to levels only slightly above control.

Importantly, these studies led to identification of a novel insulator sequence with strong enhancer blocking activity, making the use of this strong insulator fragment an attractive tool in construct nucleic acid constructs such as viral vector for expressing transgenes requiring strong enhancers. Additionally, this sequence can be transposable into other vectors, with the possibility of achieving insulator functions such as reducing genotoxicity. The risk of insertional immortalization has been reported to be greatly reduced in SIN GV and LV vectors expressing transgenes via the elongation factor-1 EF-1 (EFS) and phosphoglycerate kinase (PGK) promoters due to their weak/negligible enhancer activity (Zychlinski et al., *Mol. Ther.* 16:718-25, 2008). However, a major limitation with the use of cellular promoters is the problem of obtaining and maintaining a consistently high level of transgene expression. In diseases like LAD (Hunter et al., *Hum. Gene Ther.* 22:689-96, 2011), CGD (Barde et al., *Gene Ther.* 18:1087-97, 2011, Chiriaco et al., *Mol. Ther.* 22:1472-83, 2014), and WAS (Aiuti et al., *Science* 341:1233151, 2013, Hacein-Bey Abina et al., *JAMA* 313:1550-63, 2015), where a high level of transgene expression is required to achieve a therapeutic benefit, cellular promoters were insufficient to mediate a therapeutic effect, unless both high VCNs were present and strong enhancers were used. In fact, we have recently reported that expression of perforin from cellular or endogenous promoters in LV only partially corrects the hemophagocytic lymphohistiocytosis (HLH) phenotype, and strong viral enhancers are necessary for complete correction (Tiwari et al., *Hum. Gene Ther.* 27(10): 847-859, 2016).

This disclosure shows that strong viral LTR enhancers within FV vectors may be applicable, as the combined tendency to integrate in non-genic regions combined with an inherent insulator effect, can remarkably reduce the genotoxicity.

In summary, direct comparison of the genotoxic potential induced by analogous GV, LV and FV vectors displays remarkably reduced immortalization potential of HSPCs from insertions of FV vectors carrying some of the most genotoxic viral enhancers. Interrogating the sole effect of vector backbones on genotoxicity using CRISPR/Cas9 mediated targeted integration of GV, LV, and FV viral sequences at a specific LMO2 locus reveals that the mechanism of this reduced genotoxicity, is in large part due to an enhancer blocking insulator effect in the FV LTRs that strongly bind CTCF. This disclosure provides valuable insights into genotoxicity of FV vectors and has relevance to clinical vector design. The identified small (36-bp) insulator sequence could be of potential use in a wide variety of vectors, especially when addition of strong enhancers is critical for disease correction.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A nucleic acid construct for gene delivery, the nucleic acid construct comprising at least one gene of interest (GOI) flanked by an insulator fragment, said insulator fragment consisting essentially of a nucleotide sequence having at least 90% sequence identity to AAGGGAGACATCTAGT-GATATAAGTGTGAACT ACAC (SEQ ID NO:2) or at least 90% sequence identity to GTGTAGTTCACACTTATAT-CACTAGATGTCTCCCTT (SEQ ID NO: 1), said insulator fragment being heterologous to at least one fragment of said nucleic acid.

2. The nucleic acid construct of claim 1, wherein the insulator fragment comprises the nucleotide sequence of SEQ ID NO:2 or SEQ ID NO: 1.

3. The nucleic acid construct of claim 1, wherein the insulator fragment comprises multiple copies of SEQ ID NO:2 or SEQ ID NO: 1.

4. The nucleic acid construct of claim 1, wherein the GOI encodes an agent of interest, which is a protein or a nucleic acid.

5. The nucleic acid construct of claim 4, wherein to GOI encodes a therapeutic protein, which is an antibody, a growth factor, a cytokine, a coagulation factor, an enyzme, or a hemoglobin; or wherein the GOI is a nuleic acid, which is an interfering RNA, an anti-sense eligonucleotide, or microRNA.

6. The nucleic acid construct of claim 1, wherein the insulator fragment is located upstream to the GOI or downstream to the GOI.

7. The nucleic acid construct of claim 1, wherein the nucleic acid construct comprises at least two copies of the insulator fragment, one being upstream to the GOI, and the other one being downstream to the GOI.

8. The nucleic acid construct of claim 1, wherein the nucleic acid construct comprises two GOIs, and at least one insulator fragment is located between the two GOIs.

9. The nucleic acid construct of claim 1, wherein the nucleic acid construct is a vector.

10. The nucleic acid construct of claim 9, wherein the vector is a viral vector.

11. The nucleic acid construct of claim 10, wherein the viral vector is a retroviral vector, an adenoviral vector, or an adeno-associated viral vector.

12. The nucleic acid construct of claim 11, wherein the vector is a retroviral vector, which comprises a 5' long terminal repeat (LTR) and a 3'LTR, wherein the insulator fragment is located inside the 5' LTR, inside the 3'LTR, or inside both the 5' LTR and 3' LTR, and wherein the insulator is heterologous to the 5' LTR and/or the 3'LTR.

13. The nucleic acid construct of claim 12, wherein the nucleic acid construct comprises multiple copies of the insulator fragment, at least one of which is located inside either the 5' LTR or the 3' LTR and at least one of which is located adjacent to the GOI, either upstream or downstream.

14. The nucleic acid construct of claim 11, wherein the viral vector is a retroviral vector, which is a lentivirus vector or a gammaretrovirus vector.

15. The nucleic acid construct of claim 12, wherein the 3'LTR comprises a polyadenylation (polyA) enhancer signal sequence.

16. The nucleic acid construct of claim 15, wherein the upstream polyadenylation (polyA) enhancer signal sequence is an upstream sequence element (USE) derived from an SV40 late polyA signal sequence; or wherein the upstream polyA enhancer signal sequence replaces a U3 region in the 3' LTR.

17. The nucleic acid construct of claim 11, which further comprises one or more of the following elements:
a psi (ψ) packaging signal;
a rev response element (RRE);
a gag element;
an env splice acceptor sequence;
one or more copies of a heterologous polyA signal sequence downstream from a 3' LTR;
one or more chromatin insulator elements;
a central polypurine tract (cPPT); and
a post-transcriptional regulatory element (PRE).

18. The nucleic acid construct of claim 11, which is a self-inactivating (SIN) retroviral vector.

19. The nucleic acid construct of claim 1, wherein the nucleic acid construct is a gene target construct for use in gene editing.

20. A method for delivering an agent of interest to host cells, the method comprising contacting host cells with an effective amount of a nucleic acid construct of claim 1.

21. A method for delivering an agent of interest to a subject, the method comprising administering to a subject in need thereof a viral particle comprising a genetic material produced from a retroviral vector set forth in claim 11.

22. A method for integrating an exogenous gene into the genome of host cells, the method comprising (i) delivering a DNA endonuclease and a gene targeting construct set forth in claim 19 into host cells, and (11) incubating the host cells under conditions allowing for cleavage at a site of a chromosome of the host cells and integration of the gene targeting construct into the chromosome.

23. A nucleic acid consisting essentially of a nucleotide sequence at least 90% identical to SEQ ID NO:2 or at least 90% identical to GTGTAGTTCACACTTATATCACTAGATGTCTCCCTT (SEQ ID NO: 1), wherein the nucleic acid is an insulator, said insulator being heterologous to at least one fragment of said nucleic acid.

24. The nucleic acid of claim 23, wherein the nucleic acid comprises the nucleotide sequence of SEQ ID NO:2 or SEQ ID NO: 1.

\* \* \* \* \*